United States Patent
Matsushita et al.

(10) Patent No.: US 10,014,474 B2
(45) Date of Patent: Jul. 3, 2018

(54) COMPOSITION FOR FORMING GATE INSULATING FILM, ORGANIC THIN FILM TRANSISTOR, ELECTRONIC PAPER, AND DISPLAY DEVICE

(71) Applicant: FUJIFILM Corporation, Tokyo (JP)

(72) Inventors: Yasuaki Matsushita, Kanagawa (JP); Tokihiko Matsumura, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 5 days.

(21) Appl. No.: 14/955,698

(22) Filed: Dec. 1, 2015

(65) Prior Publication Data

US 2016/0087208 A1 Mar. 24, 2016

Related U.S. Application Data

(63) Continuation of application No. PCT/JP2014/064528, filed on May 30, 2014.

(30) Foreign Application Priority Data

Jun. 7, 2013 (JP) .................................. 2013-120985

(51) Int. Cl.
*H01L 51/00* (2006.01)
*C07F 9/145* (2006.01)
(Continued)

(52) U.S. Cl.
CPC ............ *H01L 51/004* (2013.01); *C07F 9/145* (2013.01); *C08L 33/14* (2013.01);
(Continued)

(58) Field of Classification Search
CPC . H01L 51/004; H01L 51/0034; H01L 51/052; H01L 51/0545; C07F 9/145; C08L 33/14; C08F 220/10

(Continued)

(56) References Cited

U.S. PATENT DOCUMENTS 3,909,680 A 9/1975 Tsunashima
2010/0155731 A1* 6/2010 Sun ..................... G06F 3/0412
257/59
2011/0193071 A1 8/2011 Yahagi

FOREIGN PATENT DOCUMENTS

CN 102138218 A 7/2011
EP 2320467 A1 5/2011
(Continued)

OTHER PUBLICATIONS

International Search Report—PCT/JP2014/064528 dated Sep. 2, 2014.
(Continued)

*Primary Examiner* — Josephine L Chang
(74) *Attorney, Agent, or Firm* — Studebaker & Brackett PC

(57) ABSTRACT

The present invention provides a composition for forming a gate insulating film, which improves the insulation reliability of an organic thin film transistor without greatly reducing the mobility of the organic thin film transistor, an organic thin film transistor, electronic paper, and a display device. The composition for forming a gate insulating film of the present invention contains an insulating material and a migration inhibitor selected from the group consisting of a compound represented by any of Formulae (1) to (8), a polymer compound (X) containing a repeating unit represented by Formula (A), and a polymer compound (Y) containing a repeating unit represented by Formula (B) and a repeating unit represented by Formula (C).

4 Claims, 1 Drawing Sheet

(51) Int. Cl.
  *C08L 33/14* (2006.01)
  *H01L 51/05* (2006.01)
(52) U.S. Cl.
  CPC ........ *H01L 51/0034* (2013.01); *H01L 51/052* (2013.01); *H01L 51/0545* (2013.01)
(58) Field of Classification Search
  USPC ................................. 524/520, 523, 543, 516
  See application file for complete search history.

(56) References Cited

FOREIGN PATENT DOCUMENTS

| | | | |
|---|---|---|---|
| EP | 2586805 | A1 | 5/2013 |
| EP | 2933244 | A1 | 10/2015 |
| JP | 2005-005582 | A | 1/2005 |
| JP | 2009-080443 | A | 4/2009 |
| JP | 2012-109542 | A | 6/2012 |
| JP | 2013-008951 | A | 1/2013 |
| JP | 5169167 | B2 | 3/2013 |
| WO | 2010/024238 | A1 | 3/2010 |
| WO | 2010/057984 | A2 | 5/2010 |
| WO | 2011/065568 | A1 | 6/2011 |

OTHER PUBLICATIONS

The partial supplementary European search report issued by the European Patent Office dated May 23, 2016, which corresponds to European Patent Application No. 14808410.6-1301 and is related to U.S. Appl. No. 14/955,698.
The extended European search report issued by the European Patent Office dated Jul. 11, 2016, which corresponds to European Patent Application No. 14808410.6-1301 and is related to U.S. Appl. No. 14/955,698.
An Office Action "Notice of Reasons for Refusal" issued by the Japanese Patent Office dated Sep. 6, 2016, which corresponds to Japanese Patent Application No. 2015-521432 and is related to U.S. Appl. No. 4/955,698; with English language partial translation.
An Office Action issued by the Chinese Patent Office dated Mar. 28, 2017, which corresponds to Japanese Patent Application No. 201480032277.0 and is related to U.S. Appl. No. 14/955,698; with English language translation.
Notification of Transmittal of Translation of the International Preliminary Report on Patentability and Translation of Written Opinion of the International Searching Authority; PCT/JP2014/064528 dated Dec. 17, 2015.
Communication pursuant to Article 94(3) EPC issued by the European Patent Office dated Mar. 20, 2018, which corresponds to European Patent Application No. 14 808 410.6-1107 and is related to U.S. Appl. No. 14/955,698.

\* cited by examiner

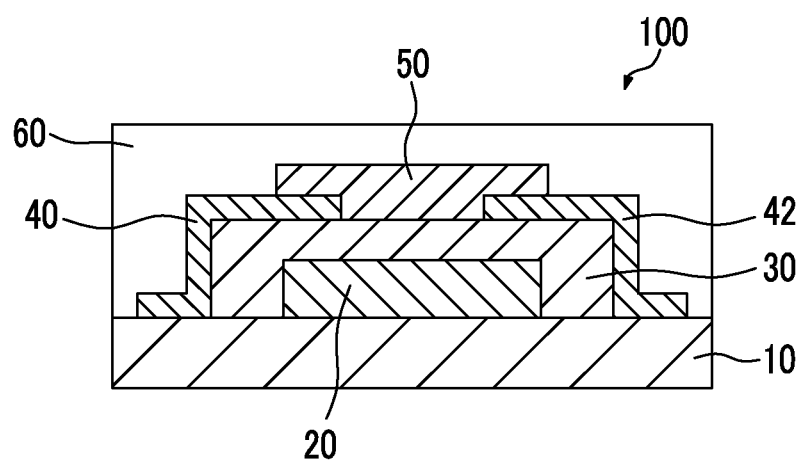

COMPOSITION FOR FORMING GATE INSULATING FILM, ORGANIC THIN FILM TRANSISTOR, ELECTRONIC PAPER, AND DISPLAY DEVICE

CROSS-REFERENCE TO RELATED APPLICATIONS

This application is a Continuation of PCT International Application No. PCT/JP2014/064528 filed on May 30, 2014, which claims priority under 35 U.S.C. § 119(a) to Japanese Patent Application No. 2013-120985 filed on Jun. 7, 2013. Each of the above applications is hereby expressly incorporated by reference, in its entirety, into the present application.

BACKGROUND OF THE INVENTION

1. Field of the Invention

The present invention relates to a composition for forming a gate insulating film, an organic thin film transistor, electronic paper, and a display device.

2. Description of the Related Art

In apparatuses using a logical circuit such as a field effect transistor (FET), RF tag (RFID), or memory used in a liquid crystal display or an organic EL display, an organic thin film transistor (TFT) having an organic semiconductor film (organic semiconductor layer) is used, because the use of the organic thin film transistor makes it possible to lighten the weight of the apparatus, reduce the cost, and make the apparatus flexible.

In recent years, as expectations for the organic thin film transistor have increased, the improvement of mobility (particularly, field effect mobility), stability, and the like have been required for the organic thin film transistor.

Under these circumstances, JP2005-5582A discloses an organic thin film transistor in which an organic semiconductor layer is formed of a composition containing an antioxidant so as to reduce the oxidation-induced deterioration of the organic semiconductor layer.

SUMMARY OF THE INVENTION

As a result of preparing an organic thin film transistor by using the composition disclosed in JP2005-5582A, the inventors of the present invention found that the mobility of the organic thin film transistor was greatly reduced. Furthermore, as a result of performing a service life test, the inventors found that the insulation reliability between source/drain electrodes needs to be further improved.

The present invention has been made under the aforementioned current circumstances, and an object thereof is to provide a composition for forming a gate insulating film, which improves the insulation reliability of an organic thin film transistor without greatly reducing the mobility of the organic thin film transistor, and an organic thin film transistor which is prepared by using the composition for forming a gate insulating film.

In order to achieve the aforementioned object, the inventors of the present invention conducted intensive examination. As a result, they obtained knowledge that, by using a composition for forming a gate insulating film that contains a predetermined migration inhibitor containing fluorine atoms, the insulation reliability of an organic thin film transistor can be improved without greatly reducing the mobility of the organic thin film transistor. That is, the inventors of the present invention found that the aforementioned object can be achieved by the following constitution.

(1) A composition for forming a gate insulating film containing an insulating material and a migration inhibitor selected from the group consisting of a compound represented by any of Formulae (1) to (8) which will be described later, a polymer compound (X) containing a repeating unit represented by Formula (A) which will be described later, and a polymer compound (Y) containing a repeating unit represented by Formula (B) which will be described later and a repeating unit represented by Formula (C) which will be described later.

The Formulae (Y-1) to (Y-8) are as follows.

P—(CR$_1$=Y)$_n$-Q      Formula (Y-1)

(In Formula (Y-1), each of P and Q independently represents OH, NR$_2$R$_3$, or CHR$_4$R$_5$; each of R$_2$ and R$_3$ independently represents a hydrogen atom or a group which can be substituted with a nitrogen atom; each of R$_4$ and R$_5$ independently represents a hydrogen atom or a substituent; Y represents CR$_6$ or a nitrogen atom; each of R$_1$ and R$_6$ independently represents a hydrogen atom or a substituent; at least two out of the groups represented by R$_1$, R$_2$, R$_3$, R$_4$, R$_5$, and R$_6$ may form a ring by being bonded to each other; n represents an integer of 0 to 5; when n is 0, P and Q do not represent CHR$_4$R$_5$ at the same time and do not represent OH at the same time; and when n represents a number of equal to or greater than 2, a plurality of atomic groups represented by (CR$_1$=Y) may be the same as or different from each other.)

R$_7$—C(=O)—H      Formula (Y-2)

(In Formula (Y-2), R$_7$ represents an alkyl group, an alkenyl group, an alkynyl group, an aryl group, a heterocyclic group, or a group which is obtained by combining these groups, and the group represented by R$_7$ may contain a hydroxy group or a group represented by —COO—.)

Formula (Y-3)

(In Formula (Y-3), each of R$_8$, R$_9$, and R$_{10}$ independently represents an alkyl group, an alkenyl group, an alkynyl group, an aryl group, a heterocyclic group, or a group which is obtained by combining these groups.)

Formula (Y-4)

(In Formula (Y-4), each of R$_{11}$ and R$_{12}$ independently represents an alkyl group, an alkenyl group, an alkynyl group, an aryl group, a heterocyclic group, or a group which is obtained by combining these groups, and R$_{11}$ and R$_{12}$ may form a ring by being bonded to each other.)

Z—SH      Formula (Y-5)

(In Formula (Y-5), Z represents an alkyl group, an alkenyl group, an alkynyl group, an aryl group, a heterocyclic group, or a group which is obtained by combining these groups, and the group represented by Z may contain a substituent.)

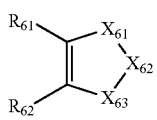

Formula (Y-6)

(In Formula (Y-6), each of $X_{61}$, $X_{62}$, and $X_{63}$ independently represents —NH—, —N=, =N—, —$CR_x$=, =$CR_x$—, or —S—; $R_x$ represents a hydrogen atom, —$NH_2$, or a linear or branched alkyl group having 1 to 15 carbon atoms; in the alkyl group, one carbon atom or two or more carbon atoms which are not adjacent to each other may be substituted with —O—, —S—, —$NR_0$—, —CO—, —CO—O—, —O—CO—, —O—CO—O—, —$CR_0$=$CR_{00}$—, or —C≡C—; in the alkyl group, one or more hydrogen atoms may be substituted with a fluorine atom, a chlorine atom, a bromine atom, an iodine atom, or —CN; each of $R_0$ and $R_{00}$ independently represents a hydrogen atom or a carbyl or hydrocarbyl group which may have a substituent and one or more heteroatoms; and at least one of $X_{61}$, $X_{62}$, and $X_{63}$ is not —$CR_x$= or =$CR_x$—.

Each of $R_{61}$ and $R_{62}$ independently represents a fluorine atom, a chlorine atom, -Sp-P, a linear or branched alkyl group having 1 to 15 carbon atoms, or an aryl group, a heteroaryl group, an aryloxy group, a heteroaryloxy group, an arylcarbonyl group, a heteroarylcarbonyl group, an arylcarbonyloxy group, a heteroarylcarbonyloxy group, an aryloxycarbonyl group, or a heteroaryloxycarbonyl group which has 2 to 30 carbon atoms and may have a substituent; in the alkyl group, one carbon atom or two or more carbon atoms which are not adjacent to each other may be substituted with —O—, —S—, —$NR_0$—, —CO—, —CO—O—, —O—CO—, —O—CO—O—, —$CR_0$=$CR_{00}$—, or —C≡C—; in the alkyl group, one or more hydrogen atoms may be substituted with a fluorine atom, a chlorine atom, a bromine atom, an iodine atom, or —CN; each of $R_0$ and $R_{00}$ independently represents a hydrogen atom or a carbyl or hydrocarbyl group which may have a substituent and one or more heteroatoms; Sp represents a single bond or a divalent organic group; P represents a polymerizable group or a cross-linking group; $R_{61}$ and $R_{62}$ may form an aromatic ring or an aromatic heterocyclic ring having 5 to 7 ring atoms by being bonded to each other; and the aromatic ring and the aromatic heterocyclic ring may have 1 to 6 substituents.)

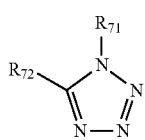

Formula (Y-7)

(In Formula (Y-7), each of $R_{71}$ and $R_{72}$ independently represents an alkyl group, an alkenyl group, an alkynyl group, an aryl group, a heterocyclic group, or a group which is obtained by combining these groups.)

Z1-S—S—Z2          Formula (Y-8)

(In Formula (Y-8), each of Z1 and Z2 independently represents an alkyl group, an alkenyl group, an alkynyl group, an aryl group, a heterocyclic group, or a group which is obtained by combining these groups, and at least one of Z1 and Z2 may contain a substituent.)

(2) The composition for forming a gate insulating film described in (1), in which a compound represented by Formula (6) which will be described later is a compound represented by Formula (22) which will be described later.

(3) The composition for forming a gate insulating film described in (1) or (2), in which a compound represented by Formula (8) which will be described later is a compound represented by Formula (23) which will be described later.

(4) The composition for forming a gate insulating film described in any one of (1) to (3), in which a compound represented by Formula (1) which will be described later is a compound represented by Formula (24) which will be described later.

(5) The composition for forming a gate insulating film described in any one of (1) to (3), in which the compound represented by Formula (1) which will be described later is at least one kind of compound selected from the group consisting of compounds represented by Formulae (31) to (46) which will be described later.

(6) The composition for forming a gate insulating film described in any one of (1) to (5), in which a compound represented by Formula (5) which will be described later is at least one kind of compound selected from the group consisting of compounds represented by Formulae (51) to (54) which will be described later.

(7) The composition for forming a gate insulating film described in (1), in which the migration inhibitor is the polymer compound (Y) containing the repeating unit represented by Formula (B) which will be described later and the repeating unit represented by Formula (C) which will be described later.

(8) The composition for forming a gate insulating film described in (7), in which in the repeating unit represented by Formula (B), B represents a monovalent group, which is formed as a result of removing one hydrogen atom (here, a hydrogen atom of a hydroxyl group is excluded) from a compound represented by Formula (Y-1) or a compound represented by Formula (Y-6), or a group represented by Formula (25).

(9) The composition for forming a gate insulating film described in (1), in which the migration inhibitor is at least one kind of compound selected from the group consisting of a compound represented by Formula (X1) which will be described later, a compound represented by Formula (33) which will be described later, a compound represented by Formula (2) which will be described later, a compound represented by Formula (3) which will be described later, a compound represented by Formula (4A) which will be described later, a compound represented by Formula (Y) which will be described later, a compound represented by Formula (22) which will be described later, a compound represented by Formula (7A) which will be described later, and a compound represented by Formula (23) which will be described later.

(10) The composition for forming a gate insulating film described in (1), in which the migration inhibitor is the polymer compound (X) containing the repeating unit represented by Formula (A) which will be described later.

(11) The composition for forming a gate insulating film described in (10), in which in the repeating unit represented by Formula (A), A represents a monovalent group which is formed as a result of removing one hydrogen atom (here, a hydrogen atom of a hydroxyl group is excluded) from the compound represented by Formula (X1) which will be described later, or a monovalent group which is formed as a result of removing one fluorine atom from the compound represented by Formula (X1), which will be described later, and having two or more fluorine atoms in a molecule.

(12) An organic thin film transistor prepared by using the composition for forming a gate insulating film described in any one of (1) to (11).

(13) Electronic paper using the organic thin film transistor described in (12).

(14) A display device using the organic thin film transistor described in (12).

As will be described later, according to the present invention, it is possible to provide a composition for forming a gate insulating film, which improves the insulation reliability of an organic thin film transistor without greatly reducing the mobility of the organic thin film transistor, and an organic thin film transistor which is prepared by using the composition for forming a gate insulating film.

BRIEF DESCRIPTION OF THE DRAWINGS

FIG. 1 is a schematic cross-sectional view showing an embodiment of the organic thin film transistor of the present invention.

DESCRIPTION OF THE PREFERRED EMBODIMENTS

Hereinafter, preferred embodiments of the composition for forming a gate insulating film and the organic thin film transistor of the present invention will be specifically described.

First, the present invention is characterized in that it uses a predetermined migration inhibitor containing fluorine atoms (hereinafter, referred to as an F-containing migration inhibitor).

Hereinafter, by using FIG. 1, the mechanism of the present invention will be specifically described. In FIG. 1, a case of a bottom contact-type (bottom contact-bottom gate type) organic thin film transistor is specifically described.

In FIG. 1, an organic thin film transistor 100 includes a substrate 10, a gate electrode 20, a gate insulating film 30, a source electrode 40, a drain electrode 42, an organic semiconductor layer 50, and a sealing layer 60.

When voltage is applied to the organic thin film transistor 100, due to the action of an electric field, the metal in either or both of the source electrode 40 and the drain electrode 42 is ionized. As a result, migration of metal ions occurs between the source electrode 40 and the drain electrode 42. Consequently, the insulating properties between the source electrode 40 and the drain electrode 42 deteriorate. Particularly, it is considered that the ion migration markedly occurs in the vicinity of the interface between the gate insulating film 30 and the organic semiconductor layer 50 that is positioned between the source electrode 40 and the drain electrode 42.

As described above, the composition for forming a gate insulating film of the present invention contains the F-containing migration inhibitor. The F-containing migration inhibitor contained in the gate insulating film 30 has low surface energy. Accordingly, the F-containing migration inhibitor moves to the vicinity of the surface of the organic semiconductor layer 50. That is, the F-containing migration inhibitor is localized in the vicinity of the interface between the gate insulating film 30 and the organic semiconductor layer 50 that is positioned between the source electrode 40 and the drain electrode 42. By causing the F-containing migration inhibitor to be localized as above, it is possible to efficiently inhibit the metal ions, which are educed from the source electrode 40 and the drain electrode 42, from diffusing in the vicinity of the interface between the gate insulating film 30 and the organic semiconductor layer 50. As a result, the resistance to the migration that occurs when an organic TFT having microelectrodes is prepared is improved. Furthermore, it is possible to reduce the amount of impurities which reduce the mobility inside the organic semiconductor layer. Consequently, it is possible to accomplish excellent performance without impairing the mobility.

Hereinafter, each of the components contained in the composition for forming a gate insulating film of the present invention will be described.

<Insulating Material>

The insulating material just needs to have insulating properties and may be an inorganic insulating material or an organic insulating material. However, considering the adhesiveness with respect to the organic semiconductor layer, an organic insulating material is preferably used.

The organic insulating material is not particularly limited, but is preferably a polymeric organic insulating material (insulating resin). A gate insulating film constituted with such a material can be easily formed and can improve the adhesiveness with respect to the organic semiconductor layer.

Examples of such an insulating resin include an olefin-based resin such as polyethylene, polypropylene, polyisobutylene, or polybutene, an acrylic resin such as polystyrene, polyimide, polyamide-imide, polyvinylphenylene, polycarbonate (PC), or polymethyl methacrylate (PMMA), a fluorine-based resin such as polytetrafluoroethylene (PTFE), a phenol-based resin such as polyvinylphenol (PVP) or a novolac resin, and the like. One kind of these can be used singly, or two or more kinds thereof can be used in combination.

Among these insulating resins, an insulating resin constituted with a monomer component which mainly has one or less unshared electron pair is preferably selected, and an insulating resin constituted with a monomer component which does not have an unshared electron pair is more preferably selected. By selecting such an insulating resin having low polarity, the transmission (diffusion) of metal ions resulting from an insulating resin can be preferably prevented or inhibited.

Specifically, examples of the insulating resin constituted with a monomer component having one or less unshared electron pair, that is, examples of the insulating polymer containing a monomer having one or less unshared electron pair include polyolefin, polystyrene, and the like which are constituted with a linear aliphatic hydrocarbon such as polyethylene, polypropylene, polyisobutylene, or polybutene. The examples also include a polyolefin having cyclic aliphatic hydrocarbon (hereinafter, simply referred to as a "cycloolefin-containing polymer"). Among these, the cycloolefin-containing polymer is preferable because it is excellent in characteristics such as high pressure resistance, low hygroscopicity, high heat resistance, high density, and solvent selectivity. Furthermore, the polymer is preferable because it has a rigid main chain and a high glass transition temperature.

As the cyclic aliphatic hydrocarbon contained in the cycloolefin-containing polymer, cyclic aliphatic hydrocarbon having 3 to 20 carbon atoms is preferably selected, and cyclic aliphatic hydrocarbon having 4 to 15 carbon atoms is more preferably selected. Specifically, examples thereof include cyclopentane, cyclohexane, cycloheptane, cyclodecane, norbornene, dicyclopentadiene, tetracyclododecene, and the like. One kind of these compounds can be used singly, or two or more kinds thereof can be used in combination. The cycloolefin-containing polymer particularly preferably contains norbornene. Having a bulky molecular structure, norbornene can easily make a polyolefin have an amorphous structure by using steric hindrance. Therefore, a uniform gate insulating film can be obtained.

<F-Containing Migration Inhibitor>

The F-containing migration inhibitor (F-containing antimigration agent) contained in the composition of the present invention is a compound selected from the group consisting of a compound represented by any of the following Formulae (1) to (8), a polymer compound (X) containing a repeating unit represented by the following Formula (A), and a polymer compound (Y) containing a repeating unit represented by the following Formula (B) and a repeating unit represented by the following Formula (C). The F-containing migration inhibitor is a compound which contains fluorine atoms and inhibits the migration of metal ions.

The content of fluorine atoms (fluorine content) in the F-containing migration inhibitor is not particularly limited and can be appropriately adjusted according to the type of the insulating material used or the like. However, in view of lowering the surface energy and causing more of the F-containing migration inhibitor to be localized in the vicinity of the exposed surface of the gate insulating film such that the mobility of the organic semiconductor is not impaired, the fluorine content is preferably equal to or greater than 2% by mass and less than 65% by mass, more preferably 5% by mass to 60% by mass, and even more preferably 10% by mass to 50% by mass. Herein, the fluorine content is a value expressed by a ratio (content) of mass of fluorine atoms to the total molecular weight of the migration inhibitor. That is, the fluorine content is a value expressed by {(number of fluorine atoms in compound)×(atomic weight of fluorine)/(total molecular weight of compound)}×100(%). For example, provided that the migration inhibitor has a total molecular weight of 100 and contains 3 fluorine atoms, the mass ratio (%) of the fluorine atoms to the total molecular weight is 57% by mass which is calculated by {(19×3)/100}×100.

Hereinafter, the F-containing migration inhibitor will be specifically described.

In the present specification, an alkyl group may contain a linking group such as —CO—, —NH—, —O—, —S—, or a group which is obtained by combining these.

(Compound Represented by Formula (1))

First, a compound represented by Formula (1) will be described.

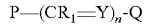  Formula (1)

P—(CR$_1$=Y)$_n$-Q

In Formula (1), each of P and Q independently represents OH, NR$_2$R$_3$, or CHR$_4$R$_5$. Y represents CR$_6$ or a nitrogen atom. n represents an integer of 0 to 5. Here, when n is 0, P and Q do not represent CHR$_4$R$_5$ at the same time and do not represents OH at the same time. When n is a number of equal to or greater than 2, a plurality of atomic groups represented by (CR$_1$=Y) may be the same as or different from each other.

Each of R$_2$ and R$_3$ independently represents a hydrogen atom or a group which can be substituted with a nitrogen atom.

The group which can be substituted with a nitrogen atom is not particularly limited as long as it can be substituted with a nitrogen atom. Examples of such a group include an alkyl group (including a cycloalkyl group), an alkenyl group (including a cycloalkenyl group and a bicycloalkenyl group), an alkynyl group, an aryl group, a heterocyclic group, alkyl and aryl sulfinyl groups, alkyl and aryl sulfonyl groups, an acyl group, an alkoxycarbonyl group, an aryloxycarbonyl group, a carbamoyl group, a phosphino group, a phosphinyl group, a group which is obtained by combining these, and the like.

More specifically, preferred examples of such a group include an alkyl group [the alkyl group represents a substituted or unsubstituted linear, branched, or cyclic alkyl group; these also include an alkyl group (preferably an alkyl group having 1 to 50 carbon atoms, for example, methyl, ethyl, n-propyl, isopropyl, t-butyl, n-octyl, eicosyl, 2-chloroethyl, 2-cyanoethyl, or 2-ethylhexyl), a cycloalkyl group (preferably a substituted or unsubstituted cycloalkyl group having 3 to 30 carbon atoms, for example, cyclohexyl, cyclopentyl, or 4-n-dodecylcyclohexyl), a bicycloalkyl group (preferably a substituted or unsubstituted bicycloalkyl group having 5 to 30 carbon atoms, that is, a monovalent group formed as a result of removing one hydrogen atom from bicycloalkane having 5 to 30 carbon atoms, for example, bicyclo[1.2.2]pentan-2-yl or bicyclo[2.2.2]octan-3-yl), a tricyclo structure having a large number of cyclic structures, and the like; an alkyl group (for example, an alkyl group in an alkylthio group) in a substituent which will be described below also represents the alkyl group having the concept described above], an alkenyl group [a substituted or unsubstituted linear, branched, or cyclic alkenyl group; these include an alkenyl group (preferably a substituted or unsubstituted alkenyl group having 2 to 30 carbon atoms, for example, vinyl, allyl, prenyl, geranyl, or oleyl), a cycloalkenyl group (preferably a substituted or unsubstituted cycloalkenyl group having 3 to 30 carbon atoms, that is, a monovalent group formed as a result of removing one hydrogen atom of cycloalkene having 3 to 30 carbon atoms, for example, 2-cyclopenten-1-yl or 2-cyclohexen-1-yl), and a bicycloalkenyl group (a substituted or unsubstituted bicycloalkenyl group, preferably, a substituted or unsubstituted bicycloalkenyl group having 5 to 30 carbon atoms, that is, a monovalent group formed as a result of removing one hydrogen atom of bicycloalkene having one double bond, for example, bicyclo[2.2.1]hept-2-en-1-yl or bicyclo[2.2.2]oct-2-en-4-yl)], an alkynyl group (preferably a substituted or unsubstituted alkynyl group having 2 to 30 carbon atoms, for example, ethynyl, propargyl, or a trimethylsilylethynyl group), an aryl group (preferably a substituted or unsubstituted aryl group having 6 to 30 carbon atoms, for example, phenyl, p-tolyl, naphthyl, m-chlorophenyl, or o-hexadecanoylaminophenyl), a heterocyclic group (preferably a monovalent group which is formed as a result of removing one hydrogen atom from a 5-membered or 6-membered substituted or unsubstituted aromatic or non-aromatic heterocyclic compound, more preferably, a 5-membered or 6-membered aromatic heterocyclic group having 3 to 30 carbon atoms, for example, 2-furanyl, 2-thienyl, 2-pyrimidinyl, or 2-benzothiazolinyl), alkyl and aryl sulfinyl groups (preferably a substituted or unsubstituted alkyl sulfinyl group having 1 to 30 carbon atoms and a substituted or unsubstituted aryl sulfinyl group having 6 to 30 carbon atoms, for example, methyl sulfinyl, ethyl sulfinyl, phenyl sulfinyl, and p-methylphenyl sulfinyl), alkyl and aryl sulfonyl groups (preferably a substituted or unsubstituted alkyl sulfonyl group having 1 to 30 carbon atoms and a substituted or unsubstituted aryl sulfonyl group having 6 to 30 carbon atoms, for example, methyl sulfonyl, ethyl sulfonyl, phenyl sulfonyl, and p-methylphenyl sulfonyl), an acyl group (preferably a formyl group, a substituted or unsubstituted alkyl carbonyl group having 2 to 30 carbon atoms, a substituted or unsubstituted aryl carbonyl group having 7 to 30 carbon atoms, or a substituted or unsubstituted heterocyclic carbonyl group having 4 to 30 carbon atoms that is bonded to a carbonyl group through carbon atoms, for example, acetyl, pivaloyl, 2-chloroacetyl, stearoyl, benzoyl, p-n-octyloxyphenyl carbonyl, 2-pyridyl carbonyl, or 2-furyl carbonyl), an aryloxycarbonyl group (preferably a substituted or unsubstituted aryloxycarbonyl group having 7 to 30 carbon atoms, for example, phenoxycarbonyl, o-chlorophenoxycarbonyl, m-nitrophenoxycarbonyl, or p-t-butylphenoxycarbonyl), an alkoxycarbonyl group (preferably a substituted or unsubstituted alkoxycarbonyl group having 2 to 30 carbon atoms, for example, methoxycarbonyl, ethoxycarbonyl, t-butoxycarbonyl, or n-octadecyloxycarbonyl), a carbamoyl group (preferably substituted or unsubstituted carbamoyl having 1 to 30 carbon atoms, for example, carbamoyl, N-methyl carbamoyl, N,N-dimethyl carbamoyl, N,N-di-n-octyl carbamoyl, or N-(methylsulfonyl)carbamoyl), a phosphino group (preferably a substituted or unsubstituted phosphino group having 2 to 30 carbon atoms, for example, dimethylphosphino, diphenylphosphino, or methylphenoxyphosphino), and a phosphinyl group (preferably a substituted or unsubstituted phosphinyl group having 2 to 30 carbon atoms, for example, phosphinyl, dioctyloxyphosphinyl, or diethoxyphosphinyl).

Among the aforementioned functional groups, those having a hydrogen atom may be further substituted after the hydrogen atom is removed.

The alkyl group represented by $R_2$ and $R_3$ represents a substituted or unsubstituted linear, branched, or cyclic alkyl group. The alkyl group preferably has 1 to 50 carbon atoms, more preferably has 1 to 30 carbon atoms, and particularly preferably has 1 to 20 carbon atoms.

Preferred examples of the alkyl group include methyl, ethyl, n-propyl, isopropyl, cyclopropyl, butyl, isobutyl, t-butyl, sec-butyl, pentyl, isopentyl, neopentyl, t-pentyl, hexyl, cyclohexyl, heptyl, cyclopentyl, octyl, 2-ethylhexyl, nonyl, decyl, dodecyl, tetradecyl, hexadecyl, octadecyl, eicosyl, docosyl, triacontyl, and the like. Among these, methyl, ethyl, n-propyl, isopropyl, butyl, isobutyl, t-butyl, sec-butyl, pentyl, isopentyl, neopentyl, hexyl, cyclohexyl, octyl, 2-ethylhexyl, dodecyl, hexadecyl, and octadecyl are more preferable, and methyl, ethyl, n-propyl, isopropyl, butyl, t-butyl, pentyl, isopentyl, hexyl, cyclohexyl, octyl, 2-ethylhexyl, dodecyl, hexadecyl, and octadecyl are particularly preferable.

The alkyl group may contain a linking group such as —CO—, —NH—, —O—, —S—, or a group which is obtained by combining these. When the alkyl group contains such a linking group, the position of the linking group is not particularly limited, and the linking group may be positioned at the terminal of the alkyl group. For example, the alkyl group may be in the form of —S—$R_x$ ($R_x$: alkyl group).

The alkyl group represented by $R_2$ and $R_3$ may further have a substituent.

Examples of the substituent include the halogen atom, an alkyl group (including a cycloalkyl group), an alkenyl group (including a cycloalkenyl group and a bicycloalkenyl group), an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an alkoxycarbonyloxy group, aryloxycarbonyloxy, an amino group (including an anilino group), an acylamino group, an aminocarbonylamino group, an alkoxycarbonylamino group, an aryloxycarbonylamino group, a sulfamoylamino group, alkyl and aryl sulfonylamino groups, a mercapto group, an alkylthio group, an arylthio group, a heterocyclic thio group, a sulfamoyl group, a sulfo group, alkyl and aryl sulfinyl groups, alkyl and aryl sulfonyl groups, an acyl group, an aryloxycarbonyl group, an alkoxycarbonyl group, a carbamoyl group, aryl and heterocyclic azo groups, an imide group, a phosphino group, a phosphinyl group, a phosphinyloxy group, a phosphinylamino group, a silyl group, and a combination of these.

More specifically, the substituent represents a halogen atom (for example, a chlorine atom, a bromine atom, or an iodine atom), an alkyl group [the alkyl group represents a substituted or unsubstituted linear, branched, or cyclic alkyl group; these also include an alkyl group (preferably an alkyl group having 1 to 30 carbon atoms, for example, methyl, ethyl, n-propyl, isopropyl, t-butyl, n-octyl, eicosyl, 2-chloroethyl, 2-cyanoethyl, or 2-ethylhexyl), a cycloalkyl group (preferably a substituted or unsubstituted cycloalkyl group having 3 to 30 carbon atoms, for example, cyclohexyl, cyclopentyl, or 4-n-dodecylcyclohexyl), a bicycloalkyl group (preferably a substituted or unsubstituted bicycloalkyl group having 5 to 30 carbon atoms, that is, a monovalent group formed as a result of removing one hydrogen atom from bicycloalkane having 5 to 30 carbon atoms, for example, bicyclo[1.2.2]heptan-2-yl or bicyclo[2.2.2]octan-3-yl), a tricyclo structure having a large number of cyclic structures, and the like; the alkyl group may contain a linking group such as —CO—, —NH—, —O—, —S—, or a group which is obtained by combining these; an alkyl group (for example, an alkyl group in an alkylthio group) in a substituent which will be described below also represents the alkyl group having the concept described above], an alkenyl group [the alkenyl group represents a substituted or unsubstituted linear, branched, or cyclic alkenyl group; these include an alkenyl group (preferably a substituted or unsubstituted alkenyl group having 2 to 30 carbon atoms, for example, vinyl, allyl, prenyl, geranyl, or oleyl), a cycloalkenyl group (preferably a substituted or unsubstituted cycloalkenyl group having 3 to 30 carbon atoms, that is, a monovalent group formed as a result of removing one hydrogen atom of cycloalkene having 3 to 30 carbon atoms, for example, 2-cyclopenten-1-yl or 2-cyclohexen-1-yl), and a bicycloalkenyl group (a substituted or unsubstituted bicycloalkenyl group, preferably, a substituted or unsubstituted bicycloalkenyl group having 5 to 30 carbon atoms, that is, a monovalent group formed as a result of removing one hydrogen atom of bicycloalkene having one double bond, for example, bicyclo[2.2.1]hept-2-en-1-yl or bicyclo[2.2.2]oct-2-en-4-yl)], an alkynyl group (preferably a substituted or unsubstituted alkynyl group having 2 to 30 carbon atoms, for example, ethynyl, propargyl, or a trimethylsilyl ethynyl group), an aryl group (preferably a substituted or unsubstituted aryl group having 6 to 30 carbon atoms, for example, phenyl, p-tolyl, naphthyl, m-chlorophenyl, or o-hexadecanoylaminophenyl), a heterocyclic group (preferably a monovalent group which is formed as a result of removing one hydrogen atom from a 5-membered or 6-membered substituted or unsubstituted aromatic or non-aromatic heterocyclic compound, more preferably, a 5-membered or 6-membered aromatic heterocyclic group having 3 to 30 carbon atoms, for example, 2-furanyl, 2-thienyl, 2-pyrimidinyl, or 2-benzothiazolinyl), a cyano group, a hydroxyl group, a nitro group, a carboxyl group, an alkoxy group (preferably a substituted or unsubstituted alkoxy group having 1 to 30 carbon atoms, for example, methoxy, ethoxy, isopropoxy, t-butoxy, n-octyloxy, or 2-methoxyethoxy), an aryloxy group (preferably a substituted or unsubstituted aryloxy group having 6 to 30 carbon atoms, for example, phenoxy, 2-methylphenoxy, 4-t-butylphenoxy, 3-nitrophenoxy, or 2-tetradecanoylaminophenoxy), a silyloxy group (preferably a silyloxy group having 3 to 20 carbon atoms, for example, trimethylsilyloxy or t-butyldimethylsilyloxy), a heterocyclic oxy group (preferably a substituted or unsubstituted heterocyclic oxy group having 2 to 30 carbon atoms, for example, 1-phenyltetrazol-5-oxy or 2-tetrahydropyranyloxy), an acyloxy group (preferably a formyloxy group, a substituted or unsubstituted alkylcarbonyloxy group having 2 to 30 carbon atoms, or a substituted or unsubstituted arylcarbonyloxy group having 6 to 30 carbon atoms, for example, formyloxy, acetyloxy, pivaloyloxy, stearoyloxy, benzoyloxy, or p-methoxyphenylcarbonyloxy), a carbamoyloxy group (preferably substituted or unsubstituted carbamoyloxy having 1 to 30 carbon atoms, for example, N,N-dimethylcarbamoyloxy, N,N-diethylcarbamoyloxy, morpholinocarbonyloxy, N,N-di-n-octylaminocarbonyloxy, or N-n-octylcarbamoyloxy), an alkoxycarbonyloxy group (preferably a substituted or unsubstituted alkoxycarbonyloxy group having 2 to 30 carbon atoms, for example, methoxycarbonyloxy, ethoxycarbonyloxy, t-butoxycarbonyloxy, or n-octylcarbonyloxy), an aryloxycarbonyloxy group (preferably a substituted or unsubstituted aryloxycarbonyloxy group having 7 to 30 carbon atoms, for example, phenoxycarbonyloxy, p-methoxyphenoxycarbonyloxy, or p-n-hexadecyloxyphenoxycarbonyloxy), an amino group (preferably an amino group, a substituted or unsubstituted alkylamino group having 1 to 30 carbon atoms, or a substituted or unsubstituted anilino group having 6 to 30 carbon atoms, for example, amino, methylamino, dimethylamino, anilino, N-methyl-anilino, or diphenylamino), an acylamino group (preferably a formylamino group, a substituted or unsubstituted alkylcarbonylamino group having 1 to 30 carbon atoms, or a substituted or unsubstituted arylcarbonylamino group having 6 to 30 carbon atoms, for example, formylamino, acetylamino, pivaloylamino, lauroylamino, benzoyl amino, 3,4,5-tri-n-octyloxyphenylcarbonylamino), an aminocarbonylamino group (preferably substituted or unsubstituted aminocarbonylamino having 1 to 30 carbon atoms, for example, carbamoylamino, N,N-dimethylaminocarbonylamino, N,N-diethylaminocarbonylamino, or morpholinocarbonylamino), an alkoxycarbonylamino group (preferably a substituted or unsubstituted alkoxycarbonylamino group having 2 to 30 carbon atoms, for example, methoxycarbonylamino, ethoxycarbonylamino, t-butoxycarbonylamino, n-octadecyloxycarbonylamino, or N-methyl-methoxycarbonylamino), an aryloxycarbonylamino group (preferably a substituted or unsubstituted aryloxycarbonylamino group having 7 to 30 carbon atoms, for example, phenoxycarbonylamino, p-chlorophenoxycarbonylamino, or m-n-octyloxyphenoxycarbonylamino), a sulfamoylamino group (preferably a substituted or unsubstituted sulfamoylamino group having 0 to 30 carbon atoms, for example, sulfamoylamino, N,N-dimethylaminosulfonylamino, or N-n-octylaminosulfonylamino), alkyl and aryl sulfonylamino groups (preferably substituted or unsubstituted alkylsulfonylamino having 1 to 30 carbon atoms and substituted or unsubstituted arylsulfonylamino having 6 to 30 carbon atoms, for example, methylsulfonylamino, butylsulfonyl amino, phenyl sulfonylamino, 2,3, 5-trichlorophenylsulfonylamino, or p-methylphenylsulfonylamino), a mercapto group, an alkylthio group (preferably a substituted or unsubstituted alkylthio group having 1 to 30 carbon atoms, for example, methylthio, ethylthio, or n-hexadecylthio), an arylthio group (preferably substituted or unsubstituted arytho having 6 to 30 carbon atoms, for example, phenylthio, p-chlorophenylthio, or m-methoxyphenylthio), a heterocyclic thio group (preferably a substituted or unsubstituted heterocyclic thio group having 2 to 30 carbon atoms, for example, 2-benzothiazolylthio or 1-phenyltetrazol-5-ylthio), a sulfamoyl group (preferably a substituted or unsubstituted sulfamoyl group having 0 to 30 carbon atoms, for example, N-ethylsulfamoyl, N-(3-dodecyloxypropyl)sulfamoyl, N,N-dimethylsulfamoyl, N-acetylsulfamoyl, N-benzoylsulfamoyl, or N—(N'-phenylcarbamoyesulfamoyl), a sulfo group, alkyl and aryl sulfinyl groups (preferably a substituted or unsubstituted alkylsulfinyl group having 1 to 30 carbon atoms and a substituted or unsubstituted arylsulfinyl group having 6 to 30 carbon atoms, for example, methylsulfinyl, ethylsulfinyl, phenylsulfinyl, or p-methylphenylsulfinyl), alkyl and aryl sulfonyl groups (preferably a substituted or unsubstituted alkylsulfonyl group having 1 to 30 carbon atoms and a substituted or unsubstituted arylsulfonyl group having 6 to 30 carbon atoms, for example, methylsulfonyl, ethylsulfonyl, phenylsulfonyl, and p-methylphenylsulfonyl), an acyl group (preferably a formyl group, a substituted or unsubstituted alkylcarbonyl group having 2 to 30 carbon atoms, a substituted or unsubstituted arylcarbonyl group having 7 to 30 carbon atoms, or a substituted or unsubstituted heterocyclic carbonyl group having 4 to 30 carbon atoms that is bonded to a carbonyl group through carbon atoms, for example, acetyl, pivaloyl, 2-chloroacetyl, stearoyl, benzoyl, p-n-octyloxyphenylcarbonyl, 2-pyridylcarbonyl, or 2-furylcarbonyl), an aryloxycarbonyl group (preferably a substituted or unsubstituted aryloxycarbonyl group having 7 to 30 carbon atoms, for example, phenoxycarbonyl, o-chlorophenoxycarbonyl, m-nitrophenoxycarbonyl, or p-t-butylphenoxycarbonyl), an alkoxycarbonyl group (preferably a substituted or unsubstituted alkoxycarbonyl group having 2 to 30 carbon atoms, for example, methoxycarbonyl, ethoxycarbonyl, t-butoxycarbonyl, or n-octadecyloxycarbonyl), a carbamoyl group (preferably substituted or unsubstituted carbamoyl having 1 to 30 carbon atoms, for example, carbamoyl, N-methylcarbamoyl, N,N-dimethylcarbamoyl, N,N-di-n-octylcarbamoyl, or N-(methylsulfonyl)carbamoyl), aryl and heterocyclic azo groups (preferably a substituted or unsubstituted arylazo group having 6 to 30 carbon atoms and a substituted or unsubstituted heterocyclic azo group having 3 to 30 carbon atoms, for example, phenylazo, p-chlorophenylazo, and 5-ethylthio-1,3,4-thiadiazol-2-ylazo), an imide group (preferably N-succinimide or N-phthalimide), a phosphino group (preferably a substituted or unsubstituted phosphino group having 2 to 30 carbon atoms, for example, dimethylphosphino, diphenylphosphino, or methylphenoxyphosphino), a phosphinyl group (preferably a substituted or unsubstituted phosphinyl group having 2 to 30 carbon atoms, for example, phosphinyl, dioctyloxyphosphinyl, or diethoxyphosphinyl), a phosphinyloxy group (preferably a substituted or unsubstituted phosphinyloxy group having 2 to 30 carbon atoms, for example, diphenoxyphosphinyloxy or dioctyloxyphosphinyloxy), a phosphinylamino group (preferably a substituted or unsubstituted phosphinylamino group having 2 to 30 carbon atoms, for example, dimethoxyphosphinylamino or dimethylaminophosphinylamino), or a silyl group (preferably a substituted or unsubstituted silyl group having 3 to 30 carbon atoms, for example, trimethylsilyl, t-butyldimethylsilyl, or phenyldimethylsilyl).

Among the aforementioned functional groups, those having a hydrogen atom may be further substituted with the aforementioned groups after the hydrogen atom is removed. Examples of such functional groups include an alkylcarbonylaminosulfonyl group, an arylcarbonylaminosulfonyl group, an alkylsulfonylaminocarbonyl group, an arylsulfonylaminocarbonyl group, and the like. Examples of these functional groups include methylsulfonylaminocarbonyl, p-methylphenylsulfonylaminocarbonyl, acetylaminosulfonyl, a benzoylaminosulfonyl group, and the like.

The alkenyl group represented by $R_2$ and $R_3$ represents a substituted or unsubstituted linear, branched, or cyclic alkenyl group. Such an alkenyl group preferably has 2 to 50 carbon atoms, more preferably has 2 to 30 carbon atoms, and particularly preferably has 2 to 20 carbon atoms. Preferred examples of the alkenyl group include vinyl, allyl, prenyl, geranyl, oleyl, 2-cyclopenten-1-yl, 2-cyclohexen-1-yl, bicyclo[2.2.1]hept-2-en-1-yl, bicyclo[2.2.2]oct-2-en-4-yl, and the like. Among these, vinyl, allyl, prenyl, geranyl, oleyl, 2-cyclopenten-1-yl, and 2-cyclohexen-1-yl are more preferable.

The alkenyl group represented by $R_2$ and $R_3$ may further have a substituent. Examples of the substituent include the substituents of the alkyl group represented by $R_2$ and $R_3$ described above.

Just like the aforementioned alkyl group, the alkenyl group may contain a linking group such as —CO—, —NH—, —O—, —S—, or a group which is obtained by combining these.

The alkynyl group represented by $R_2$ and $R_3$ represents a substituted or unsubstituted linear, branched, or cyclic alkynyl group. The alkynyl group preferably has 2 to 50 carbon atoms, more preferably has 2 to 30 carbon atoms, and particularly preferably has 2 to 20 carbon atoms. Preferred examples of the alkynyl group include ethynyl, propargyl, and the like.

The alkynyl group represented by $R_2$ and $R_3$ may further have a substituent. Examples of the substituent include the substituents of the alkyl group represented by $R_2$ and $R_3$ described above.

Just like the aforementioned alkyl group, the alkynyl group may contain a linking group such as —CO—, —NH—, —O—, —S—, or a group which is obtained by combining these.

The aryl group represented by $R_2$ and $R_3$ represents a substituted or unsubstituted aryl group. The aryl group preferably has 6 to 50 carbon atoms, more preferably has 6 to 30 carbon atoms, and particularly preferably has 6 to 20 carbon atoms. Preferred examples of the aryl group include phenyl, 2-methylphenyl, 3-methylphenyl, 4-methylphenyl, 2-ethylphenyl, 4-ethylphenyl, 2,4-dimethylphenyl, 2,6-dimethylphenyl, 2,4,6-trimethylphenyl, 1-naphthyl, 2-naphthyl, 2-chlorophenyl, 3-chlorophenyl, 4-chlorophenyl, 2-methoxyphenyl, 3-methoxyphenyl, 4-methoxyphenyl, 2-benzylphenyl, 4-benzylphenyl, 2-methylcarbonylphenyl, 4-methylcarbonylphenyl, and the like.

Among these, phenyl, 2-methylphenyl, 4-methylphenyl, 2-ethylphenyl, 4-ethylphenyl, 2,4-dimethylphenyl, 2,6-dimethylphenyl, 2,4,6-trimethylphenyl, 1-naphthyl, 2-naphthyl, 2-chlorophenyl, 4-chlorophenyl, 2-methoxyphenyl, 3-methoxyphenyl, 4-methoxyphenyl, 2-benzylphenyl, 4-benzylphenyl, and the like are more preferable, and phenyl, 2-methylphenyl, 4-methylphenyl, 2,4-dimethylphenyl, 2,6-dimethylphenyl, 2,4,6-trimethylphenyl, 1-naphthyl, 2-naphthyl, 2-chlorophenyl, 4-chlorophenyl, 2-methoxyphenyl, 4-methoxyphenyl, 2-benzylphenyl, 4-benzylphenyl, and the like are particularly preferable.

The aryl group represented by $R_2$ and $R_3$ may further have a substituent. Examples of the substituent include the substituents of the alkyl group represented by $R_2$ and $R_3$ described above.

Each of $R_4$ and $R_5$ independently represents a hydrogen atom or a substituent.

Examples of the substituent represented by $R_4$ and $R_5$ include the substituents of the alkyl group (substituents that the alkyl group may have) represented by $R_2$ and $R_3$ described above. The substituent is preferably an alkyl group, an alkenyl group, an alkynyl group, an aryl group, or a group which is obtained by combining these. Preferred examples of each of these substituents include the groups exemplified as $R_2$ and $R_3$ described above.

The group represented by $R_4$ and $R_5$ may further have a substituent. Examples of the substituent include the substituents of the alkyl group represented by $R_2$ and $R_3$ described above.

Each of $R_1$ and $R_6$ independently represents a hydrogen atom or a substituent.

Examples of the substituent represented by $R_1$ and $R_6$ include the substituents of the alkyl group represented by $R_2$ and $R_3$ described above. The substituent is preferably an alkyl group, an alkenyl group, an alkynyl group, an aryl group, or a group which is obtained by combining these. Preferred examples of each of these substituents include the groups exemplified as $R_2$ and $R_3$ described above.

The group represented by $R_1$ and $R_6$ may further have a substituent. Examples of the substituent include the substituents of the alkyl group represented by $R_2$ and $R_3$ described above.

The compound represented by Formula (1) may be linear or cyclic. When the compound is cyclic, at least two out of the groups represented by $R_1$, $R_2$, $R_3$, $R_4$, $R_5$, or $R_6$ may form a ring by being bonded to each other.

When the two groups are bonded to each other, they may be bonded to each other through any of a single bond, a double bond, or a triple bond.

At least one of the groups represented by $R_1$ to $R_6$ contains a fluorine atom. The fluorine atom may be substituted with any carbon atom of the compound represented by Formula (1). Herein, it is preferable that in at least one of the groups represented by $R_1$ to $R_6$, a portion of hydrogen atoms or the entirety of hydrogen atoms (preferably a portion of hydrogen atoms or the entirety of hydrogen atoms bonded to carbon atoms) are substituted with a fluorine atom. Particularly, it is preferable that the fluorine atom is contained in at least one of the groups represented by $R_1$ to $R_6$, as a fluoroalkyl group (hereinafter, referred to as an $R_f$ group) or a group substituted with the $R_f$ group. That is, it is preferable that at least one of the groups represented by $R_1$ to $R_6$ contains a fluoroalkyl group (preferably, a perfluoroalkyl group). Herein, it is preferable that the fluorine content of the compound represented by Formula (1) satisfies the range described above.

The fluoroalkyl group is an alkyl group in which a potion of hydrogen atoms or the entirety of hydrogen atoms are substituted with a fluorine atom. The perfluoroalkyl group is an alkyl group in which the entirety of hydrogen atoms are substituted with fluorine atom.

The $R_f$ group is preferably a linear or branched perfluoroalkyl group having 1 to 14 carbon atoms (preferably having 1 to 10 carbon atoms and more preferably having 1 to 7 carbon atoms) or a substituent having 2 to 20 carbon atoms that is substituted with a linear or branched perfluoroalkyl group having 1 to 14 carbon atoms.

Examples of the linear or branched perfluoroalkyl group having 1 to 14 carbon atoms include $CF_3$—, $C_2F_5$—, $C_3F_7$—, $C_4F_9$—, $C_5F_{11}$—, $(CF_3)_2$—CF—$(CF_2)_2$—, $C_6F_{13}$—, $C_7F_{15}$—, $(CF_3)_2$—CF—$(CF_2)_4$—, $C_8F_{17}$—, $C_9F_{19}$—, $C_{10}F_{21}$—, $C_{12}F_{25}$—, and $C_{14}F_{29}$—.

Examples of the substituent having 2 to 20 carbon atoms that is substituted with a perfluoroalkyl group having 1 to 14 carbon atoms include $(CF_3)_2CF(CF_2)_4(CH_2)_2$—, $C_9F_{19}CH_2$—, $C_8F_{17}CH_2CH(OH)CH_2$—, $C_8F_{17}CH_2CH(OH)CH_2OC$—$OCH_2$—, $(CF_3)_2CF(CF_2)_4(CH_2)_2OC$—$OCH_2$—, $C_8F_{17}CH_2CH(OH)CH_2OC=O(CH_2)_2$—, $(CF_3)_2CF(CF_2)_4(CH_2)_2OC=O(CH_2)_2$—, $(CF_3)_2CFOC_2F_4$—, $CF_3CF_2CF_2O[CF(CF_3)CF_2O]_4$—$CF(CF_3)$—, and the like, but the present invention is not limited to these.

It is preferable that at least one of the groups represented by $R_1$ to $R_6$ contains 1 to 4 $R_f$ groups in a single molecule.

Herein, two or more kinds of the compound represented by Formula (1) may be used.

The compound represented by Formula (1) is preferably a compound represented by the following Formula (24). The compound represented by Formula (24) preferably contains a fluorine atom, and the fluorine content in the compound represented by Formula (24) preferably satisfies the range described above.

Conceptually, the compound represented by Formula (24) corresponds to a compound subordinate to the compound represented by Formula (36) which will be described later. Specifically, $R_{241}$ described below corresponds to $CHR_{361}R_{362}$ in Formula (36), and $R_{242}$ to $R_{244}$ and $Rf_1(X_1)(F)C$-$L_1$-$Y_1$-$L_2$-$Z_1$-$L_3$- corresponds to $V_{36}$ in Formula (36).

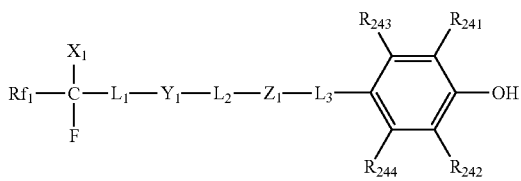

Formula (24)

In Formula (24) each of $R_{241}$ and $R_{242}$ independently represents an alkyl group having 1 to 12 carbon atoms. Because the migration inhibition ability is further improved, the alkyl group is preferably an alkyl group having 1 to 8 carbon atoms, more preferably an alkyl group having 1 to 6 carbon atoms, and particularly preferably an alkyl group having 1 to 5 carbon atoms. Preferred examples of the alkyl group specifically include methyl, ethyl, n-propyl, isopropyl, t-butyl, isobutyl, 2,2-dimethylpropyl, hexyl, cyclohexyl, and the like.

In Formula (24), each of $R_{243}$ and $R_{244}$ independently represents a hydrogen atom or a substituent. Specific examples and preferred embodiments of the substituent are the same as those of the substituents of the alkyl group represented by $R_2$ and $R_3$ described above.

In Formula (24), $R_{f1}$ represents a fluoroalkyl group having 22 or less carbon atoms that may have an ethereal oxygen atom, in which at least one hydrogen atom is substituted with a fluorine atom. Alternatively, $R_{f1}$ represents a fluorine atom.

The hydrogen atom in the perfluoroalkyl group may be substituted with a halogen atom other than a fluorine atom. As the halogen atom other than a fluorine atom, a chlorine atom is preferable. Furthermore, the ethereal oxygen atom (—O—) may be present between carbon-carbon bonds of the fluoroalkyl group or may be present at the terminal of the fluoroalkyl group. Examples of the structure of the fluoroalkyl group include a linear structure, a branched structure, a cyclic structure, and a structure that partially has a ring. Among these, a linear structure is preferable.

$R_{f1}$ is preferably a perfluoroalkyl group or a perfluoroalkyl group containing one hydrogen atom, and particularly preferably a perfluoroalkyl group (here, the perfluoroalkyl group includes a perfluoroalkyl group having an ethereal oxygen atom).

$R_{f1}$ is preferably a perfluoroalkyl group having 4 to 6 carbon atoms or a perfluoroalkyl group having 4 to 9 carbon atoms that has an ethereal oxygen atom.

Specific examples of $R_{f1}$ includes —$CF_3$, —$CF_2CF_3$, —$CF_2CHF_2$, —$(CF_2)_2CF_3$, —$(CF_2)_3CF_3$, —$(CF_2)_4CF_3$, —$(CF_2)_5CF_3$, —$(CF_2)_6CF_3$, —$(CF_2)_7CF_3$, —$(CF_2)_8CF_3$, —$(CF_2)_9CF_3$, —$(CF_2)_{11}CF_3$, —$(CF_2)_{15}CF_3$, —$CF(CF_3)O(CF_2)_5CF_3$, —$CF_2O(CF_2CF_2O)_pCF_3$ (p represents an integer of 1 to 8), —$CF(CF_3)O(CF_2CF(CF_3)O)_qC_6F_{13}$ (q represents an integer of 1 to 4), and —$CF(CF_3)O(CF_2CF(CF_3)O)_rC_3F_7$ (r represents an integer of 1 to 5).

$R_{f1}$ is particularly preferably —$(CF_2)CF_3$ or —$(CF_2)_5CF_3$.

In Formula (24), $X_1$ represents a hydrogen atom, a fluorine atom, or a trifluoromethyl group. Among these, a fluorine atom and a trifluoromethyl group are preferable.

In Formula (24), $L_1$ represents a single bond or an alkylene group having 1 to 6 carbon atoms. Among these, an alkylene group having 1 to 2 carbon atoms is preferable.

In Formula (24), $L_2$ represents a single bond or an alkylene group having 1 to 6 carbon atoms that may be substituted with a hydroxyl group or a fluorine atom. Among these, an alkylene group having 1 to 2 carbon atoms is preferable.

In Formula (24), $L_3$ represents a single bond or an alkylene group having 1 to 6 carbon atoms. Among these, an alkylene group having 1 to 2 carbon atoms is preferable.

In Formula (24), each of $Y_1$ and $Z_1$ represents a single bond, —$CO_2$—, —$CO$—, —$OC(=O)O$—, —$SO_3$—, —$CONR_{245}$—, —$NHCOO$—, —$O$—, —$S$—, —$SO_2NR_{245}$—, or —$NR_{245}$—. Among these, —$CO_2$—, —$O$—, —$S$—, —$SO_2NR_{245}$—, and —$CONR_{245}$— are preferable. $R_{245}$ represents a hydrogen atom or an alkyl group having 1 to 5 carbon atoms.

Here, when both of $Y_1$ and $Z_1$ represent a group other than a single bond, $L_2$ represents an alkylene group having 1 to 6 carbon atoms that may be substituted with a fluorine atom.

As another preferred embodiment of the compound represented by Formula (1), a compound selected from the group consisting of compounds represented by the following Formulae (31) to (46) is exemplified. Herein, the compounds represented by Formulae (31) to (46) preferably contain a fluorine atom, and the fluorine content of the compounds preferably satisfies the range described above.

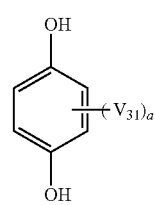

Formula (31)

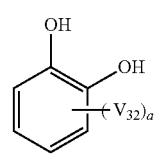

Formula (32)

-continued

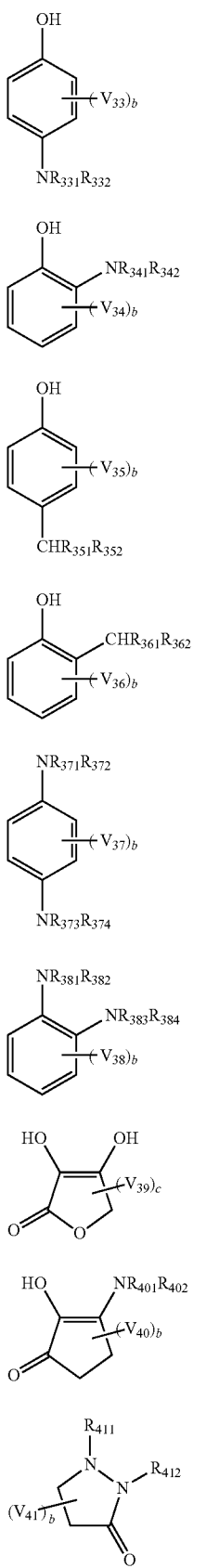

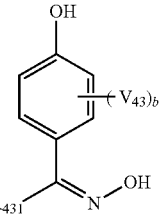

Formula (33)

Formula (34)

Formula (35)

Formula (36)

Formula (37)

Formula (38)

Formula (39)

Formula (40)

Formula (41)

Formula (42)

Formula (43)

Formula (44)

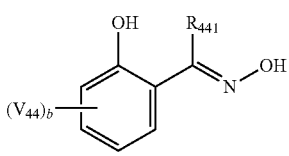

Formula (45)

Formula (46)

The compound represented by Formula (31) is a compound formed in a case in which in Formula (1), each of P and Q represents OH; Y represents $CR_6$; n represents 2; and $R_1$ on a carbon atom adjacent to P and $R_6$ on a carbon atom adjacent to Q form a ring by forming a double bond by being bonded to each other.

In Formula (31), $V_{31}$ represents a substituent, and a represents an integer of 1 to 4, preferably represents an integer of 1 or 2, and more preferably represents 1. At least one of the substituents represented by $V_{31}$ contains a fluorine atom. That is, when there is one substituent represented by $V_{31}$, the substituent may contain a fluorine atom, and when there are two or more substituents represented by $V_{31}$, at least one of the substituents may contain a fluorine atom. It is preferable that a fluorine atom is introduced into at least one group represented by $V_{31}$ by substituting a portion of hydrogen atoms or the entirety of the hydrogen atoms in the group (preferably by substituting a portion of hydrogen atoms or the entirety of the hydrogen atoms bonded to carbon atoms). Particularly, it is preferable that $V_{31}$ contains the $R_f$ group.

Examples of the substituent represented by $V_{31}$ include the substituents of the alkyl group represented by $R_2$ and $R_3$ in Formula (1) described above. When there is a plurality of groups represented by $V_{31}$ in Formula (31), the groups may be the same as or different from each other or may form a ring by being bonded to each other.

Specific examples of the compound represented by Formula (31) will be shown below, but the present invention is not limited thereto. Herein, the percentage listed together with the structural formula of the compound signifies the mass ratio of fluorine atoms (fluorine content).

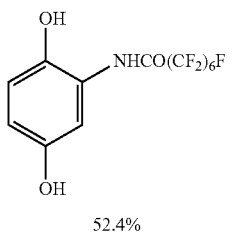

31-1

52.4%

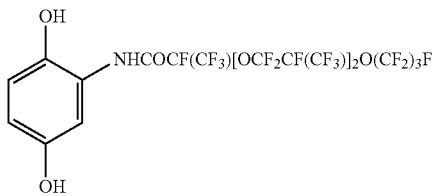

31-2

56.8%

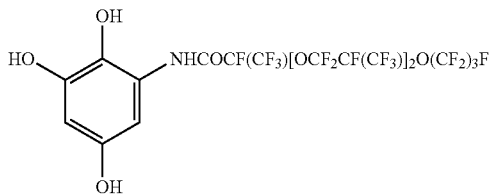

32-2

55.6%

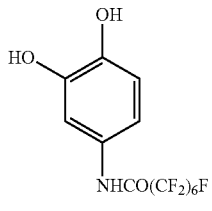

32-3

52.4%

The compound represented by Formula (32) is an example of a compound formed in a case in which in Formula (1), each of P and Q represents OH; Y represents $CR_6$; n represents 1; and $R_1$ on a carbon atom adjacent to P and $R_6$ on a carbon atom adjacent to Q form a ring by being bonded to each other.

In Formula (32), $V_{32}$ represents a substituent, and a represents an integer of 1 to 4, preferably represents an integer of 1 or 2, and even more preferably represents 1. At least one of the substituents represented by $V_{32}$ contains a fluorine atom. That is, when there is one substituent represented by $V_{32}$, the substituent may contain a fluorine atom, and when there are two or more substituents represented by $V_{32}$, at least one of the substituents may contain a fluorine atom. It is preferable that a fluorine atom is introduced into at least one group represented by $V_{32}$ by substituting a portion of hydrogen atoms or the entirety of the hydrogen atoms in the group (preferably by substituting a portion of hydrogen atoms or the entirety of the hydrogen atoms bonded to carbon atoms). Particularly, it is preferable that $V_{32}$ contains the $R_f$ group.

Examples of the substituent represented by $V_{32}$ include the substituents of the alkyl group represented by $R_2$ and $R_3$ in Formula (1) described above. When there is a plurality of groups represented by $V_{32}$ in Formula (32), the groups may be the same as or different from each other or may form a ring by being bonded to each other.

Specific examples of the compound represented by Formula (32) will be shown below, but the present invention is not limited thereto. Herein, the percentage listed together with the structural formula of the compound signifies the mass ratio of fluorine atoms (fluorine content).

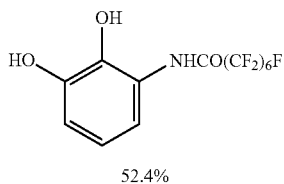

32-1

52.4%

The compound represented by Formula (33) is an example of a compound formed in a case in which in Formula (1), P represents OH; Q represents $NR_2R_3$; Y represents $CR_6$; n represents 2; and $R_1$ on a carbon atom adjacent to P and $R_6$ on a carbon atom adjacent to Q form a ring by forming a double bond by being bonded to each other.

In Formula (33), $V_{33}$ represents a substituent, and b represents an integer of 0 to 4, preferably represents an integer of 1 or 2, and even more preferably represents 1. Examples of the substituent represented by $V_{33}$ include the substituents of the alkyl group represented by $R_2$ and $R_3$ in Formula (1) described above. When there is a plurality of groups represented by $V_{33}$ in Formula (33), the groups may be the same as or different from each other or may form a ring by being bonded to each other.

Each of $R_{331}$ and $R_{332}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $V_{33}$, $R_{331}$, and $R_{332}$ contains a fluorine atom. Particularly, it is preferable that in at least one of the groups represented by $V_{33}$, $R_{331}$, and $R_{332}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{33}$, $R_{331}$, and $R_{332}$ contains the $R_f$ group.

When there is a plurality of groups represented by $V_{33}$, at least one of the plurality of groups represented by $V_{33}$, $R_{331}$, and $R_{332}$ contains a fluorine atom.

Specific examples of the compound represented by Formula (33) will be shown below, but the present invention is not limited thereto. Herein, the percentage listed together with the structural formula of the compound signifies the mass ratio of fluorine atoms (fluorine content).

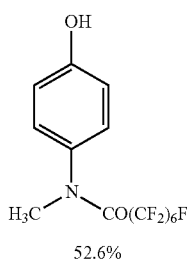

33-1

52.6%

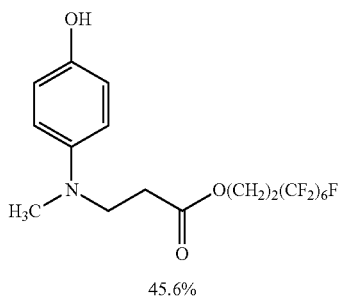

33-2

45.6%

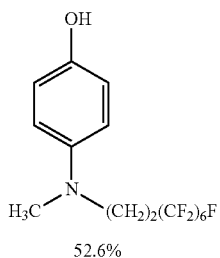

33-3

52.6%

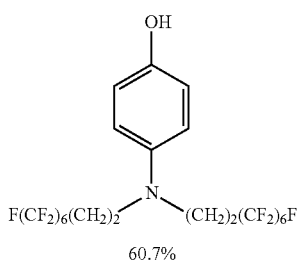

33-4

60.7%

The compound represented by Formula (34) is an example of a compound formed in a case in which in Formula (1), P represents OH; Q represents $NR_2R_3$; Y represents $CR_6$; n represents 1; and $R_1$ on a carbon atom adjacent to P and $R_6$ on a carbon atom adjacent to Q form a ring by being bonded to each other.

In Formula (34), $V_{34}$ represents a substituent, and b represents an integer of 0 to 4, preferably represents an integer of 0 to 2, and even more preferably represents 1. Examples of the substituent represented by $V_{34}$ include the substituents of the alkyl group represented by $R_2$ and $R_3$ in Formula (1) described above. When there is a plurality of groups represented by $V_{34}$ in Formula (34), the groups may be the same as or different from each other or may form a ring by being bonded to each other.

Each of $R_{341}$ and $R_{342}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $V_{34}$, $R_{341}$, and $R_{342}$ contains a fluorine atom. Particularly, it is preferable that in at least one of the groups represented by $V_{34}$, $R_{341}$, and $R_{342}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{34}$, $R_{341}$, and $R_{342}$ contains the $R_f$ group.

When there is a plurality of groups represented by $V_{34}$, at least one of the plurality of groups represented by $V_{34}$, $R_{341}$, and $R_{342}$ contains a fluorine atom.

Specific examples of the compound represented by Formula (34) will be shown below, but the present invention is not limited thereto. Herein, the percentage listed together with the structural formula of the compound signifies the mass ratio of fluorine atoms (fluorine content).

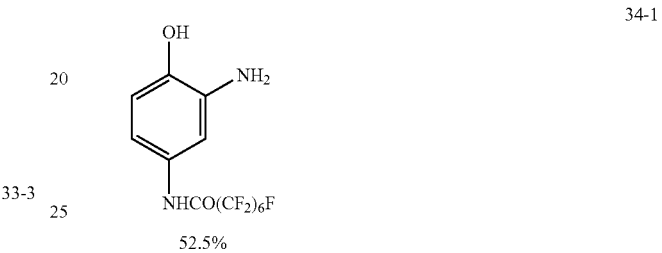

34-1

52.5%

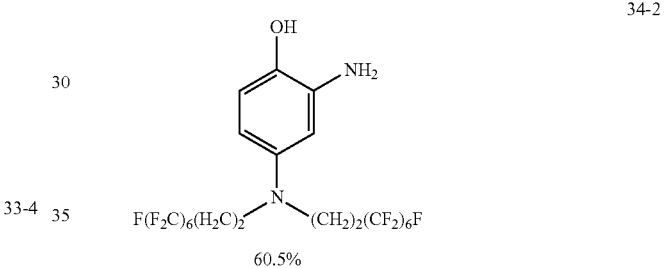

34-2

60.5%

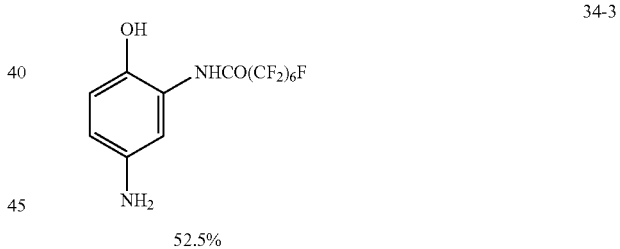

34-3

52.5%

The compound represented by Formula (35) is an example of a compound formed in a case in which in Formula (1), P represents OH; Q represents $CHR_4R_5$; Y represents $CR_6$; n represents 2; and $R_1$ on a carbon atom adjacent to P and $R_6$ on a carbon atom adjacent to Q form a ring by forming a double bond by being bonded to each other.

In Formula (35), $V_{35}$ represents a substituent, and b represents an integer of 0 to 4, preferably represents an integer of 1 or 2, and even more preferably represents 1. Examples of the substituent represented by $V_{35}$ include the substituents of the alkyl group represented by $R_2$ and $R_3$ in Formula (1) described above. When there is a plurality of groups represented by $V_{35}$ in Formula (35), the groups may be the same as or different from each other or may form a ring by being bonded to each other.

Each of $R_{351}$ and $R_{352}$ independently represents a hydrogen atom or a substituent. Examples of the substituent represented by $R_{351}$ and $R_{352}$ include the substituents of the alkyl group represented by $R_2$ and $R_3$ described above. The substituent is preferably an alkyl group, an alkenyl group, an alkynyl group, or an aryl group. Preferred examples of each of these substituents include the groups exemplified as $R_2$ and $R_3$ described above.

When $R_{351}$ and $R_{352}$ represent substituents, these groups may further have a substituent. Examples of the substituent include the substituents of the alkyl group represented by $R_2$ and $R_3$ in Formula (1) described above.

At least one of $V_{35}$, $R_{351}$, and $R_{352}$ contains a fluorine atom. Particularly, it is preferable that in at least one of the groups represented by $V_{35}$, $R_{351}$, and $R_{352}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{35}$, $R_{351}$, and $R_{352}$ contains the $R_f$ group.

When there is a plurality of groups represented by $V_{35}$, at least one of the plurality of groups represented by $V_{35}$, $R_{351}$, and $R_{352}$ contains a fluorine atom.

Specific examples of the compound represented by Formula (35) will be shown below, but the present invention is not limited thereto. Herein, the percentage listed together with the structural formula of the compound signifies the mass ratio of fluorine atoms (fluorine content).

35-1

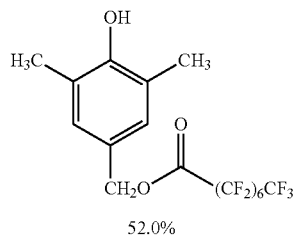

52.0%

35-2

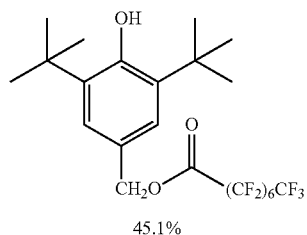

45.1%

35-3

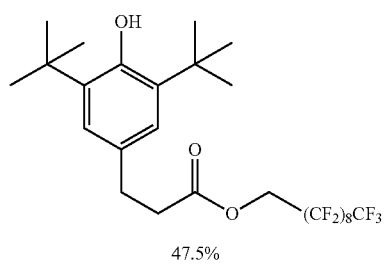

47.5%

-continued 35-4

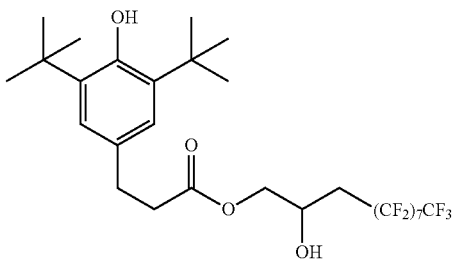

42.8%

35-5

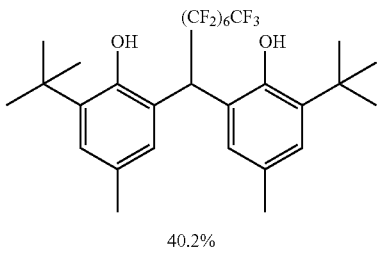

40.2%

35-6

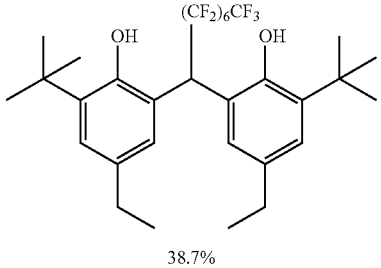

38.7%

The compound represented by Formula (36) is an example of a compound formed in a case in which in Formula (1), P represents OH; Q represents $CHR_4R_5$; Y represents $CR_6$; n represents 1; and $R_1$ on a carbon atom adjacent to P and $R_6$ on a carbon atom adjacent to Q form a ring by being bonded to each other.

In Formula (36), $V_{36}$ represents a substituent, and b represents an integer of 0 to 4, preferably represents an integer of 1 or 2, and even more preferably represents 1. Examples of the substituent represented by $V_{36}$ include the substituents of the alkyl group represented by $R_2$ and $R_3$ in Formula (1) described above. When there is a plurality of groups represented by $V_{36}$ in Formula (36), the groups may be the same as or different from each other or may form a ring by being bonded to each other.

Each of $R_{361}$ and $R_{362}$ independently represents a hydrogen atom or a substituent. Examples of the substituent represented by $R_{361}$ and $R_{362}$ include the substituents of the alkyl group represented by $R_2$ and $R_3$ described above. The substituent is preferably an alkyl group, an alkenyl group, an alkynyl group, or an aryl group. Preferred examples of each of these substituents include the groups exemplified as $R_2$ and $R_3$ described above.

When $R_{361}$ and $R_{362}$ represent substituents, these groups may further have a substituent. Examples of the substituent include the substituents of the alkyl group represented by $R_2$ and $R_3$ in Formula (1) described above.

At least one of $V_{36}$, $R_{361}$, and $R_{362}$ contains a fluorine atom. Particularly, it is preferable that in at least one of the groups represented by $V_{36}$, $R_{361}$, and $R_{362}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{36}$, $R_{361}$, and $R_{362}$ contains the $R_f$ group.

When there is a plurality of groups represented by $V_{36}$, at least one of the plurality of groups represented by $V_{36}$, $R_{361}$, and $R_{362}$ contains a fluorine atom.

Specific examples of the compound represented by Formula (36) will be shown below, but the present invention is not limited thereto. Herein, the percentage listed together with the structural formula of the compound signifies the mass ratio of fluorine atoms (fluorine content).

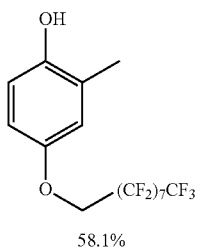

36-1

58.1%

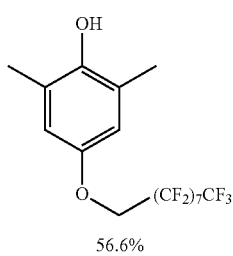

36-2

56.6%

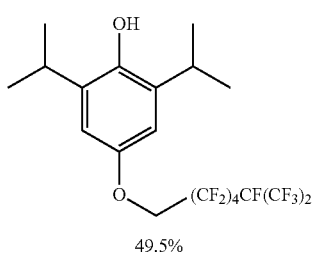

36-3

49.5%

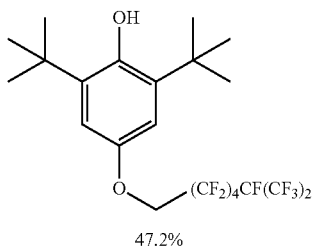

36-4

47.2%

The compound represented by Formula (37) is an example of a compound formed in a case in which in Formula (1), each of P and Q represents $NR_2R_3$; Y represents $CR_6$; n represents 2; and $R_1$ on a carbon atom adjacent to P and $R_6$ on a carbon atom adjacent to Q form a ring by forming a double bond by being bonded to each other.

In Formula (37), $V_{37}$ represents a substituent, and b represents an integer of 0 to 4, preferably represents an integer of 1 or 2, and even more preferably represents 1. Examples of the substituent represented by $V_{37}$ include the substituents of the alkyl group represented by $R_2$ and $R_3$ in Formula (1) described above. When there is a plurality of groups represented by $V_{37}$ in Formula (37), the groups may be the same as or different from each other or may form a ring by being bonded to each other.

Each of $R_{371}$, $R_{372}$, $R_{373}$, and $R_{374}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $V_{37}$, $R_{371}$, $R_{372}$, $R_{373}$, and $R_{374}$ contains a fluorine atom. Particularly, it is preferable that in at least one of the groups represented by $V_{37}$, $R_{371}$, $R_{372}$, $R_{373}$, and $R_{374}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{37}$, $R_{371}$, $R_{372}$, $R_{373}$, and $R_{374}$ contains the $R_f$ group.

When there is a plurality of groups represented by $V_{37}$, at least one of the plurality of groups represented by $V_{37}$, $R_{371}$, $R_{372}$, $R_{373}$, and $R_{374}$ contains a fluorine atom.

Specific examples of the compound represented by Formula (37) will be shown below, but the present invention is not limited thereto. Herein, the percentage listed together with the structural formula of the compound signifies the mass ratio of fluorine atoms (fluorine content).

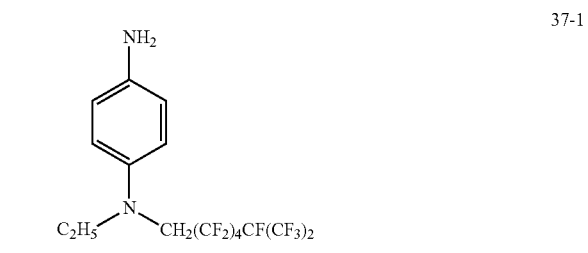

37-1

55.0%

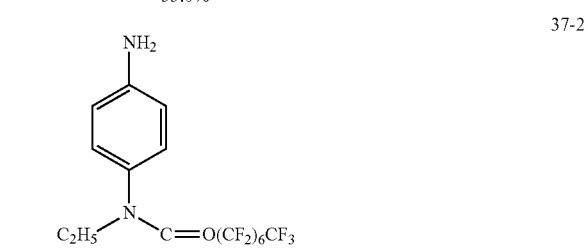

37-2

53.5%

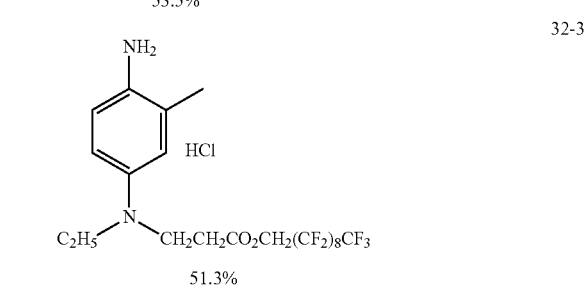

32-3

51.3%

The compound represented by Formula (38) is an example of a compound formed in a case in which in Formula (1), each of P and Q represents $NR_2R_3$; Y represents $CR_6$; n represents 1; and $R_1$ on a carbon atom adjacent to P and $R_6$ on a carbon atom adjacent to Q form a ring by being bonded to each other.

In Formula (38), $V_{38}$ represents a substituent, and b represents an integer of 0 to 4, preferably represents an integer of 1 or 2, and even more preferably represents 1. Examples of the substituent represented by $V_{38}$ include the substituents of the alkyl group represented by $R_2$ and $R_3$ in Formula (1) described above. When there is a plurality of groups represented by $V_{38}$ in Formula (38), the groups may be the same as or different from each other or may form a ring by being bonded to each other.

Each of $R_{381}$, $R_{382}$, $R_{383}$, and $R_{384}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $V_{38}$, $R_{381}$, $R_{382}$, $R_{383}$, and $R_{384}$ contains a fluorine atom. Particularly, it is preferable that in at least one of the groups represented by $V_{38}$, $R_{381}$, $R_{382}$, $R_{383}$, and $R_{384}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{38}$, $R_{381}$, $R_{382}$, $R_{383}$, and $R_{384}$ contains the $R_f$ group.

When there is a plurality of groups represented by $V_{38}$, at least one of the plurality of groups represented by $V_{38}$, $R_{381}$, $R_{382}$, $R_{383}$, and $R_{384}$ contains a fluorine atom.

Specific examples of the compound represented by Formula (38) will be shown below, but the present invention is not limited thereto. Herein, the percentage listed together with the structural formula of the compound signifies the mass ratio of fluorine atoms (fluorine content).

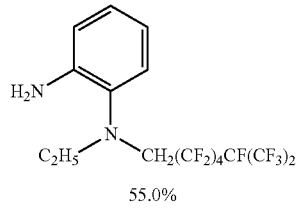

38-1

55.0%

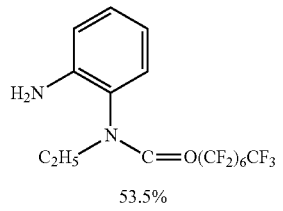

38-2

53.5%

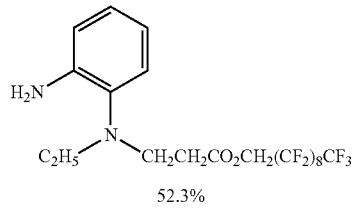

38-3

52.3%

The compound represented by Formula (39) is an example of a compound formed in a case in which in Formula (1), each of P and Q represents OH; Y represents $CR_6$; n represents 1; and $R_1$ on a carbon atom adjacent to P and $R_6$ on a carbon atom adjacent to Q form a ring by being bonded to each other.

In Formula (39), $V_{39}$ represents a substituent, and c represents an integer of 1 or 2 and preferably represents 1. At least one of the substituents represented by $V_{39}$ contains a fluorine atom. That is, when there is one substituent represented by $V_{39}$, the substituent may contain a fluorine atom, and when there are two or more substituents represented by $V_{39}$, at least one of the substituents may contain a fluorine atom. It is preferable that a fluorine atom is introduced into at least one of the groups represented by $V_{39}$ by substituting a portion of hydrogen atoms or the entirety of the hydrogen atoms in the group (preferably by substituting a portion of hydrogen atoms or the entirety of hydrogen atoms bonded to carbon atoms). Particularly, it is preferable that $V_{39}$ contains the $R_f$ group.

Examples of the substituent represented by $V_{39}$ include the substituents of the alkyl group represented by $R_2$ and $R_3$ in Formula (1) described above. When there is a plurality of groups represented by $V_{39}$ in Formula (39), the groups may be the same as or different from each other or may form a ring by being bonded to each other.

Specific examples of the compound represented by Formula (39) will be shown below, but the present invention is not limited thereto. Herein, the percentage listed together with the structural formula of the compound signifies the mass ratio of fluorine atoms (fluorine content).

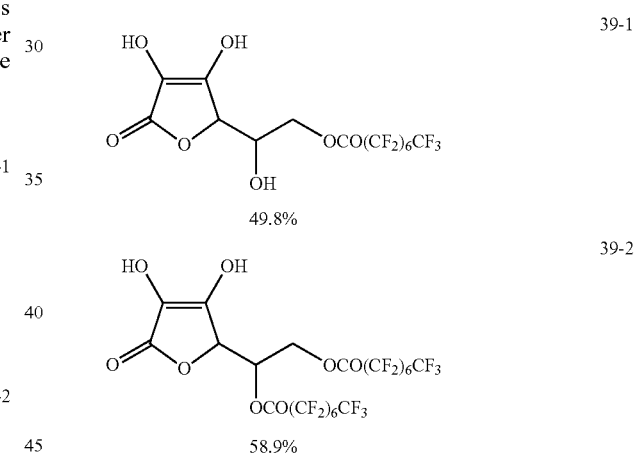

39-1

49.8%

39-2

58.9%

The compound represented by Formula (40) is an example of a compound formed in a case in which in Formula (1), P represents OH; Q represents $NR_2R_3$; Y represents $CR_6$; n represents 1; and $R_1$ on a carbon atom adjacent to P and $R_6$ on a carbon atom adjacent to Q form a ring by being bonded to each other.

In Formula (40), $V_{40}$ represents a substituent, and b represents an integer of 0 to 4, preferably represents an integer of 1 or 2, and even more preferably represents 1. Examples of the substituent represented by $V_{40}$ include the substituents of the alkyl group represented by $R_2$ and $R_3$ in Formula (1) described above. When there is a plurality of groups represented by $V_{40}$ in Formula (40), the groups may be the same as or different from each other or may form a ring by being bonded to each other.

Each of $R_{401}$ and $R_{402}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $V_{40}$, $R_{401}$, and $R_{402}$ contains a fluorine atom. Particularly, it is preferable that in at least one of the groups represented by $V_{40}$, $R_{401}$, and $R_{402}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{40}$, $R_{401}$, and $R_{402}$ contains the $R_f$ group.

When there is a plurality of groups represented by $V_{40}$, at least one of the plurality of groups represented by $V_{40}$, $R_{401}$, and $R_{402}$ contains a fluorine atom.

Specific examples of the compound represented by Formula (40) will be shown below, but the present invention is not limited thereto. Herein, the percentage listed together with the structural formula of the compound signifies the mass ratio of fluorine atoms (fluorine content).

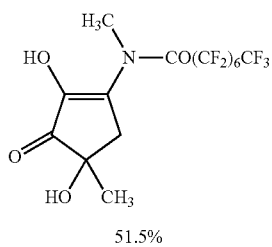

40-1

51.5%

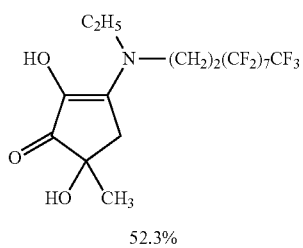

40-2

52.3%

The compound represented by Formula (41) is an example of a compound formed in a case in which in Formula (1), each of P and Q represents $NR_2R_3$; n represents 0; and $R_2$ and $R_3$ form a ring by being bonded to each other.

In Formula (41), $V_{41}$ represents a substituent, and b represents an integer of 0 to 4. Examples of the substituent represented by $V_{41}$ include the substituents of the alkyl group represented by $R_2$ and $R_3$ in Formula (1) described above. When there is a plurality of groups represented by $V_{41}$ in Formula (41), the groups may be the same as or different from each other or may form a ring by being bonded to each other.

Each of $R_{411}$ and $R_{412}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $V_{41}$, $R_{411}$, and $R_{412}$ contains a fluorine atom. Particularly, it is preferable that in at least one of the groups represented by $V_{41}$, $R_{411}$, and $R_{412}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{41}$, $R_{411}$, and $R_{412}$ contains the $R_f$ group.

When there is a plurality of groups represented by $V_{41}$, at least one of the plurality of groups represented by $V_{41}$, $R_{411}$, and $R_{412}$ contains a fluorine atom.

Specific examples of the compound represented by Formula (41) will be shown below, but the present invention is not limited thereto. Herein, the percentage listed together with the structural formula of the compound signifies the mass ratio of fluorine atoms (fluorine content).

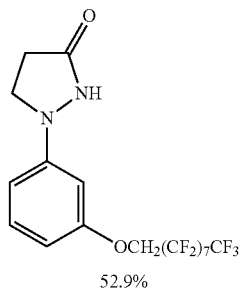

41-1

52.9%

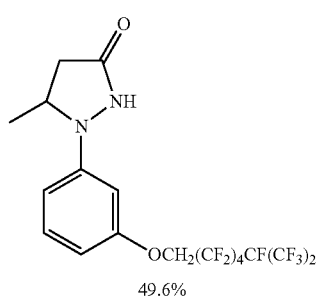

41-2

49.6%

The compound represented by Formula (42) is an example of a compound formed in a case in which in Formula (1), each of P and Q represents $NR_2R_3$; n represents 0; and $R_2$ and $R_3$ form a ring by being bonded to each other.

In Formula (42), $V_{42}$ represents a substituent, and d represents 0 or 1. Examples of the substituent represented by $V_{42}$ include the substituents of the alkyl group represented by $R_2$ and $R_3$ in Formula (1) described above. When there is a plurality of groups represented by $V_{42}$ in Formula (42), the groups may be the same as or different from each other or may form a ring by being bonded to each other.

Each of $R_{421}$, $R_{422}$, and $R_{423}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $V_{42}$, $R_{421}$, $R_{422}$, and $R_{423}$ contains a fluorine atom. Particularly, it is preferable that in at least one of the groups represented by $V_{42}$, $R_{421}$, $R_{422}$, and $R_{423}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{42}$, $R_{421}$, $R_{422}$, and $R_{423}$ contains the $R_f$ group.

When there is a plurality of groups represented by $V_{42}$, at least one of the plurality of groups represented by $V_{42}$, $R_{421}$, $R_{422}$, and $R_{423}$ contains a fluorine atom.

Specific examples of the compound represented by Formula (42) will be shown below, but the present invention is not limited thereto. Herein, the percentage listed together with the structural formula of the compound signifies the mass ratio of fluorine atoms (fluorine content).

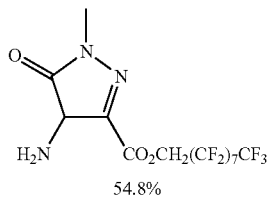

42-1

54.8%

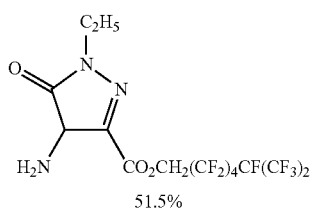

42-2

51.5%

The compound represented by Formula (43) is an example of a compound formed in a case in which in Formula (1), each of P and Q represents OH; Y represents $CR_6$ or a nitrogen atom; n represents 3; and $R_1$ and $R_6$ form a ring by being bonded to each other.

In Formula (43), $V_{43}$ represents a substituent, and b represents an integer of 0 to 4, preferably represents an integer of 1 or 2, and more preferably represents 1. Examples of the substituent represented by $V_{43}$ include the substituents of the alkyl group represented by $R_2$ and $R_3$ in Formula (1) described above. When there is a plurality of groups represented by $V_{43}$ in Formula (43), the groups may be the same as or different from each other or may form a ring by being bonded to each other.

$R_{431}$ represents a hydrogen atom or a substituent. Examples of the substituent represented by $R_{431}$ include the substituents of the alkyl group represented by $R_2$ and $R_3$ described above. The substituent is preferably an alkyl group, an alkenyl group, an alkynyl group, or an aryl group. Preferred examples of each of these substituents include the groups exemplified as $R_2$ and $R_3$ described above.

When $R_{431}$ represents a substituent, the substituent may further have a substituent which includes, for example, the substituents of the alkyl group represented by $R_2$ and $R_3$ in Formula (1) described above.

At least one of $V_{43}$ and $R_{431}$ contains a fluorine atom. Particularly, it is preferable that in at least one of the groups represented by $V_{43}$ and $R_{431}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{43}$ and $R_{431}$ contains the $R_f$ group.

When there is a plurality of groups represented by $V_{43}$, at least one of the plurality of groups represented by $V_{43}$ and $R_{431}$ contains a fluorine atom.

Specific examples of the compound represented by Formula (43) will be shown below, but the present invention is not limited thereto. Herein, the percentage listed together with the structural formula of the compound signifies the mass ratio of fluorine atoms (fluorine content).

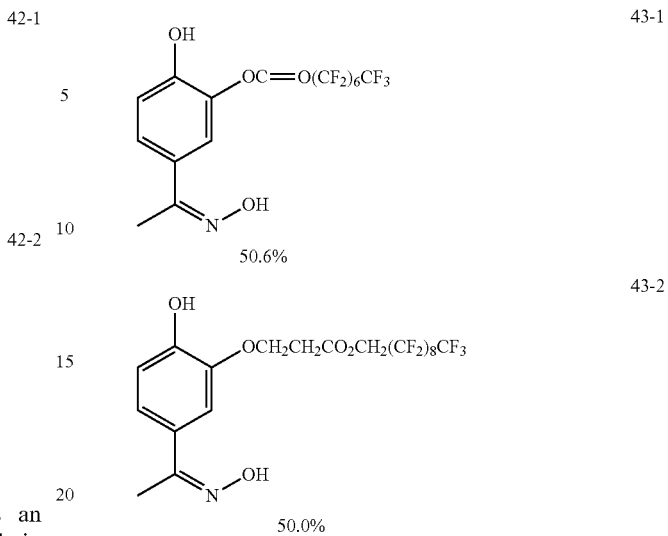

43-1

50.6%

43-2

50.0%

The compound represented by Formula (44) is an example of a compound formed in a case in which in Formula (1), each of P and Q represents OH; Y represents $CR_6$ or a nitrogen atom; n represents 2; and $R_1$ and $R_6$ form a ring by being bonded to each other.

In Formula (44), $V_{44}$ represents a substituent, and b represents an integer of 0 to 4, preferably represents an integer of 1 or 2, and more preferably represents 1. Examples of the substituent represented by $V_{44}$ include the substituents of the alkyl group represented by $R_2$ and $R_3$ in Formula (1) described above. When there is a plurality of groups represented by $V_{44}$ in Formula (44), the groups may be the same as or different from each other or may form a ring by being bonded to each other.

$R_{441}$ represents a hydrogen atom or a substituent. Examples of the substituent represented by $R_{441}$ include the substituents of the alkyl group represented by $R_2$ and $R_3$ described above. The substituent is preferably an alkyl group, an alkenyl group, an alkynyl group, or an aryl group. Preferred examples of each of these substituents include the groups exemplified as $R_2$ and $R_3$ described above.

When $R_{441}$ represents a substituent, the substituent may further have a substituent which includes, for example, the substituents of the alkyl group represented by $R_2$ and $R_3$ in Formula (1) described above.

At least one of $V_{44}$ and $R_{441}$ contains a fluorine atom. Particularly, it is preferable that in at least one of the groups represented by $V_{44}$ and $R_{441}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $V_{44}$ and $R_{441}$ contains the $R_f$ group.

When there is a plurality of groups represented by $V_{44}$, at least one of the plurality of groups represented by $V_{44}$ and $R_{441}$ contains a fluorine atom.

Specific examples of the compound represented by Formula (44) will be shown below, but the present invention is not limited thereto. Herein, the percentage listed together with the structural formula of the compound signifies the mass ratio of fluorine atoms (fluorine content).

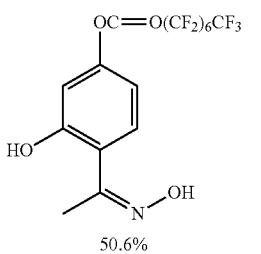

44-1

50.6%

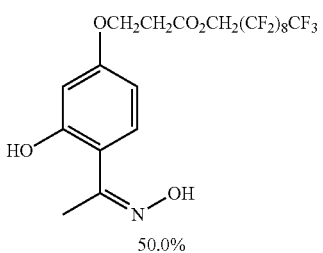

44-2

50.0%

The compound represented by Formula (45) is an example of a compound formed in a case in which in Formula (1), each of P and Q represents $NR_2R_3$, and n represents 0.

In Formula (45), each of $R_{451}$, $R_{452}$, $R_{453}$, and $R_{454}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $R_{451}$, $R_{452}$, $R_{453}$, and $R_{454}$ contains a fluorine atom. Particularly, it is preferable that in at least one of the groups represented by $R_{451}$, $R_{452}$, $R_{453}$, and $R_{454}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $R_{451}$, $R_{452}$, $R_{453}$, and $R_{454}$ contains the $R_f$ group.

Specific examples of the compound represented by Formula (45) will be shown below, but the present invention is not limited thereto. Herein, the percentage listed together with the structural formula of the compound signifies the mass ratio of fluorine atoms (fluorine content).

20-1

51.1%

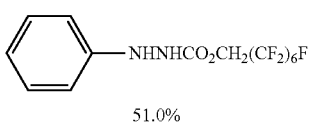

20-2

51.0%

The compound represented by Formula (46) is an example of a compound formed in a case in which in Formula (1), each P represents $NR_2R_3$; Q represents OH; and n represents 0.

In Formula (46), each of $R_{461}$ and $R_{462}$ independently represents a hydrogen atom or a group which can be substituted with a nitrogen atom. Examples of the group which can be substituted with a nitrogen atom preferably include the groups exemplified as $R_2$ and $R_3$ in Formula (1) described above.

At least one of $R_{461}$ and $R_{462}$ contains a fluorine atom. Particularly, it is preferable that in at least one of the groups represented by $R_{461}$ and $R_{462}$, a portion of hydrogen atoms or the entirety of hydrogen atoms (preferably a portion of hydrogen atoms or the entirety of hydrogen atoms bonded to carbon atoms) are substituted with a fluorine atom. It is more preferable that at least one of $R_{461}$ and $R_{462}$ contains the $R_f$ group.

Specific examples of the compound represented by Formula (46) will be shown below, but the present invention is not limited thereto. Herein, the percentage listed together with the structural formula of the compound signifies the mass ratio of fluorine atoms (fluorine content).

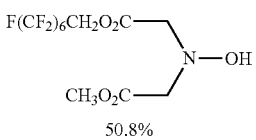

46-1

50.8%

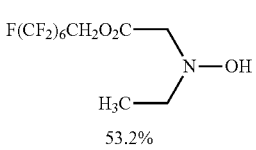

46-2

53.2%

Examples of the most preferred embodiment of the compound represented by Formula (1) include a compound represented by the following Formula (X1). The compound represented by Formula (X1) preferably contains a fluorine atom, and the fluorine content in the compound preferably satisfies the range described above.

Conceptually, the compound represented by the following Formula (X1) corresponds to a compound subordinate to Formula (35) described above. That is, $CR_{351}R_{352}$ in Formula (35) corresponds to A-COO—$X_{11}$—$Y_{11}$ shown below.

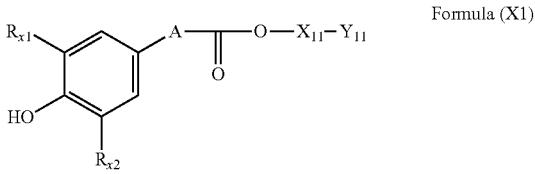

Formula (X1)

The definition, the specific examples, and the preferred embodiments of $R_{x1}$ and $R_{x2}$ are the same as those of $R_{241}$ and $R_{242}$.

A represents an alkylene group having 1 to 2 carbon atoms. A is preferably —$CH_2$— or —$CH_2CH_2$—, and more preferably —$CH_2CH_2$—.

$X_{11}$ represents an alkylene group having 1 to 3 carbon atoms that may have a hydroxyl group. $X_{11}$ is preferably —$CH_2$—, —$CH_2CH_2$—, —$CH_2CH(CH_3)$—, —$CH_2CH_2CH_2$—, —$CH_2CH(OH)CH_2$—, or —$CH_2CH(CH_2OH)$—, more preferably —$CH_2$—, —$CH_2CH_2$—, —$CH_2CH(OH)CH_2$—, or —$CH_2CH_2CH_2$—, and particularly preferably —$CH_2$— or —$CH_2CH_2$—.

$Y_{11}$ represents a linear perfluoroalkyl group having 4 to 12 carbon atoms. Preferred examples of the perfluoroalkyl group include $C_4F_9-$, $C_5F_{11}-$, $C_6F_{13}-$, $C_7F_{15}-$, $C_8F_{17}-$, $C_9F_{19}-$, $C_{10}F_{21}-$, and $C_{12}F_{25}-$. If the number of carbon atoms is within the range described above, the migration inhibition ability is further improved.

$R_{x1}$, $R_{x2}$, A, and $X_{11}$ may further have the substituent described above. Specific examples and preferred embodiments of the substituent are the same as those of the substituents of the alkyl group represented by $R_2$ and $R_3$ described above.

(Compound Represented by Formula (2))

Next, a compound represented by Formula (2) will be described.

$$R_7-C(=O)-H \qquad \text{Formula (2)}$$

In the present invention, the compound represented by Formula (2) also contains a compound (aldose or the like), which exhibits reducing properties due to the equilibrium established between an aldehyde group and a hemiacetal group, or a compound (fructose or the like) which can form an aldehyde group through the aldose-ketose isomerization that results from a Lobry de Bruyn-Van Ekenstein transformation reaction.

In Formula (2), $R_7$ represents an alkyl group, an alkenyl group, an alkynyl group, an aryl group, a heterocyclic group, or a group which is obtained by combining these groups.

When $R_7$ represents an alkyl group, an alkenyl group, an alkynyl group, or an aryl group, preferred examples of each of these groups include the groups exemplified as $R_2$ and $R_3$ described above. The alkyl group, the alkenyl group, and the alkynyl group may contain a linking group such as —CO—, —NH—, —O—, —S—, or a group which is obtained by combining these.

When $R_7$ represents a heterocyclic group, the heterocyclic group is preferably a monovalent group which is formed as a result of removing one hydrogen atom from a 5-membered or 6-membered substituted or unsubstituted aromatic or non-aromatic heterocyclic compound. The heterocyclic group is more preferably a 5-membered or 6-membered aromatic or non-aromatic heterocyclic group having 3 to 30 carbon atoms. Preferred examples of such a heterocyclic group include 2-furanyl, 2-thienyl, 2-pyrimidinyl, 2-benzothiazolyl, 2-benzoxazolyl, 2-imidazolyl, 4-imidazolyl, triazolyl, benzotriazolyl, thiadiazolyl, pyrrolidinyl, piperidinyl, imidazolidinyl, pyrazolidinyl, morpholinyl, tetrahydrofuranyl, tetrahydrothienyl, and the like.

$R_7$ is more preferably an alkyl group, an alkenyl group, an alkynyl group, or an aryl group, and particularly preferably an alkyl group or an aryl group.

The alkyl group, the alkenyl group, the alkynyl group, the aryl group, or the heterocyclic group represented by $R_7$ may further have a substituent. Examples of the substituent include the substituents of the alkyl group represented by $R_2$ and $R_3$ in Formula (1) described above.

In the group represented by $R_7$, a portion of hydrogen atoms or the entirety of hydrogen atoms (preferably a portion of hydrogen atoms or the entirety of hydrogen atoms bonded to carbon atoms) are substituted with a fluorine atom. Particularly, it is preferable that $R_7$ contains the $R_f$ group. Herein, it is preferable that the fluorine content in the compound represented by Formula (2) satisfies the range described above.

The group represented by $R_7$ may contain a hydroxyl group or a group represented by —COO—.

As one of the preferred embodiments of $R_7$, an aryl group containing a fluorine atom is exemplified.

Specific examples of the compound represented by Formula (2) will be shown below, but the present invention is not limited thereto. Herein, the percentage listed together with the structural formula of the compound signifies the mass ratio of fluorine atoms (fluorine content).

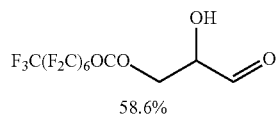

58.6%

2-1

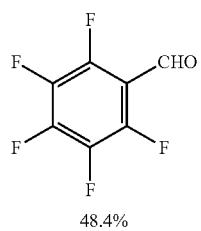

48.4%

2-2

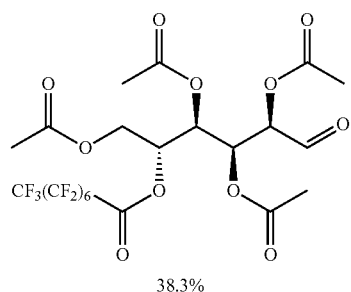

38.3%

2-3

(Compound Represented by Formula (3))

Next, a compound represented by Formula (3) will be described.

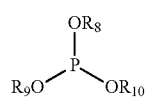

Formula (3)

In Formula (3), each of $R_8$, $R_9$, and $R_{10}$ independently represents an alkyl group, an alkenyl group, an alkynyl group, an aryl group, a heterocyclic group, or a group which is obtained by combining these groups.

Preferred examples of the alkyl group, the alkenyl group, the alkynyl group, the aryl group, and the heterocyclic group include the groups exemplified as $R_2$ and $R_3$ in Formula (1) described above. The alkyl group, the alkenyl group, and the alkynyl group may contain a linking group such as —CO—, —NH—, —O—, —S—, or a group which is obtained by combining these.

The groups represented by $R_8$, $R_9$, and $R_{10}$ may further have a substituent. Examples of the substituent include the substituents of the alkyl group represented by $R_2$ and $R_3$ in Formula (1) described above.

In at least one of the groups represented by $R_8$ to $R_{10}$, a portion of hydrogen atoms or the entirety of hydrogen atoms (preferably a portion of hydrogen atoms or the entirety of hydrogen atoms bonded to carbon atoms) are substituted with a fluorine atom. Particularly, it is preferable that at least one of the groups represented by $R_8$ to $R_{10}$ contains the $R_f$ group. As one of the preferred embodiments of $R_8$ to $R_{10}$, an aryl group substituted with the $R_f$ group is exemplified. The number of the $R_f$ group substituting the aryl group is not particularly limited. However, the number of the $R_f$ group is preferably 1 to 4, and more preferably 1 to 2.

It is preferable that the fluorine content in the compound represented by Formula (3) satisfies the range described above.

Specific examples of the compound represented by Formula (3) will be shown below, but the present invention is not limited thereto. Herein, the percentage listed together with the structural formula of the compound signifies the mass ratio of fluorine atoms (fluorine content).

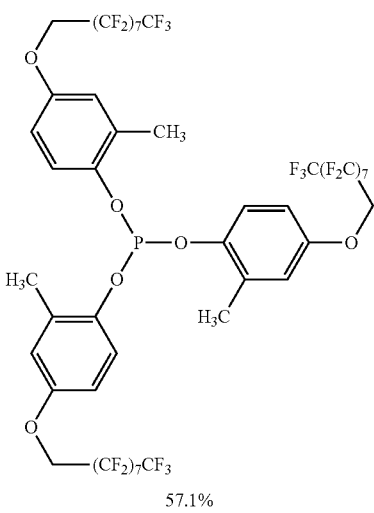

3-1

57.1%

(Compound Represented by Formula (4))

Next, a compound represented by Formula (4) will be described.

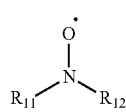

Formula (4)

In Formula (4), each of $R_{11}$ and $R_{12}$ independently represents an alkyl group, an alkenyl group, an alkynyl group, an aryl group, a heterocyclic group, or a group which is obtained by combining these groups. Preferred examples of the alkyl group, the alkenyl group, the alkynyl group, the aryl group, and the heterocyclic group include the groups exemplified as $R_2$ and $R_3$ in Formula (1) described above. The alkyl group, the alkenyl group, and the alkynyl group may contain a linking group such as —CO—, —NH—, —O—, —S—, or a group which is obtained by combining these.

The group represented by $R_{11}$ and $R_{12}$ may further have a substituent. Examples of the substituent include the substituents of the alkyl group represented by $R_2$ and $R_3$ in Formula (1) described above.

$R_{11}$ and $R_{12}$ may form a ring by being bonded to each other, and the formed ring may contain a substituent. Examples of the substituent include the substituents of the alkyl group represented by $R_2$ and $R_3$ in Formula (1) described above.

In at least one of the groups represented by $R_{11}$ and $R_{12}$, a portion of hydrogen atoms or the entirety of hydrogen atoms (preferably a portion of hydrogen atoms or the entirety of hydrogen atoms bonded to carbon atoms) are substituted with a fluorine atom. Particularly, it is preferable that at least one of the groups represented by $R_{11}$ and $R_{12}$ contains the $R_f$ group. Herein, it is preferable that the fluorine content in the compound represented by Formula (4) satisfies the range described above.

As one of the preferred embodiments of the compound represented by Formula (4), a compound represented by the following Formula (4A) is exemplified.

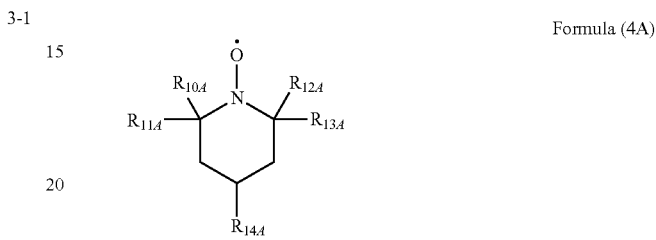

Formula (4A)

Each of $R_{10A}$ to $R_{13A}$ independently represents an alkyl group.

$R_{14A}$ represents a substituent containing a fluorine atom.

Examples of the substituent include the substituents of the alkyl group represented by $R_2$ and $R_3$ in Formula (1) described above. The group represented by $R_{14A}$ may further have a substituent. Examples of the substituent include the substituents of the alkyl group represented by $R_2$ and $R_3$ in Formula (1) described above.

$R_{14A}$ contains a fluorine atom. Particularly, it is preferable that a portion of hydrogen atoms or the entirety of hydrogen atoms in $R_{14A}$ (preferably a portion of hydrogen atoms or the entirety of hydrogen atoms bonded to carbon atoms) are substituted with a fluorine atom. It is more preferable that $R_{14A}$ contain the $R_f$ group. $R_{14A}$ is more preferably the $R_f$ group which may contain —CO—, —NH—, —O—, —S—, or a group which is obtained by combining these. Herein, it is preferable that the fluorine content in the compound represented by Formula (4A) satisfies the range described above.

Specific examples of the compound represented by Formula (4) will be shown below, but the present invention is not limited thereto. Herein, the percentage listed together with the structural formula of the compound signifies the mass ratio of fluorine atoms (fluorine content).

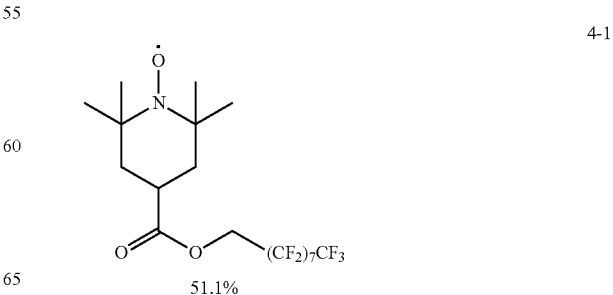

4-1

51.1%

-continued 4-2

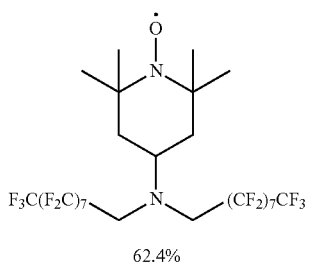

62.4%

(Compound Represented by Formula (5))

Next, a compound represented by Formula (5) will be described.

Z—SH          Formula (5)

In Formula (5), Z represents an alkyl group, an alkenyl group, an alkynyl group, an aryl group, a heterocyclic group, or a group which is obtained by combining these groups. Preferred examples of the alkyl group, the alkenyl group, the alkynyl group, the aryl group, and the heterocyclic group include the groups exemplified as $R_2$ and $R_3$ in Formula (1) described above.

The group represented by Z may further have a substituent. Examples of the substituent include the substituents of the alkyl group represented by $R_2$ and $R_3$ in Formula (1) described above.

In the group represented by Z, a portion of hydrogen atoms or the entirety of hydrogen atoms (preferably a portion of hydrogen atoms or the entirety of hydrogen atoms bonded to carbon atoms) are substituted with a fluorine atom. Particularly, it is preferable that Z contains the $R_f$ group. Herein, it is preferable that the fluorine content in the compound represented by Formula (5) satisfies the range described above.

The compound represented by Formula (5) is preferably a compound represented by any of Formulae (51) to (54).

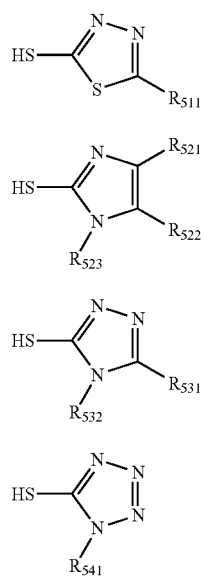

In Formula (51), $R_{511}$ represents a substituent containing a fluorine atom.

Examples of the substituent include the substituents of the alkyl group represented by $R_2$ and $R_3$ in Formula (1) described above. The group represented by $R_{511}$ may further have a substituent. Examples of the substituent include the substituents of the alkyl group represented by $R_2$ and $R_3$ in Formula (1) described above.

$R_{511}$ contains a fluorine atom. Particularly, it is preferable that a portion of hydrogen atoms or the entirety of hydrogen atoms in $R_{511}$ (preferably a portion of hydrogen atoms or the entirety of hydrogen atoms bonded to carbon atoms) are substituted with a fluorine atom. It is more preferable that $R_{511}$ contains the $R_f$ group. Herein, it is preferable that the fluorine content in the compound represented by Formula (51) satisfies the range described above.

Specific examples of the compound represented by Formula (51) will be shown below, but the present invention is not limited thereto. Herein, the percentage listed together with the structural formula of the compound signifies the mass ratio of fluorine atoms (fluorine content).

51-1

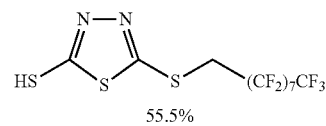

55.5%

51-2

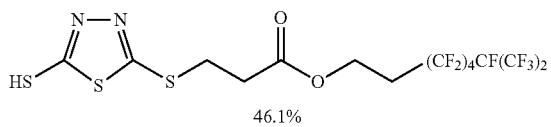

46.1%

51-3

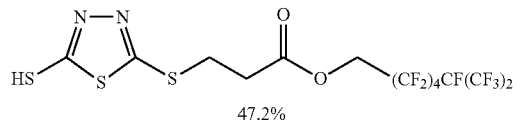

47.2%

In Formula (52), each of $R_{521}$ and $R_{522}$ independently represents a hydrogen atom or a substituent. $R_{523}$ represents a hydrogen atom or a group which can be substituted with a nitrogen atom. Examples of the group which can be substituted with a nitrogen atom preferably include the groups exemplified as $R_2$ and $R_3$ in Formula (1) described above. Furthermore, examples of the substituent include the substituents of the alkyl group represented by $R_2$ and $R_3$ in Formula (1) described above. $R_{521}$, $R_{522}$, and $R_{523}$ may be the same as or different from each other, or may form a ring by being bonded to each other.

At least one of the groups represented by $R_{521}$, $R_{522}$, and $R_{523}$ contains a fluorine atom. Particularly, it is preferable that in at least one of the groups represented by $R_{521}$, $R_{522}$, and $R_{523}$, a portion of hydrogen atoms or the entirety of hydrogen atoms (preferably a portion of hydrogen atoms or the entirety of hydrogen atoms bonded to carbon atoms) are preferably substituted with a fluorine atom. Furthermore, it is preferable that at least one of the groups represented by $R_{521}$, $R_{532}$, and $R_{523}$ contains the $R_f$ group. Herein, it is preferable that the fluorine content in the compound represented by Formula (52) satisfies the range described above.

Specific examples of the compound represented by Formula (52) will be shown below, but the present invention is not limited thereto.

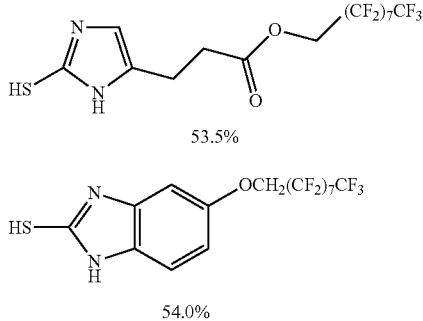

52-1

53.5%

52-2

54.0%

In Formula (53), $R_{531}$ represents a hydrogen atom or a substituent. $R_{532}$ represents a hydrogen atom or a group which can be substituted with a nitrogen atom. Examples of the group which can be substituted with a nitrogen atom preferably include the groups exemplified as $R_2$ and $R_3$ in Formula (1) described above. Furthermore, examples of the substituent include the substituents of the alkyl group represented by $R_2$ and $R_3$ in Formula (1) described above. $R_{531}$ and $R_{532}$ may be the same as or different from each other, or may form a ring by being bonded to each other.

At least one of the groups represented by $R_{531}$ and $R_{532}$ contains a fluorine atom. Particularly, in at least one of the groups represented by $R_{531}$ and $R_{532}$, a portion of hydrogen atoms or the entirety of the hydrogen atoms (preferably a portion of hydrogen atom or the entirety of hydrogen atoms bonded to carbon atoms) are preferably substituted with a fluorine atom. It is preferable that at least one of the groups represented by $R_{531}$ and $R_{532}$ contains the $R_f$ group. Furthermore, it is preferable that the fluorine content in the compound represented by Formula (53) satisfies the range described above.

Specific examples of the compound represented by Formula (53) will be shown below, but the present invention is not limited thereto. Herein, the percentage listed together with the structural formula of the compound signifies the mass ratio of fluorine atoms (fluorine content).

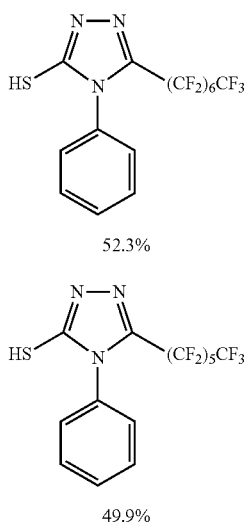

53-1

52.3%

53-2

49.9%

In Formula (54), $R_{541}$ represents a fluorine atom-containing group which can be substituted with a nitrogen atom. Examples of the group which can be substituted with a nitrogen atom preferably include the groups exemplified as $R_2$ and $R_3$ in Formula (1) described above.

$R_{541}$ contains a fluorine atom. Particularly, it is preferable that a portion of hydrogen atoms or the entirety of hydrogen atoms in $R_{541}$ (preferably a portion of hydrogen atoms or the entirety of hydrogen atoms bonded to carbon atoms) are substituted with a fluorine atom. It is more preferable that $R_{541}$ contains the $R_f$ group. Herein, it is preferable that the fluorine content in the compound represented by Formula (54) satisfies the range described above.

Specific examples of the compound represented by Formula (54) will be shown below, but the present invention is not limited thereto. Herein, the percentage listed together with the structural formula of the compound signifies the mass ratio of fluorine atoms (fluorine content).

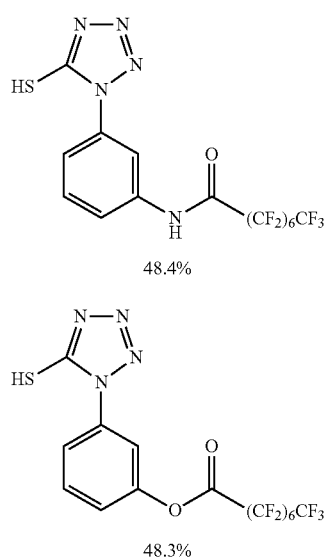

54-1

48.4%

54-2

48.3%

As the most preferred embodiment of the compound represented by Formula (5), a compound represented by the following Formula (Y) is exemplified.

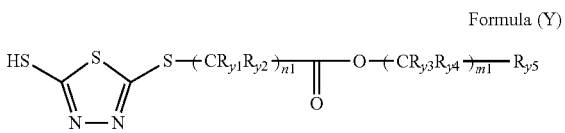

Formula (Y)

In Formula (Y), each of $R_{y1}$ and $R_{y2}$ independently represents a hydrogen atom or an alkyl group. n1 represents 1 or 2, and preferably represents 2. When n1 is 2, the structures of a plurality of units represented by $CR_{y1}R_{y2}$ may be the same as or different from each other.

When each of $R_{y1}$ and $R_{y2}$ represents an alkyl group, the alkyl group preferably has 1 to 30 carbon atoms, more preferably has 1 to 15 carbon atoms, and particularly preferably has 1 to 6 carbon atoms. Examples of such an alkyl group preferably include methyl, ethyl, n-propyl, isopropyl, t-butyl, n-octyl, eicosyl, chloromethyl, hydroxymethyl, aminoethyl, N,N-dimethylaminomethyl, 2-chloroethyl, 2-cyanoethyl, 2-hydroxyethyl, 2-(N,N-dimethylamino)ethyl, 2-ethylhexyl, and the like.

The structure represented by $(CR_{y1}R_{y2})_{n1}$ is preferably —$CH_2$—, —$CH_2CH_2$—, or —$CH_2CH(CH_3)$—, more preferably —$CH_2CH_2$— or —$CH_2CH(CH_3)$—, and particularly preferably —$CH_2CH_2$—.

Each of $R_{y3}$ and $R_{y4}$ independently represents a hydrogen atom or a substituent. Specific examples and preferred embodiments of the substituent are the same as those of the substituents of the alkyl group represented by $R_2$ and $R_3$ described above. m1 represents an integer of 1 to 6. When m1 is equal to or greater than 2, the structures of a plurality of units represented by $CR_{y3}R_{y4}$ may be the same as or different from each other. Furthermore, $R_{y3}$ and $R_{y4}$ may form a ring by being bonded to each other.

The structure represented by $(CR_{y3}R_{y4})_{m1}$ is preferably —$CH_2$—, —$CH_2CH_2$—, —$CH_2CH(CH_3)$—, —$CH_2CH_2CH_2$—, —$CH_2CH(OH)CH_2$—, or —$CH_2CH(CH_2OH)$—, more preferably —$CH_2$—, —$CH_2CH_2$—, —$CH_2CH(OH)CH_2$—, or —$CH_2CH_2CH_2$—, and particularly preferably —$CH_2$— or —$CH_2CH_2$—.

$R_{y5}$ represents a perfluorolalkyl group having 1 to 20 carbon atoms. The perfluoroalkyl group may be linear or branched.

Examples of the linear or branched perfluoroalkyl group having 1 to 20 carbon atoms include $CF_3$—, $C_2F_5$—, $C_3F_7$—, $C_4F_9$—, $C_5F_{11}$—, $C_6F_{13}$—, $C_7F_{15}$—, $C_8F_{17}$—, $C_9F_{19}$—, $C_{10}F_{71}$—, $C_{12}F_{25}$—, $C_{14}F_{29}$—, and the like.

A compound represented by Formula (6) will be described. Herein, it is preferable that the compound represented by Formula (6) contains fluorine atoms such that the aforementioned fluorine content is satisfied.

Formula (6)

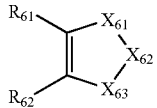

In Formula (6), each of $X_{61}$, $X_{62}$, and $X_{63}$ independently represents —NH—, —N=, =N—, 13 $CR_x$=, =$CR_x$—, or —S—. $R_x$ represents a hydrogen atom, —$NH_2$, or a linear or branched alkyl group having 1 to 15 carbon atoms. In the alkyl group, one carbon atom or two or more carbon atoms which are not adjacent to each other may be substituted with —O—, —S—, —$NR_0$, —CO—, —CO—O—, —O—CO—, —O—CO—O—, —$CR_0$=$CR_{00}$—, or —C≡C—. Furthermore, one or more hydrogen atoms in the alkyl group may be substituted with a fluorine atom, a chlorine atom, a bromine atom, an iodine atom, or —CN. Each of $R_0$ and $R_{00}$ independently represents a hydrogen atom or a carbyl or hydrocarbyl group which may have a substituent and one or more heteroatoms. Specific examples and preferred embodiments of the substituent are the same as those of the substituents of the alkyl group represented by $R_2$ and $R_3$ described above. The heteroatom is not particularly limited, and examples thereof include an oxygen atom, a nitrogen atom, a sulfur atom, a phosphorus atom, and the like. At least one of $X_{61}$, $X_{67}$, and $X_{63}$ is not —$CR_x$= or =$CR_x$—.

Each of $R_{61}$ and $R_{62}$ independently represents a fluorine atom, a chlorine atom, -Sp-P, a linear or branched alkyl group having 1 to 15 carbon atoms, or an aryl group, a heteroaryl group, an aryloxy group, a heteroaryloxy group, an arylcarbonyl group, a heteroarylcarbonyl group, an aryl- carbonyloxy group, a heteroarylcarbonyloxy group, an aryloxycarbonyl group, or a heteroaryloxycarbonyl group which has 2 to 30 carbon atoms and may have a substituent (specific examples and preferred embodiments of the substituent are the same as those of the substituents of the alkyl group represented by $R_2$ and $R_3$ described above). In the alkyl group, one carbon atom or two or more carbon atoms which are not adjacent to each other may be substituted with —O—, —S—, —$NR_0$, —CO—, —CO—O—, —O—CO—, —O—CO—O—, —$CR_0$=$CR_{00}$—, or —C≡C—. Furthermore, one or more hydrogen atoms in the alkyl group may be substituted with a fluorine atom, a chlorine atom, a bromine atom, an iodine atom, or —CN. Each of $R_0$ and $R_{00}$ independently represents a hydrogen atom or a carbyl or hydrocarbyl group which may have a substituent and one or more heteroatoms. Specific examples and preferred embodiments of the substituent are the same as those of the substituents of the alkyl group represented by $R_2$ and $R_3$ described above. Sp represents a single bond or a divalent organic group. Specific examples and preferred embodiments of the divalent organic group are the same as those of $L_A$ described above. P represents a polymerizable group or a cross-linking group. Specific examples of the polymerizable group and the cross-linking group include a methacryloyl group, an acryloyl group, an itaconic acid ester group, a crotonic acid ester group, an isocrotonic acid ester group, a maleic acid ester group, a styryl group, a vinyl group, an acrylamide group, a methacrylamide group, and the like. $R_{61}$ and $R_{62}$ may form an aromatic ring or an aromatic heterocyclic ring having 5 to 7 ring atoms by being bonded to each other. The aromatic ring and the aromatic heterocyclic ring may have 1 to 6 substituents. Specific examples and preferred embodiments of the substituents are the same as those of the substituents of the alkyl group represented by $R_2$ and $R_3$ described above.

The "carbyl group" refers to any monovalent or polyvalent organic group portion (for example, —C≡C—) not containing a non-carbon atom or refers to any monovalent or polyvalent organic group portion (for example, carbonyl) containing at least one carbon atom optionally bonded to at least one of the non-carbon atoms including N, O, S, P, Si, Se, As, Te, and Ge. The "hydrocarbyl group" refers to a carbyl group which additionally contains one or more H atoms and optionally contains any one or more heteroatoms including N, O, S, P, Si, Se, As, Te, and Ge.

In the groups represented by $R_{61}$, $R_{62}$, $X_{61}$, $X_{62}$, and $X_{63}$, a portion of hydrogen atoms or the entirety of hydrogen atoms (preferably a portion of hydrogen atoms or the entirety of hydrogen atoms bonded to carbon atoms) are substituted with a fluorine atom. Herein, it is preferable that the fluorine content in the compound represented by Formula (6) satisfies the range described above.

The compound represented by Formula (6) is preferably a compound represented by the following Formula (22). Herein, the compound represented by Formula (22) preferably contains a fluorine atom, and the fluorine content in the compound preferably satisfies the range described above.

Formula (22)

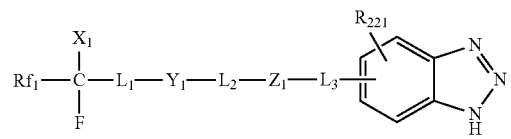

The definition, the specific examples, and the preferred embodiment of each of $Rf_1$, $X_1$, $L_1$, $L_2$, $L_3$, $Y_1$, and $Z_1$ in Formula (22) are the same as those of each of $Rf_1$, $X_1$, $L_1$, $L_2$, $L_3$, $Y_1$, and $Z_1$ in Formula (24) described above.

$R_{221}$ represents a hydrogen atom, a linear or branched alkyl group having 1 to 8 carbon atoms, or $Rf_1$—$CFX_1$-$L_1$-$Y_1$-$L_2$-$Z_1$-$L_3$-.

Here, when both of $Y_1$ and $Z_1$ represent a group other than a single bond, $L_2$ represents an alkylene group having 1 to 6 carbon atoms that may be substituted with a fluorine atom.

Specific examples of the compound represented by Formula (22) will be shown below, but the present invention is not limited thereto.

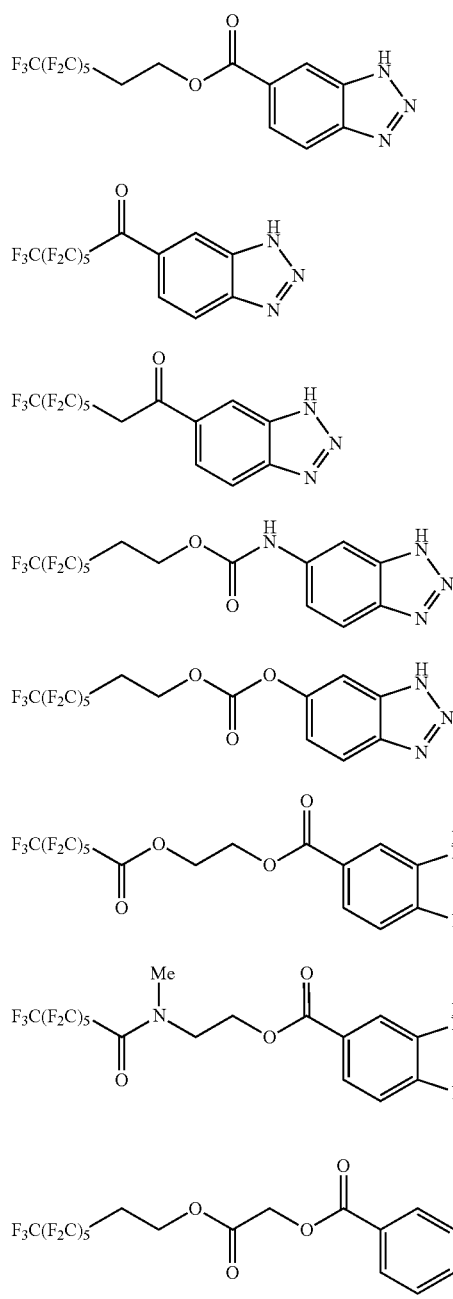
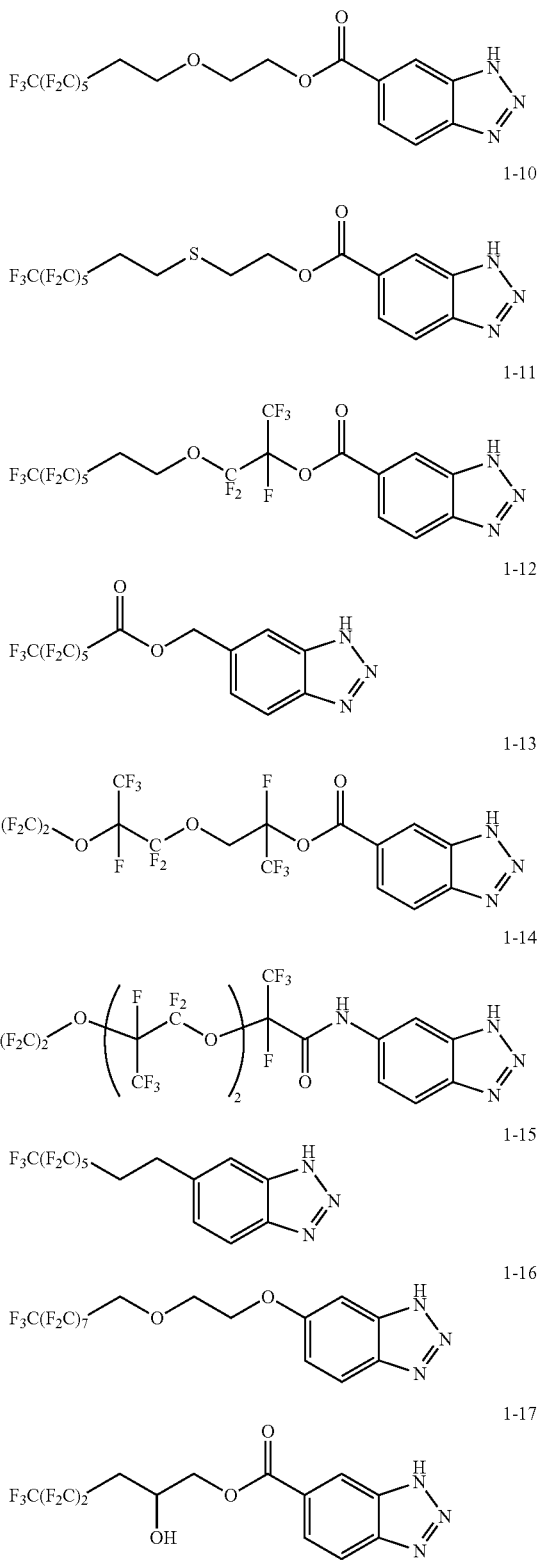

(Compound Represented by Formula (7))

Next, a compound represented by Formula (7) will be described.

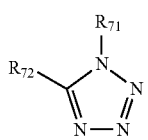

Formula (7)

In Formula (7), each of $R_{71}$ and $R_{72}$ independently represents a hydrogen atom, an alkyl group, an alkenyl group, an alkynyl group, an aryl group, a heterocyclic group, or a group which is obtained by combining these groups. Particularly, $R_{71}$ is preferably a hydrogen atom, and $R_{72}$ is preferably an alkyl group or an aryl group. Preferred examples of the alkyl group, the alkenyl group, the alkynyl group, the aryl group, and the heterocyclic group include the groups exemplified as $R_2$ and $R_3$ in Formula (1) described above. Herein, the alkyl group, the alkenyl group, or the alkynyl group may contain a linking group such as —CO—, —NH—, —O—, —S—, or a group which is obtained by combining these.

In at least one of the groups represented by $R_{71}$ and $R_{72}$, a portion of hydrogen atoms or the entirety of hydrogen atoms are substituted with a fluorine atom. Herein, it is preferable that the fluorine content in the compound represented by Formula (7) satisfies the range described above.

As a preferred embodiment of the compound represented by Formula (7), a compound represented by Formula (7A) is exemplified.

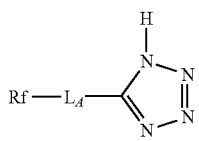

Formula (7A)

$L_A$ represents a single bond or a divalent organic group. Examples of the divalent organic group include a linear, branched, or cyclic divalent aliphatic hydrocarbon group (for example, an alkylene group such as a methylene group, an ethylene group, or a propylene group), a linear, branched, or cyclic divalent aromatic hydrocarbon group (for example, a phenylene group), —O—, —S—, —SO_2—, —NR_{222}—, —CO—, —NH—, —COO—, —CONR_{222}—, —O—CO—O—, —SO_3—, —NHCOO—, —SO_2NR_{222}—, —NH—CO—NH—, a group which is obtained by combining a plurality of these (for example, an alkyleneoxy group, an alkyleneoxycarbonyl group, or an alkylenecarbonyloxy group), and the like. $R_{222}$ represents a hydrogen atom or an alkyl group having 1 to 5 carbon atoms.

The $R_f$ group represents a fluoroalkyl group (preferably a perfluoroalkyl group), and the definition and preferred range of the $R_f$ group are as described above.

(Compound Represented by Formula (8))

Next, a compound represented by Formula (8) will be described. Herein, it is preferable that the compound represented by Formula (8) contains fluorine atoms such that the aforementioned fluorine content is satisfied.

Z1-S—S—Z2    Formula (8)

In Formula (8), each of Z1 and Z2 independently represents an alkyl group, an alkenyl group, an alkynyl group, an aryl group, a heterocyclic group, or a group which is obtained by combining these groups. Among these, an aryl group and a heterocyclic group are preferable. Preferred examples of the alkyl group, the alkenyl group, the alkynyl group, the aryl group, and the heterocyclic group include the groups exemplified as $R_2$ and $R_3$ in Formula (1) described above. Herein, the alkyl group, the alkenyl group, or the alkynyl group may contain a linking group such as —CO—, —NH—, —O—, —S—, or a group which is obtained by combining these.

Z1 and Z2 may contain a substituent. Specific examples and preferred embodiments of the substituent are the same as those of the substituents of the alkyl group represented by $R_2$ and $R_3$ described above.

In at least one of the groups represented by Z1 and Z2, a portion of hydrogen atoms or the entirety of hydrogen atoms are substituted with a fluorine atom. Herein, it is preferable that the fluorine content of the compound represented by Formula (8) satisfies the range described above.

The alkyl group, the alkenyl group, the alkynyl group, and the aryl group may contain a heteroatom (for example, an oxygen atom or a sulfur atom).

The compound represented by Formula (8) is preferably a compound represented by the following Formula (23). Herein, the compound represented by Formula (23) preferably contains fluorine atoms, and the fluorine content in the compound preferably satisfies the range described above.

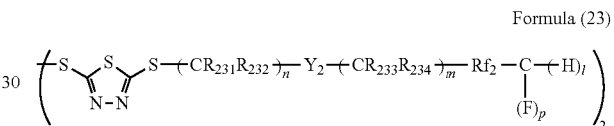

Formula (23)

In Formula (23), each of $R_{231}$ and $R_{232}$ independently represents a hydrogen atom or an alkyl group. When each of $R_{231}$ and $R_{232}$ represents an alkyl group, the alkyl group preferably has 1 to 30 carbon atoms, more preferably has 1 to 15 carbon atoms, and particularly preferably has 1 to 6 carbon atoms. Examples of such an alkyl group preferably include methyl, ethyl, n-propyl, isopropyl, t-butyl, n-octyl, eicosyl, chloromethyl, hydroxymethyl, aminoethyl, N,N-dimethylaminomethyl, 2-chloroethyl, 2-cyanoethyl, 2-hydroxyethyl, 2-(N,N-dimethylamino)ethyl, 2-ethylhexyl, and the like.

The structure represented by $(CR_{231}R_{232})_n$ is preferably —CH_2—, —CH_2CH_2—, or —CH_2CH(CH_3)—, more preferably —CH_2CH_2— or —CH_2CH(CH_3)—, and particularly preferably —CH_2CH_2—.

Each of $R_{233}$ and $R_{234}$ independently represents a hydrogen atom or a substituent. Examples of the substituent include the substituents of the alkyl group represented by $R_2$ and $R_3$ described above.

The structure represented by $(CR_{233}R_{234})_m$ is preferably —CH_2—, —CH_2CH_2—, —CH_2CH(CH_3)—, —CH_2CH_2CH_2—, —CH_2CH(OH)CH_2—, or —CH_2CH(CH_2OH)—, more preferably —CH_2—, —CH_2CH_2—, —CH_2CH(OH)CH_2—, or —CH_2CH_2CH_2—, and particularly preferably —CH_2— or —CH_2CH_2—.

$Y_2$ represents a single bond, —CO—, or —COO—.

When $Y_2$ represents a single bond or —CO—, n represents 0, and m represents an integer of 0 to 6. Particularly, m preferably represents 0 to 4 and more preferably represents 1 to 2.

When $Y_2$ represents —COO—, n represents 1 or 2 and preferably represents 2. m represents an integer of 1 to 6, preferably represents 1 to 4, and more preferably represents 1 to 2.

Rf$_2$ represents a linear or branched perfluoroalkylene group having 1 to 20 carbon atoms or a linear or branched perfluoroether group having 1 to 20 carbon atoms.

The perfluoroalkylene group has 1 to 20 carbon atoms, preferably has 2 to 15 carbon atoms, and even more preferably has 3 to 12 carbon atoms. Specific examples of the perfluoroalkylene group include —C$_4$F$_8$—, —C$_5$F$_{10}$—, —C$_6$F$_{12}$—, —C$_7$F$_{14}$—, —C$_8$F$_{16}$—, —C$_9$F$_{18}$—, —C$_{10}$F$_{20}$—, —C$_{12}$F$_{24}$—, and the like.

The perfluoroether group means a group formed as a result of inserting an ethereal oxygen atom (—O—) between carbon-carbon atoms at one or more sites in the aforementioned perfluoroalkylene group or inserting an ethereal oxygen atom into the binding terminal of the perfluoroalkylene group. The perfluoroether group has 1 to 20 carbon atoms, preferably has 2 to 15 carbon atoms, and more preferably has 3 to 12 carbon atoms. Specific examples of the perfluoroether group include a perfluoroether group represented by —(C$_g$F$_{2g}$O)$_h$— (in the formula, each g independently represents an integer of 1 to 20; h represents an integer of equal to or greater than 1; and g and h satisfy a relationship of g×h≤20).

p represents an integer of 2 to 3; l represents an integer of 0 to 1; and p and l satisfy a relationship of p+l=3. Particularly, p is preferably 3, and l is preferably 0.

Specific examples of the compound represented by Formula (23) will be shown below, but the present invention is not limited thereto.

(Polymer compound (X))

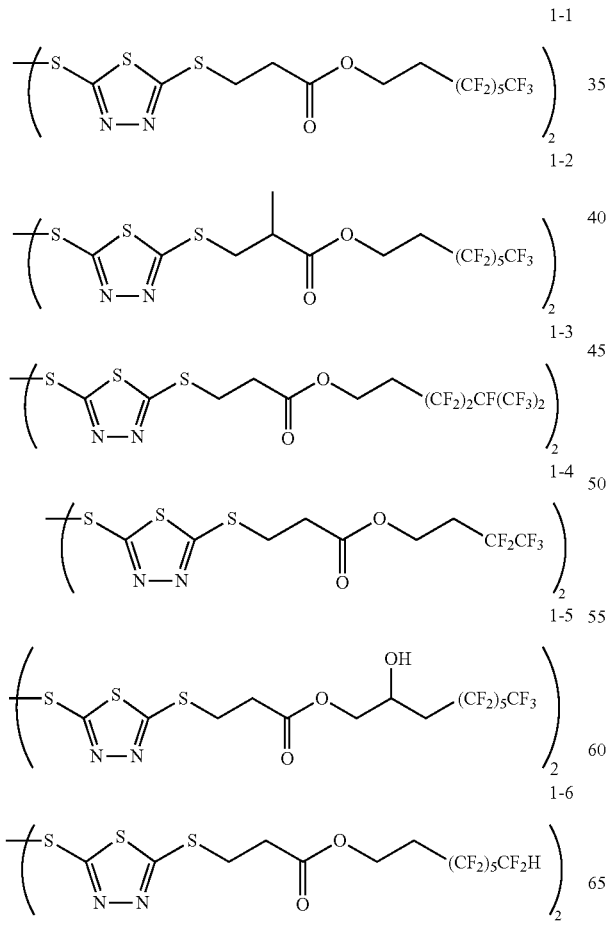

The polymer compound (X) is a polymer compound containing a repeating unit represented by the following Formula (A). The polymer compound (X) has a specific group (A in Formula (A)), which has a migration inhibition ability, on a side chain.

The polymer compound (X) may contain a repeating unit other than the repeating unit represented by Formula (A). The proportion of the repeating unit represented by Formula (A) in the polymer compound (X) is preferably equal to or greater than 5% by mass, more preferably equal to or greater than 10% by mass, even more preferably equal to or greater than 20% by mass, still more preferably equal to or greater than 30% by mass, and most preferably equal to or greater than 50% by mass.

A plurality of repeating units represented by Formula (A) that is contained in the polymer compound (X) may be the same as or different from each other.

Formula (A)

In Formula (A), R$_A$ represents a hydrogen atom or an alkyl group having 1 to 4 carbon atoms that may have a substituent. Among these, a hydrogen atom or a methyl group is preferable.

L$_A$ represents a single bond or a divalent organic group. Examples of the divalent organic group include a linear, branched, or cyclic divalent aliphatic hydrocarbon group (for example, an alkylene group such as a methylene group, an ethylene group, or a propylene group), a linear, branched, or cyclic divalent aromatic hydrocarbon group (for example, a phenylene group), —O—, —S—, —SO$_2$—, —NR$_{222}$—, —CO—, —NH—, —COO—, —CONR$_{222}$—, —O—CO—O—, —SO$_3$—, —NHCOO—, —SO$_2$NR$_{222}$—, —NH—CO—NH—, a group which is obtained by combining a plurality of these (for example, an alkyleneoxy group, an alkyleneoxycarbonyl group, or an alkylenecarbonyloxy group), and the like. R$_{222}$ represents a hydrogen atom or an alkyl group having 1 to 5 carbon atoms.

As a preferred embodiment of L$_A$, a divalent organic group represented by the following Formula (A-1) is exemplified.

Formula (A-1)

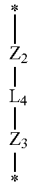

In Formula (A-1), Z$_2$ represents a single bond, an ester group (—COO—), an amide group (—CONR$_{222}$—), or an ether group (—O—). The definition of R$_{222}$ is as described above.

In Formula (A-1), L$_4$ represents a single bond or a divalent organic group. The divalent organic group is preferably a linear, branched, or cyclic divalent aliphatic hydrocarbon group (for example, an alkylene group such as a methylene group, an ethylene group, or a propylene group), a linear, branched, or cyclic divalent aromatic hydrocarbon group (for example, a phenylene group), or a group which is obtained by combining these. The group which is obtained by combining the aforementioned groups may be a group in which the aforementioned groups are combined with each other through an ether group (—O—), an ester group (—COO—), an amide group (—CONR$_{222}$—), a urethane group (—NHCOO—), or a urea group (—NH—CO—NH—). The definition of R$_{222}$ is as described above.

The number of total carbon atoms in L$_4$ is preferably 1 to 15. Herein, the number of total carbon atoms means the number of total carbon atoms contained in L$_4$.

Specific examples of L$_4$ include a methylene group, an ethylene group, a propylene group, a butylene group, a phenylene group, a group formed as a result of substituting these groups with a methoxy group, a hydroxyl group, a chlorine atom, a bromine atom, a fluorine atom, or the like, a group which is obtained by combining these, and the like.

In Formula (A-1), Z$_3$ represents a single bond, —CO$_2$—, —CO—, —O—CO—O—, —SO$_3$—, —CONR$_{222}$—, —NHCOO—, —O—, —S—, SO$_2$NR$_{222}$—, or —NR$_{222}$—. The definition of R$_{222}$ is as described above.

In Formula (A-1), * on the upper side (* adjacent to Z$_2$) represents a position where the divalent organic group is bonded to a carbon atom to which R$_A$ in Formula (A) is bonded.

In Formula (A-1), * on the lower side (* adjacent to Z$_3$) represents a position where the divalent organic group is bonded to A in Formula (A).

That is, when L$_A$ is a divalent organic group represented by Formula (A-1), Formula (A) is represented by the following Formula (A-2).

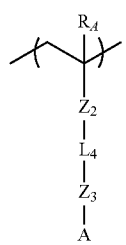

Formula (A-2)

In Formula (A-2), the definition and the preferred embodiment of R$_A$ are the same as those of R$_A$ in Formula (A) described above.

In Formula (A-2), the definition, the specific examples, and the preferred embodiment of each of Z$_2$, L$_4$, and Z$_3$ are the same as those of each of Z$_2$, L$_4$, and Z$_3$ in Formula (A-1) described above.

In Formula (A-2), the definition and the preferred embodiment of A are the same as those of A in Formula (A) which will be described later.

In Formula (A), A represents a monovalent group, which is formed as a result of removing one hydrogen atom (here, a hydrogen atom of a hydroxyl group is excluded) from the compounds represented by Formulae (1) to (8), or a monovalent group which is formed as a result of removing one fluorine atom from a compound that belongs to the compounds represented by Formulae (1) to (8) and has two or more fluorine atoms in a molecule. Herein, the "monovalent group which is formed as a result of removing one hydrogen atom (here, a hydrogen atom of a hydroxyl group is excluded) from compounds represented by Formulae (1) to (8)" means a monovalent group formed as a result of removing any one hydrogen atom, which is other than a hydrogen atom of a hydroxyl group, among hydrogen atoms contained in the compounds represented by Formulae (1) to (8). Furthermore, the "monovalent group which is formed as a result of removing one fluorine atom from a compound that belongs to the compounds represented by Formulae (1) to (8) and has two or more fluorine atoms in a molecule" means a monovalent group formed as a result of removing any one fluorine atom from fluorine atoms contained in a compound which belongs to the compounds represented by Formulae (1) to (8) and has two or more fluorine atoms in a molecule. The group represented by A has a migration inhibition ability.

In the compounds represented by Formulae (1) to (8) described above, the position where a hydrogen atom is removed is not particularly limited. However, in view of further improving the migration inhibition ability, for example, the position is preferably any of R$_1$ to R$_{12}$ in the compounds represented by Formulae (1) to (4), Z in the compound represented by Formula (5), R$_{61}$ or R$_{62}$ in the compound represented by Formula (6), R$_{71}$ or R$_{72}$ in the compound represented by Formula (7), and Z1 or Z2 in the compound represented by Formula (8). In other words, L$_A$ in Formula (A) is preferably bonded to any of R$_1$ to R$_{12}$ in the compounds represented by Formulae (1) to (4), Z in the compound represented by Formula (5), R$_{61}$ or R$_{62}$ in the compound represented by Formula (6), R$_{71}$ or R$_{72}$ in the compound represented by Formula (7), and Z1 or Z2 in the compound represented by Formula (8).

In a case in which a fluorine atom is removed from a compound which belongs to the compounds represented by Formulae (1) to (8) described above and has two or more fluorine atoms in a molecule, the position where the fluorine atom is removed is the same as the position where a hydrogen atom is removed.

Furthermore, A may be a monovalent group, which is formed as a result of removing one hydrogen atom (here, a hydrogen atom of a hydroxyl group is excluded) from compounds represented by Formulae (22) to (24), Formulae (31) to (46), Formulae (51) to (54), Formula (X1), and Formula (Y1) that are preferred embodiments of the compounds represented by Formulae (1) to (8) described above, or a monovalent group formed as a result of removing one fluorine atom from a compound which belongs to the aforementioned compounds and has two or more fluorine atoms in a molecule.

(Synthesis Method of Polymer Compound (X))

Hereinafter, the synthesis method of the polymer compound (X) of the present invention having a specific group (A in Formula (A)), which has a migration inhibition site (anti-migration site), on a side chain will be described.

The synthesis method of the polymer compound (X) is not particularly limited, and examples thereof include the following methods i) and ii).

i) A method of polymerizing a monomer which is represented by Formula (A-3) and has a specific group (A in Formula (A)) having a migration inhibition site

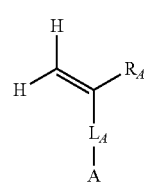

Formula (A-3)

i) A method of introducing a specific group having a migration inhibition site into a polymer compound having a reactive group by reacting the polymer compound with a compound having a group, which can react with the reactive group in the polymer compound, and a specific group having a migration inhibition site Among these, from the viewpoint of synthesis suitability, the method i) is preferable.

As described above, the specific group having a migration inhibition site may be introduced into the polymer compound by polymerizing a monomer, which contains the specific group having a migration inhibition site in the form of a pendant, or may be introduced into the polymer compound by being added to or substituting a portion of the reactive group-containing polymer synthesized in advance.

The polymer compound (X) which can be preferably used in the present invention may contain a copolymerization component other than the unit represented by Formula (A). In the aforementioned synthesis method, the specific group can be introduced into the polymer compound by additionally copolymerizing other monomers. As long as the effects of the present invention are not impaired, any monomer can be used.

Specific examples of other usable monomers include unsubstituted (meth)acrylic acid esters such as methyl (meth)acrylate, butyl (meth)acrylate, hexyl (meth)acrylate, 2-ethylhexyl (meth)acrylate, cyclohexyl (meth)acrylate, benzyl (meth)acrylate, and stearyl (meth)acrylate, halogen-substituted (meth)acrylic acid esters such as 2,2,2-trifluoroethyl (meth)acrylate, 3,3,3-trifluoropropyl (meth)acrylate, 2-(perfluorohexyl)ethyl acrylate, and 2-chloroethyl (meth)acrylate, (meth)acrylamides such as butyl (meth)acrylamide, isopropyl (meth)acrylamide, octyl (meth)acrylamide, 2-ethylhexyl acrylamide, and dimethyl (meth)acrylamide, styrenes such as styrene and α-methylstyrene, vinyl compounds such as N-vinylcarbazole, vinyl acetate, N-vinylacetamide, and N-vinylcaprolactam, dimethylaminoethyl (meth)acrylate, diethylaminoethyl (meth)acrylate, 2-ethylthio-ethyl (meth)acrylate, (meth)acrylic acid, 2-hydroxyethyl (meth)acrylate, and the like. Furthermore, macromonomers obtained by using the aforementioned monomers can also be used.

The polymer compound having a reactive group that is used in the synthesis method ii) described above is synthesized by radically polymerizing a monomer having a reactive group for introducing the specific group having a migration inhibition site into the polymer compound. Examples of the monomer having a reactive group for introducing the specific group having a migration inhibition site include monomers having a carboxyl group, a hydroxyl group, an epoxy group, or an isocyanate group as the reactive group.

Examples of the monomer containing a carboxyl group include (meth)acrylic acid, itaconic acid, vinyl benzoate, Aronix M-5300, M-5400, and M-5600 manufactured by TOAGOSEI CO., LTD., acrylesters PA and HH manufactured by Mitsubishi Rayon Co., Ltd., light acrylate HOA-HH manufactured by KYOEISHA CHEMICAL Co., LTD., NK esters SA and A-SA manufactured by SHIN-NAKAMURA CHEMICAL CO., LTD., and the like.

As the monomer containing a hydroxyl group, it is possible to use 2-hydroxyethyl (meth)acrylate, 4-hydroxybutyl (meth)acrylate, 2-hydroxypropyl (meth)acrylate, 2-hydroxybutyl (meth)acrylate, 1-(meth)acryloyl-3-hydroxyadamantane, hydroxymethyl (meth)acrylamide, 2-(hydroxymethyl)-(meth)acrylate, methyl ester of 2-(hydroxymethyl)-(meth)acrylate, 3-chloro-2-hydroxypropyl (meth)acrylate, 3,5-dihydroxypentyl (meth)acrylate, 1-hydroxymethyl-4-(meth)acryloylmethyl-cyclohexane, 2-hydroxy-3-phenoxypropyl (meth)acrylate, 1-methyl-2-acryloyloxypropyl phthalate, 2-acryloyloxyethyl-2-hydroxyethyl phthalate, 1-methyl-2-acryloyloxyethyl-2-hydroxypropyl phthalate, 2-acryloyloxyethyl-2-hydroxy-3-chloropropyl phthalate, Aronix M-554, M-154, M-555, M-155, and M-158 manufactured by TOAGOSEI CO., LTD., Blemmer PE-200, PE-350, PP-500, PP-800, PP-1000, 70PEP-350B, and 55PET800 manufactured by NOF CORPORATION, and lactone-modified acrylate having the following structure.

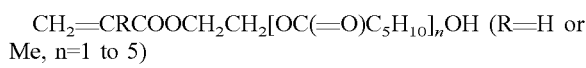
CH$_2$=CRCOOCH$_2$CH$_2$[OC(=O)C$_5$H$_{10}$]$_n$OH (R=H or Me, n=1 to 5)

As the monomer having an epoxy group, it is possible to use glycidyl (meth)acrylate, Cyclomer A and M manufactured by DAICEL CORPORATION, and the like.

As the monomer having an isocyanate group, it is possible to use Karenz AOI and MOI manufactured by SHOWA DENKO K.K.

In the synthesis method ii) described above, as the compound having a specific group having a migration inhibition site that is reacted with the polymer compound having a reactive group, it is possible to use a compound having functional groups combined as below, although the compound varies with the type of the reactive group in the polymer compound.

That is, examples of the combination of (the reactive group of the polymer, the compound having a specific group having a migration inhibition site) include combinations of (a carboxyl group, a carboxyl group), (a carboxyl group, an epoxy group), (a carboxyl group, an isocyanate group), (a carboxyl group, benzyl halide), (a hydroxyl group, a carboxyl group), (a hydroxyl group, an epoxy group), (a hydroxyl group, an isocyanate group), (a hydroxyl group, benzyl halide), (an isocyanate group, a hydroxyl group), (an isocyanate group, a carboxyl group), (an epoxy group, a carboxyl group), and the like.

Specifically, as the monomer having the aforementioned functional groups, it is possible to use acrylic acid, glycidyl acrylate, Cyclomer A (manufactured by DAICEL CORPORATION), Karenz AOI (manufactured by SHOWA DENKO K.K.), methacrylic acid, glycidyl methacrylate, Cyclomer M (manufactured by DAICEL CORPORATION), and Karenz MOI (manufactured by SHOWA DENKO K.K.).

Specific examples of the polymer compound (X) in the present invention will be shown below, but the present invention is not limited thereto.

(X-1)
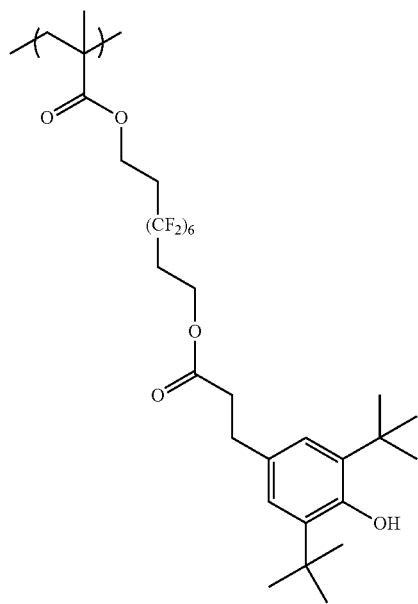
(X-2)
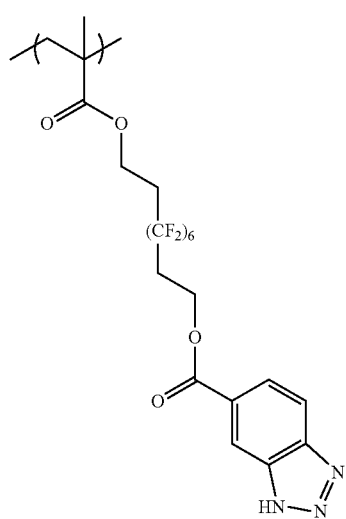
(X-3)
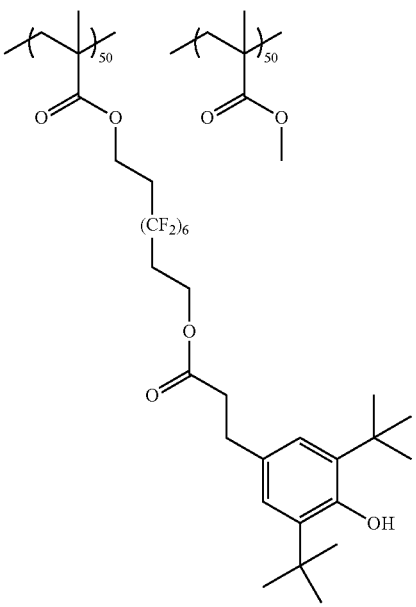
(X-4)
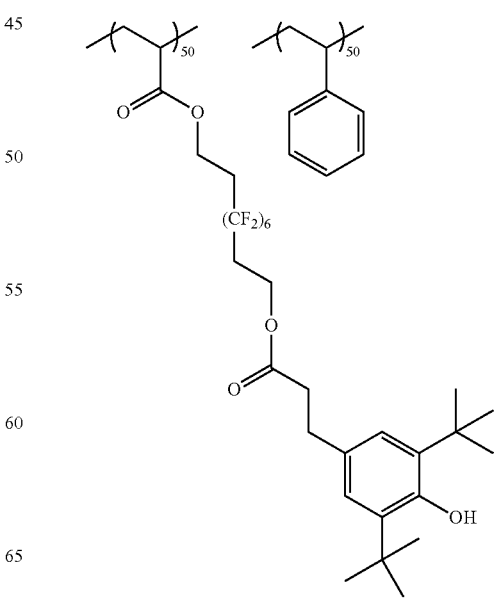

-continued

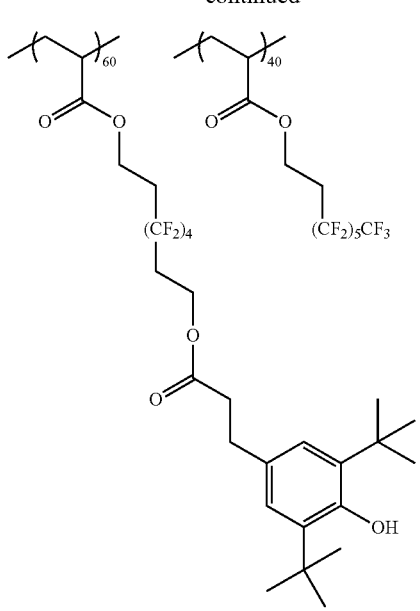

(X-5)

(Polymer Compound (Y))

The polymer compound (Y) is a polymer compound having a repeating unit represented by the following Formula (B) and a repeating unit represented by the following Formula (C). The polymer compound (Y) has a specific group (B in Formula (B)), which has a migration inhibition ability, on a side chain and contains a fluorine atom in the repeating unit represented by Formula (C).

The proportion of the repeating unit represented by Formula (B) in the polymer compound (Y) is preferably 5% by mass to 95% by mass, and more preferably 20% by mass to 80% by mass.

The proportion of the repeating unit represented by Formula (C) in the polymer compound (Y) is preferably 5% by mass to 95% by mass, and more preferably 20% by mass to 80% by mass.

A plurality of repeating units represented by Formulae (B) and (C) that is contained in the polymer compound (Y) may be the same as or different from each other.

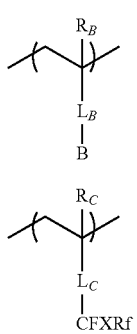

Formula (B)

Formula (C)

The definition of $R_B$ and $L_B$ in Formula (B) is the same as that of $R_A$ and $L_A$ in Formula (A) described above, and the preferred embodiment thereof is also the same.

B in Formula (B) represents a monovalent group, which is formed as a result of removing one hydrogen atom (here, a hydrogen atom of a hydroxyl group is excluded) from compounds represented by Formulae (Y-1) to (Y-8) which will be described later, or a group represented by the following Formula (25). Herein, the "monovalent group, which is formed as a result of removing one hydrogen atom (here, a hydrogen atom of a hydroxyl group is excluded) from compounds represented by Formulae (Y-1) to (Y-8)" means a monovalent group formed as a result of removing any one hydrogen atom, which is other than a hydrogen atom of a hydroxyl group, among hydrogen atoms contained in the compounds represented by Formulae (Y-1) to (Y-8). The group represented by B has a migration inhibition ability.

$$P—(CR_1=Y)_n-Q \qquad \text{Formula (Y-1)}$$

$$R_7—C(=O)—H \qquad \text{Formula (Y-2)}$$

$$Z—SH \qquad \text{Formula (Y-5)}$$

$$Z1-S—S—Z2 \qquad \text{Formula (Y-8)}$$

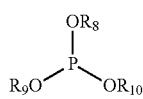

Formula (Y-3)

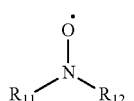

Formula (Y-4)

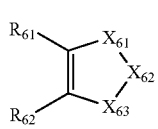

Formula (Y-6)

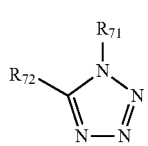

Formula (Y-7)

The definition of each of the groups in Formulae (Y-1) to (Y-8) is the same as the definition of each of the groups in Formulae (1) to (8) described above.

A difference between the compounds represented by Formulae (Y-1) to (Y-8) and the compounds represented by Formulae (1) to (8) is as follows. In the aforementioned groups in the compounds represented by Formulae (1) to (8), a portion of hydrogen atoms or the entirety of hydrogen atoms are substituted with a fluorine atom, but in the compounds represented by Formulae (Y-1) to (Y-8), hydrogen atoms are not substituted with fluorine atoms. Herein, the compounds represented by Formulae (Y-1) to (Y-8) may contain fluorine atoms.

Just like Formula (1) described above, the compounds represented by Formulae (31) to (46) are exemplified as preferred embodiments of Formula (Y-1). However, in this case, hydrogen atoms may or may not be substituted with fluorine atoms. More specifically, the compounds represented by Formulae (31) to (46) are as below.

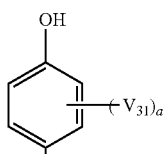

Formula (31)

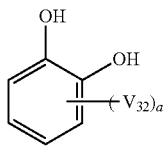

Formula (32)

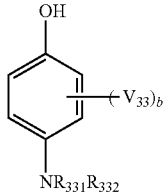

Formula (33)

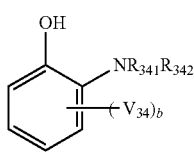

Formula (34)

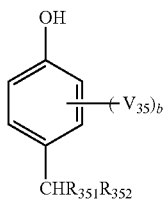

Formula (35)

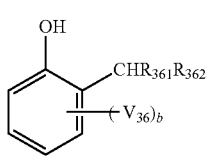

Formula (36)

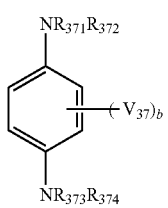

Formula (37)

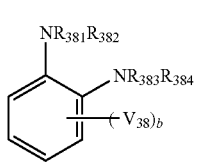

Formula (38)

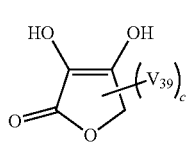

Formula (39)

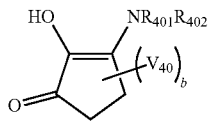

Formula (40)

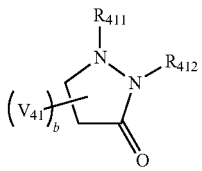

Formula (41)

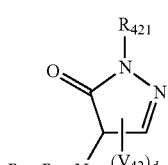

Formula (42)

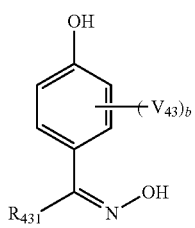

Formula (43)

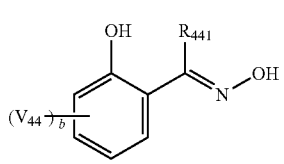

Formula (44)

$R_{451}R_{452}N-NR_{453}R_{454}$

Formula (45)

$R_{461}R_{462}N-OH$

Formula (46)

In Formula (31), $V_{31}$ represents a substituent, and a represents an integer of 1 to 4.

In Formula (32), $V_{32}$ represents a substituent, and a represents an integer of 1 to 4.

In Formula (33), $V_{33}$ represents a substituent; each of $R_{331}$ and $R_{332}$ independently represents a hydrogen atom or a group which can be substituted with a nitrogen atom; and b represents an integer of 0 to 4.

In Formula (34), $V_{34}$ represents a substituent; each of $R_{341}$ and $R_{342}$ independently represents a hydrogen atom or a group which can be substituted with a nitrogen atom; and b represents an integer of 0 to 4.

In Formula (35), $V_{35}$ represents a substituent; each of $R_{351}$ and $R_{352}$ independently represents a hydrogen atom or substituent; and b represents an integer of 0 to 4.

In Formula (36), $V_{36}$ represents a substituent; each of $R_{361}$ and $R_{362}$ independently represents a hydrogen atom or a substituent; and b represents an integer of 0 to 4.

In Formula (37), $V_{37}$ represents a substituent; each of $R_{371}$, $R_{372}$, $R_{373}$, and $R_{374}$ independently represents a hydrogen atom or a group which can be substituted with a nitrogen atom; and b represents an integer of 0 to 4.

In Formula (38), $V_{38}$ represents a substituent; each of $R_{381}$, $R_{382}$, $R_{383}$, and $R_{384}$ independently represents a hydrogen atom or a group which can be substituted with a nitrogen atom; and b represents an integer of 0 to 4.

In Formula (39), $V_{39}$ represents a substituent; and c represents an integer of 1 or 2.

In Formula (40), $V_{40}$ represents a substituent; each of $R_{401}$ and $R_{402}$ independently represents a hydrogen atom or a group which can be substituted with a nitrogen atom; and b represents an integer of 0 to 4.

In Formula (41), $V_{41}$ represents a substituent; each of $R_{411}$ and $R_{412}$ independently represents a hydrogen atom or a group which can be substituted with a nitrogen atom; and b represents an integer of 0 to 4.

In Formula (42), $V_{42}$ represents a substituent; each of $R_{421}$, $R_{422}$, and $R_{423}$ independently represents a hydrogen atom or a group which can be substituted with a nitrogen atom; and d represents 0 or 1.

In Formula (43), $V_{43}$ represents a substituent; $R_{431}$ represents a hydrogen atom or a substituent; and b represents an integer of 0 to 4.

In Formula (44), $V_{44}$ represents a substituent; $R_{441}$ represents a hydrogen atom or a substituent; and b represents an integer of 0 to 4.

In Formula (45), each of $R_{451}$, $R_{452}$, $R_{453}$, and $R_{454}$ represents a hydrogen atom or a group which can be substituted with a nitrogen atom.

In Formula (46), each of $R_{461}$ and $R_{462}$ independently represents a hydrogen atom or a group which can be substituted with a nitrogen atom.

In the compounds represented by Formula (Y-1) to (Y-8) described above, the position where a hydrogen atom is removed is not particularly limited. However, in view of further improving the migration inhibition ability, for example, the position is preferably any of $R_1$ to $R_{12}$ in the compounds represented by Formulae (Y-1) to (Y-4), Z in the compound represented by Formula (Y-5), $R_{61}$ or $R_{62}$ in the compound represented by Formula (Y-6), $R_{71}$ or $R_{72}$ in the compound represented by Formula (Y-7), and Z1 or Z2 in the compound represented by Formula (Y-8). In other words, $L_A$ in Formula (A) is preferably bonded to any of $R_1$ to $R_{12}$ in the compounds represented by Formulae (Y-1) to (Y-4), Z in the compound represented by Formula (Y-5), $R_{61}$ or $R_{62}$ in the compound represented by Formula (Y-6), $R_{71}$ or $R_{72}$ in the compound represented by Formula (Y-7), and Z1 or Z2 in the compound represented by Formula (Y-8).

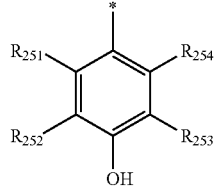

Formula (25)

In Formula (25), each of $R_{251}$, $R_{252}$, $R_{253}$, and $R_{254}$ independently represents a hydrogen atom or a substituent. Examples of the substituent include the substituents of the alkyl group represented by $R_2$ and $R_3$ described above. Among the substituents, an alkyl group, an alkoxy group, and a hydroxy group are preferable as the substituent because these exert a small influence on the mobility and further improve the mobility. Particularly, either or both of $R_{252}$ and $R_{253}$ preferably represent an alkyl group or an alkoxy group. As the alkyl group, a methyl group, an ethyl group, an isopropyl group, a t-butyl group, a t-amyl group, or the like is preferable. As the alkoxy group, a methoxy group, an ethoxy group, or the like is particularly preferable.

Either or both of $R_{252}$ and $R_{253}$ more preferably represent an alkyl group having 2 to 5 carbon atoms, even more preferably represent an ethyl group, an i-propyl group, a t-butyl group, or a t-amyl group, and most preferably represent a t-butyl group. Each of $R_{251}$ and $R_{254}$ preferably represents a hydrogen atom.

* represents a position where the compound is bonded to $L_B$ in Formula (B).

The definition of $R_C$ and $L_C$ in Formula (C) is the same as that of $R_A$ and $L_A$ in Formula (A) described above, and the preferred embodiment thereof is also the same.

As a preferred embodiment of $L_C$, a divalent organic group represented by —$Z_4$-$L_5$- is exemplified.

Each $Z_4$ independently represents a single bond, an ester group (—COO—), an amide group (—CONR$_{271}$—), or an ether group (—O—). Herein, $R_{271}$ preferably represents a hydrogen atom or an alkyl group having 1 to 5 carbon atoms.

$L_5$ represents a single bond or a divalent organic group having 1 to 6 carbon atoms that does not contain a fluorine atom. Examples of the divalent organic group include groups having 1 to 6 carbon atoms that do not contain a fluorine atom, among the groups described as $L_4$.

X represents a hydrogen atom, a fluorine atom, or a trifluoromethyl group.

Rf represents a fluoroalkyl group having 20 or less carbon atoms that may have an ethereal oxygen atom, in which at least one hydrogen atom is substituted with a fluorine atom. Alternatively, Rf represents a fluorine atom.

Specific examples of the polymer compound (Y) will be shown below, but the present invention is not limited thereto.

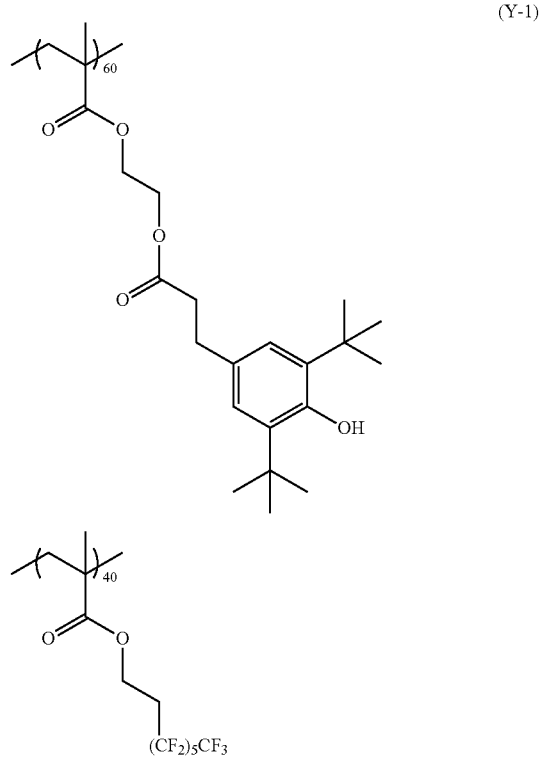

(Y-1)

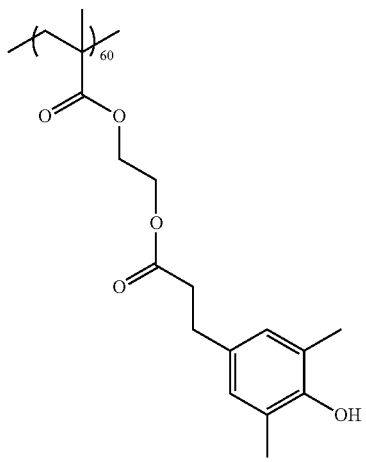
(Y-2)

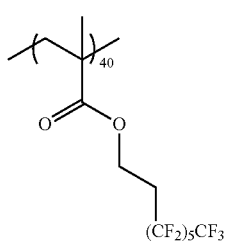

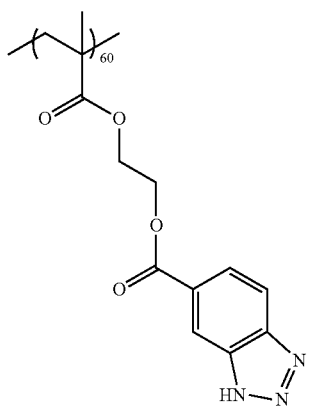
(Y-3)

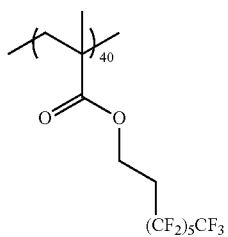

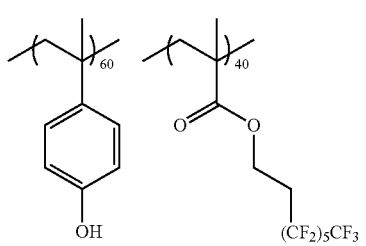
(Y-4)

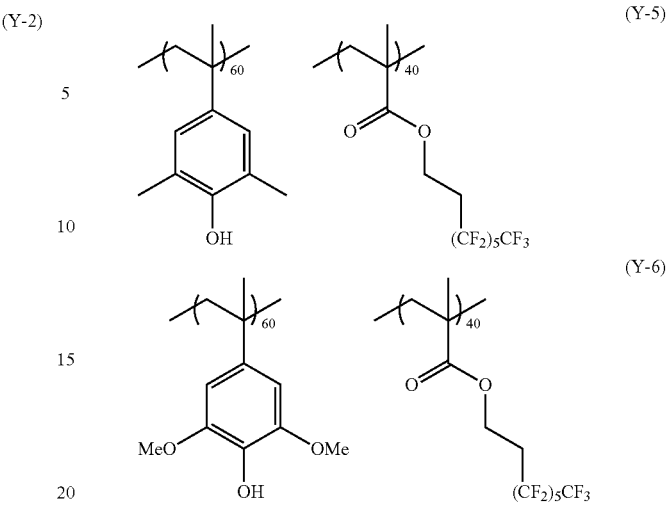
(Y-5)

(Y-6)

In the composition of the present invention, the total content of the F-containing migration inhibitor is not particularly limited. However, the total content of the F-containing migration inhibitor is preferably 0.1% by mass to 20% by mass, and more preferably 1% by mass to 10% by mass, with respect to the total mass of the insulating material.

The composition of the present invention may contain components other than the insulating material and the F-containing migration inhibitor. For example, from the viewpoint of the homogeneity of the gate insulating film to be formed and from the viewpoint of the flatness at the time of forming the film, the composition preferably contains a solvent.

The solvent is not particularly limited, and preferred examples thereof include aromatic compounds such as toluene, xylene, mesitylene, 1,2,3,4-tetrahydronaphthalene (tetralin), chlorobenzene, dichlorobenzene, and anisole, glycol ether-based compounds such as propylene glycol monoethyl ether acetate, propylene glycol monoethyl ether, and diethylene glycol monoethyl ether acetate, ketone-based compounds such as methyl ethyl ketone and methyl isobutyl ketone, and the like.

As described above, the composition of the present invention exhibits excellent characteristics. Therefore, the composition of the present invention is preferable as a composition for forming a gate insulating film of an organic thin film transistor.

<Organic Thin Film Transistor>

The organic thin film transistor of the present invention is an organic thin film transistor having a gate insulating film formed of the aforementioned composition of the present invention. Particularly, the organic thin film transistor is preferably a bottom contact-type organic thin film transistor illustrated in FIG. 1 described above. The organic thin film transistor is applicable to electronic paper, a display device, or the like.

Hereinafter, each of the members of the organic thin film transistor will be specifically described.

(Gate Insulating Film)

The gate insulating film is a film formed by using the aforementioned composition of the present invention.

The method for forming the gate insulating film is not particularly limited. Examples of the method include a method of coating a substrate, on which a gate electrode has been formed, with the composition of the present invention and performing heating, and drying treatments on the resultant if necessary.

The method for coating the substrate with the composition for forming a gate insulating film is not particularly limited, and it is possible to use a known method (a bar coating method, a spin coating method, a knife coating method, or a doctor blade method).

The film thickness of the gate insulating film is not particularly limited but is preferably 100 nm to 1,000 nm.

<Substrate>

The substrate plays a role of supporting the gate electrode, the source electrode, the drain electrode, and the like which will be described later.

The type of the substrate is not particularly limited, and examples thereof include a plastic substrate, a glass substrate, a ceramic substrate, and the like. Among these, from the viewpoint of the applicability to various devices and from the viewpoint of the cost, a glass substrate or a plastic substrate is more preferable.

Examples of the material of the plastic substrate include a thermosetting resin (for example, an epoxy resin, a phenol resin, a polyimide resin, or a polyester resin) and a thermoplastic resin (for example, a phenoxy resin, polyethersulfone, polysulfone, or polyphenylene sulfone).

Examples of the material of the ceramic substrate include alumina, aluminum nitride, zirconia, silicon, silicon nitride, silicon carbide, and the like.

Examples of the material of the glass substrate include soda glass, potash glass, borosilicate glass, quartz glass, aluminosilicate glass, lead glass, and the like.

<Gate Electrode>

Examples of the material of the gate electrode include a metal such as gold (Au), aluminum, copper, chromium, nickel, cobalt, titanium, platinum, magnesium, calcium, barium, or sodium; a conductive oxide such as $InO_2$, $SnO_2$, or ITO; a conductive polymer such as polyaniline, polypyrrole, polythiophene, polyacetylene, or polydiacetylene; a semiconductor such as silicon, germanium, or gallium arsenide; a carbon material such as fullerene, carbon nanotubes, or graphite; and the like. Among these, a metal is preferable, and aluminum is more preferable.

The thickness of the gate electrode is not particularly limited but is preferably 20 nm to 200 nm.

The method for forming the gate electrode is not particularly limited. Examples of the method include a method of vacuum vapor-depositing or sputtering an electrode material onto a substrate, a method of coating a substrate with a composition for forming an electrode, a method of printing a composition for forming an electrode on a substrate, and the like. Furthermore, when the electrode is patterned, examples of the patterning method include a photolithography method; a printing method such as ink jet printing, screen printing, offset printing, or relief printing; a mask vapor deposition method; and the like.

<Source Electrode and Drain Electrode>

Specific examples of the material of the source electrode and the drain electrode are the same as the examples of the material of the gate electrode described above. Among the materials, a metal is preferable. Furthermore, copper, silver, or gold is preferable because these are excellent in conductivity, and silver is more preferable because the performance and cost are balanced well. Particularly, in the present invention, even when silver, which is a metal that easily causes migration, is used as an electrode material, migration is inhibited, and the insulation reliability can be secured. Accordingly, an organic semiconductor transistor having excellent performance can be prepared.

The method for forming the source electrode and the drain electrode is not particularly limited. Examples of the method include a method of vacuum vapor-depositing or sputtering an electrode material onto the substrate on which the organic semiconductor layer has been formed, a method of coating the substrate with a composition for forming an electrode, a method of printing the composition for forming an electrode on the substrate, and the like. Specific examples of the patterning method are the same as the examples of the patterning method of the gate electrode described above.

The channel length of the source electrode and the drain electrode is not particularly limited but is preferably 5 µm to 30 µm.

The channel width of the source electrode and the drain electrode is not particularly limited but is preferably 10 µm to 200 µm.

<Organic Semiconductor Layer>

The organic semiconductor layer is a layer composed of an organic semiconductor.

The type of the organic semiconductor contained in the organic semiconductor layer is not particularly limited, and it is possible to use a known material. More specifically, examples of such a material include pentacenes such as 6,13-bis(triisopropylsilylethynyl)pentacene (TIPS pentacene), tetramethyl pentacene, and perfluoropentacene, anthradithiophenes such as TES-ADT and diF-TES-ADT, benzothienobenzothiophenes such as DPh-BTBT and Cn-BTBT, dinaphthothienothiophenes such as Cn-DNTT, dioxaanthanthrenes such as peri-xanthenoxanthene, rubrenes, fullerenes such as C60 and PCBM, phthalocyanines such as copper phthalocyanine and fluorinated copper phthalocyanine, polythiophenes such as P3RT, PQT, and P3HT, polythienothiophenes such as poly[2,5-bis(3-dodecylthiophen-2-yl)thieno[3,2-b]thiophene] (PBTTT), and the like.

The method for forming the organic semiconductor layer is not particularly limited. Examples of the method include a method of coating the substrate, on which the gate electrode, the gate insulating film, the source electrode, and the drain electrode have been formed, with a composition for forming an organic semiconductor layer, and the like. Specific examples of the method of coating the substrate with the composition for forming an organic semiconductor layer are the same as the method of coating the substrate with the composition for forming a gate insulating film. When the organic semiconductor layer is formed by coating the substrate with the composition for forming an organic semiconductor layer, for the purpose of removing the solvent, causing crosslinking, or the like, the composition may be heated (baked) after coating.

The thickness of the organic semiconductor layer is not particularly limited but is preferably 10 nm to 200 nm.

<Sealing Layer>

From the viewpoint of durability, the organic thin film transistor of e present invention preferably includes a sealing layer as the outermost layer. For the sealing layer, a known sealant can be used.

The thickness of the sealing layer is not particularly limited but is preferably 0.2 µm to 10 µm.

The method for forming the sealing layer is not particularly limited. Examples of the method include a method of coating the substrate, on which the gate electrode, the gate insulating film, the source electrode, the drain electrode, and the organic semiconductor layer have been formed, with a composition for forming a sealing layer, and the like. Specific examples of the method of coating the substrate with the composition for forming a sealing layer are the same as the examples of the method of coating the substrate with the composition for forming a gate insulating film. When the sealing layer is formed by coating the substrate with the composition for forming a sealing layer, for the purpose of removing the solvent, causing crosslinking, or the like, the composition may be heated (baked) after coating.

EXAMPLES

Examples will be described below, but the present invention is not limited thereto.

Synthesis Example 1: Synthesis of Migration Inhibitor b-1

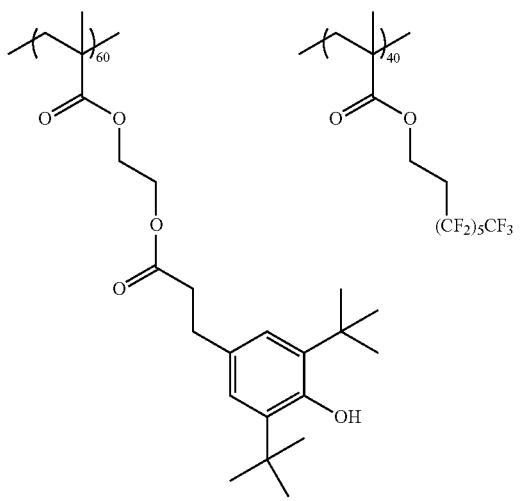

According to the following scheme, a compound M-1 was synthesized.

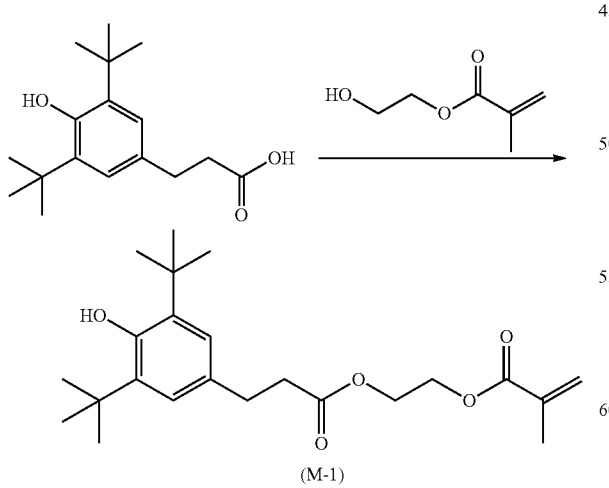

3-(3,5-di-tert-butyl-4-hydroxyphenyl)propionate (4.0 g, 14.4 mmol), dichloromethane (20 ml), 2-hydroxyethyl methacrylate (2.87 g, 14.4 mmol), tetrahydrofuran (10 ml), 1-ethyl-3-(3-dimethylaminopropyl)carbodiimide hydrochloride (2.75 g, 14.4 mmol), and 4-dimethylaminopyridine (0.10 g, 0.72 mmol) were put in this order into a reaction container.

After the reaction solution was stirred for 3 hours at room temperature, 1 N hydrochloric acid (50 ml) was put into the reaction container, and extraction was performed by using 100 ml of ethyl acetate. The organic phase was washed with saturated saline and dried over magnesium sulfate. The solid content was separated by filtration and concentrated under reduced pressure. The concentrate was purified by silica gel column chromatography (mobile phase: hexane/ethyl acetate=8/1), thereby obtaining 3.2 g of the compound M-1 (yield: 58%).

The compound M-1 (3.51 g), 3,3,4,4,5,5,6,6,7,7,8,8,8-tridecafluoro-octyl methacrylate (2.59 g), and 4-methyl-2-pentanone (manufactured by Wako Pure Chemical Industries, Ltd.) (5.1 g) were put into a 100 mL three-neck flask and heated to 80° C. in a nitrogen gas stream. To the resultant, a solution of azobisisobutyronitrile (manufactured by Wako Pure Chemical Industries, Ltd.) (49.3 mg) and 4-methyl-2-pentaone (manufactured by Wako Pure Chemical Industries, Ltd.) (1.0 g) was added, and the resultant was stirred for 16 hours. After the reaction ended, the resultant was cooled to room temperature and diluted with 4-methyl-2-pentanone (manufactured by Wako Pure Chemical Industries, Ltd.) (18.0 g). After reprecipitation was performed by using methanol, the precipitate was dried under reduced pressure, thereby obtaining 4.8 g of a migration inhibitor b-1 (Mw=35,000).

The molecular weight of the migration inhibitor b-1 means a weight average molecular weight which is measured by a gel permeation chromatography (GPC) method and expressed in terms of polystyrene. The weight average molecular weight was measured by the GPC method by dissolving the polymer in tetrahydrofuran and by using high-speed GPC apparatus (HLC-8220GPC) manufactured by TOSOH CORPORATION, TSKgel SuperHZ4000 (manufactured by TOSOH CORPORATION, 4.6 mm I. D.×15 cm) as a column, and tetrahydrofuran (THF) as an eluant.

Synthesis Example 2: Synthesis of Migration Inhibitor b-2

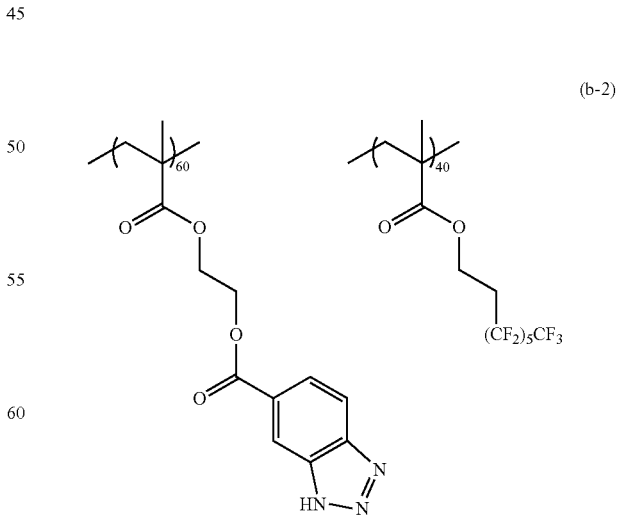

According to the following scheme, a compound M-2 was synthesized.

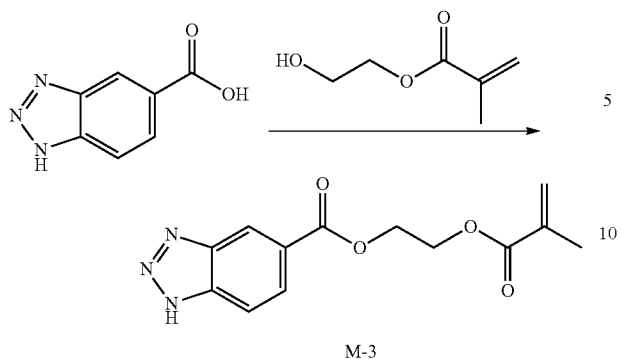

M-3

1H-benzotriazole-5-carboxylic acid (3.0 g, 18.4 mmol), tetrahydrofuran (54 ml), dimethylformamide (6 ml), 2-hydroxyethyl methacrylate (2.39 g, 18.4 mmol), 1-ethyl-3-(3-dimethylaminopropyl)carbodiimide hydrochloride (3.54 g, 18.4 mmol), and 4-dimethylaminopyridine (0.22 g, 0.184 mmol) were put in this order into a reaction container.

After the resultant was stirred for 24 hours at 70° C., water (50 ml) was added thereto, and extraction was performed by using ethyl acetate (100 ml). The organic phase was washed with saturated saline and dried over magnesium sulfate. The solid content was separated by filtration, and then the solution was concentrated under reduced pressure. The concentrate was purified by silica gel column chromatography (mobile phase: hexane/ethyl acetate=2/1), thereby obtaining 3.0 g of the compound M-2 (yield: 59%).

The compound M-2 (2.48 g) 3,3,4,4,5,5,6,6,7,7,8,8,8-tridecafluoro-octyl methacrylate (2.59 g), and 4-methyl-2-pentanone (manufactured by Wako Pure Chemical Industries, Ltd.) (4.1 g) were put into a 100 mL three-neck flask and heated to 80° C. in a nitrogen gas stream. To the resultant, a solution of azobisisobutyronitrile (manufactured by Wako Pure Chemical Industries, Ltd.) (49.3 mg) and 4-methyl-2-pentaone (manufactured by Wako Pure Chemical Industries, Ltd.) (1.0 g) was added, and the resultant was stirred for 16 hours. After the reaction ended, the resultant was cooled to room temperature and diluted with 4-methyl-2-pentanone (manufactured by Wako Pure Chemical Industries, Ltd.) (18.0 g). After reprecipitation was performed by using methanol, the precipitate was dried under reduced pressure, thereby obtaining 4.3 g of a migration inhibitor b-2 (Mw=45,000).

The molecular weight of the migration inhibitor b-2 means a weight average molecular weight which is measured by a gel permeation chromatography (GPC) method and expressed in terms of polystyrene. The weight average molecular weight was measured by the GPC method by dissolving the polymer in tetrahydrofuran and by using high-speed GPC apparatus (HLC-8220GPC) manufactured by TOSOH CORPORATION, TSKgel SuperHZ4000 (manufactured by TOSOH CORPORATION, 4.6 mm I. D.×15 cm) as a column, and tetrahydrofuran (THF) as an eluant.

Synthesis Example 3: Synthesis of Migration Inhibitor b-3 (Compound 33-5)

According to the following scheme, a migration inhibitor b-3 was synthesized.

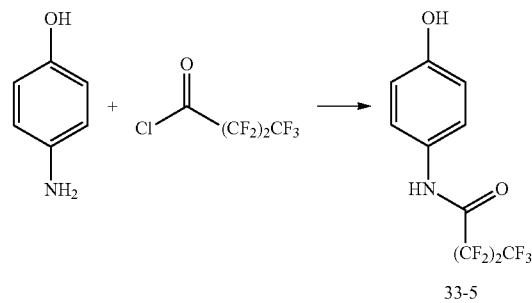

33-5

4-Aminophenol (manufactured by Wako Pure Chemical Industries, Ltd.) (1.96 g, 18.0 mmol), tetrahydrofuran (40 ml), and triethylamine (1.82 g, 18.0 mmol) were put into a reaction container and cooled in an ice bath. Thereafter, heptafluorobutyryl chloride (4.18 g, 18.0 mmol) was added dropwise to the reaction solution from a dropping funnel for 0.5 hours. Thereafter, the reaction solution was stirred for 3 hours at room temperature, 1 N hydrochloric acid (50 ml) was then added to the reaction solution, and extraction was performed by using 100 ml of ethyl acetate. The organic phase was washed with saturated saline and dried over magnesium sulfate. The solid content was separated by filtration and concentrated under reduced pressure, thereby obtaining 5 g of crude crystals. The obtained crystals were purified by silica gel column chromatography (mobile phase: hexane/ethyl acetate), thereby obtaining 4 g of the migration inhibitor b-3 (yield: 73%).

Synthesis Example 4: Synthesis of Migration Inhibitor b-4 (Compound 35-3)

According to the following scheme, a migration inhibitor b-4 was synthesized.

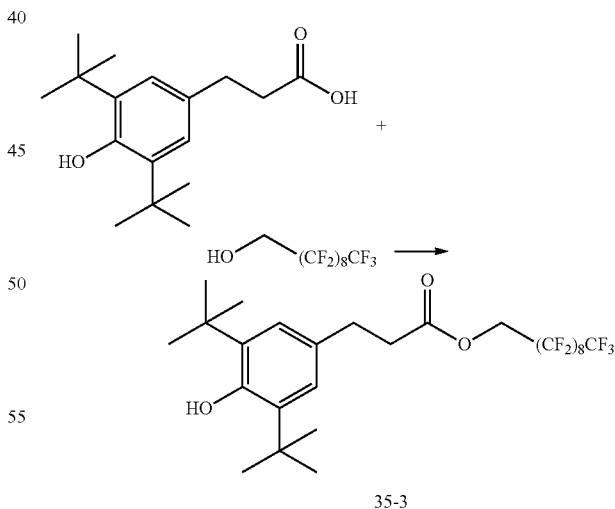

35-3

3-(3,5-di-tert-butyl-4-hydroxyphenyl)propionate (3.5 g, 12.6 mmol), dichloromethane (20 ml), 2,2,3,3,4,4,5,5,6,6,7,7,8,8,9,9,10,10,10-nonadecafluorodecan-1-ol (6.3 g, 12.6 mmol), tetrahydrofuran (10 ml), 1-ethyl-3-(3-dimethylaminopropyl) carbodiimide hydrochloride (2.4 g, 12.6 mmol), and 4-dimethylaminopyridine (0.05 g, 0.4 mmol) were put in this order into a reaction container.

After the reaction solution was stirred for 3 hours at room temperature, a 1 N hydrochloric acid (50 ml) was added to the reaction solution, and extraction was performed by using 100 ml of ethyl acetate. The organic phase was washed with saturated saline and dried over magnesium sulfate. The solid content was separated by filtration and then concentrated under reduced pressure, thereby obtaining white crude crystals. Thereafter, reprecipitation was performed by using methanol, thereby obtaining 6.0 g of the migration inhibitor b-4 (yield: 63%).

<Migration Inhibitor b-5>

As a migration inhibitor b-5 (compound 2-2), pentafluorobenzaldehyde (manufactured by Tokyo Chemical Industry Co., Ltd.) was used.

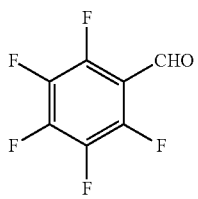

2-2

Synthesis Example 5: Synthesis of Migration Inhibitor b-6 (Compound 3-2)

According to the synthesis example described in Organic Letters, 2009, vol. 11, #9, p. 1879-1881, a migration inhibitor b-6 (compound 3-2) was synthesized.

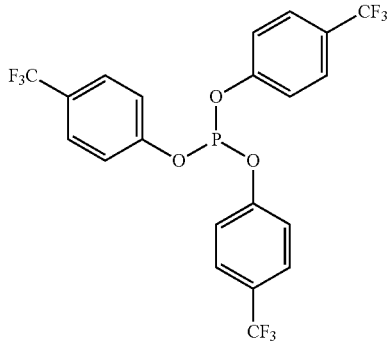

3-2

Synthesis Example 6: Synthesis of Migration Inhibitor b-7 (Compound 4-3)

According to the following scheme, a migration inhibitor b-7 was synthesized.

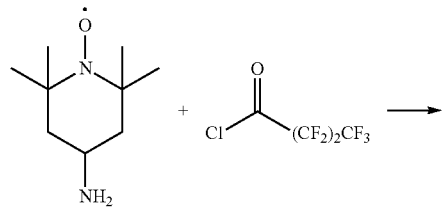

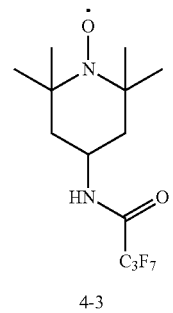

4-3

A 4-amino-2,2,6,6-tetramethylpiperidine 1-oxyl free radical (manufactured by Tokyo Chemical Industry Co., Ltd.) (3.08 g, 18.0 mmol), tetrahydrofuran (40 ml), and triethylamine (1.82 g, 18.0 mmol) were put into a reaction container and cooled in an ice bath. Thereafter, heptafluorobutyryl chloride (4.18 g, 18.0 mmol) was added dropwise to the reaction solution from a dropping funnel for 0.5 hours. Thereafter, the reaction solution was stirred for 3 hours at room temperature, 1 N hydrochloric acid (50 ml) was then added to the reaction solution, and extraction was performed by using 100 ml of ethyl acetate. The organic phase was washed with saturated saline and dried over magnesium sulfate. The solid content was separated by filtration and concentrated under reduced pressure, thereby obtaining 5.5 g of crude crystals. The crystals were purified by silica gel column chromatography (mobile phase: hexane/ethyl acetate), thereby obtaining 5 g of the migration inhibitor b-7 (yield: 76%).

Synthesis Example 7: Synthesis of Migration Inhibitor b-8 (Compound 51-2)

According to the following scheme, a migration inhibitor b-8 was synthesized.

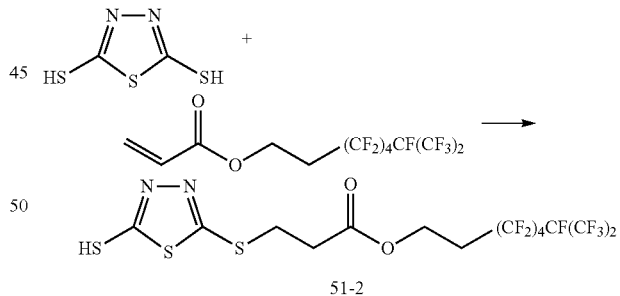

51-2

1,3,4-Thiadiazole-2,5-dithiol (manufactured by Wako Pure Chemical Industries, Ltd.) (4.0 g, 26.6 mmol) and tetrahydrofuran (80 ml) were put into a reaction container and thoroughly dissolved. Thereafter, 3,3,4,4,5,5,6,6,7,8,8,8-dodecafluoro-7-(trifluoromethyl)octyl acrylate (12.5 g, 26.6 mmol) was added dropwise to the reaction container from a dropping funnel for 0.5 hours. After being stirred for 6 hours at 65° C., the reaction solution was cooled to room temperature and concentrated under reduced pressure. 200 mL of hexane was added to the reaction solution, and the resultant was cooled in an ice bath, thereby obtaining 16 g of crude crystals. 8 g of the crude crystals were purified by silica gel column chromatography (mobile phase: hexane/ethyl acetate), thereby obtaining 6 g of the migration inhibitor b-8 (yield: 72%).

Synthesis Example 8: Synthesis of Migration Inhibitor b-9 (Compound 22-1)

According to the following scheme, a migration inhibitor b-9 was synthesized.

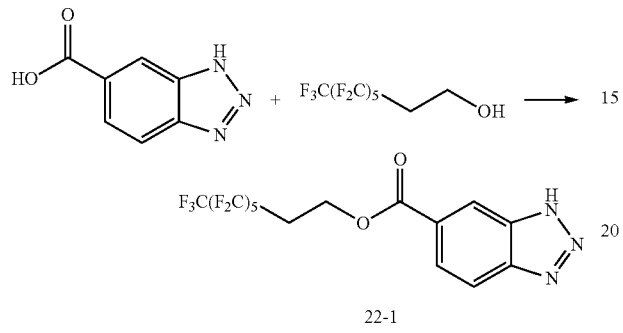

1H-benzotriazole-5-carboxylic acid (3.0 g, 18.4 mmol), tetrahydrofuran (54 ml), dimethylformamide (6 ml), 3,3,4,4,5,5,6,6,7,7,8,8,8-tridecafluoro-1-octanol (6.7 g, 18.4 mmol), 1-ethyl-3-(3-dimethylaminopropyl)carbodiimide hydrochloride (3.54 g, 18.4 mmol), and 4-dimethylaminopyridine (0.22 g, 0.184 mmol) were put in this order into a reaction container.

After the resultant was stirred for 24 hours at 70° C., water (50 ml) was added thereto, and extraction was performed by using ethyl acetate (100 ml). The organic phase was washed with saturated saline and dried over magnesium sulfate. The solid content was separated by filtration, and the solution was concentrated under reduced pressure. The obtained solid content was purified by silica gel column chromatography (mobile phase: hexane/ethyl acetate), thereby obtaining 6.0 g of the migration inhibitor b-9 (yield: 64%).

Synthesis Example 9: Synthesis of Migration Inhibitor b-10 (Compound 7-1)

According to the following scheme, a migration inhibitor b-10 was synthesized.

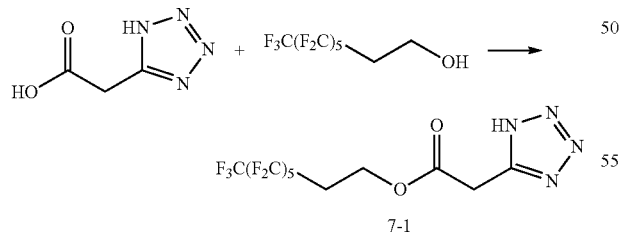

1H-tetrazol-5-acetic acid (2.3 g, 18.4 mmol), tetrahydrofuran (54 ml), dimethylformamide (6 ml), 3,3,4,4,5,5,6,6,7,7,8,8,8-tridecafluoro-1-octanol (6.7 g, 18.4 mmol), 1-ethyl-3-(3-dimethylaminopropyl)carbodiimide hydrochloride (3.54 g, 18.4 mmol), and 4-dimethylaminopyridine (0.22 g, 0.184 mmol) were put in this order into a reaction container.

After the resultant was stirred for 24 hours at 70° C., water (50 ml) was added thereto, and extraction was performed by using ethyl acetate (100 ml). The organic phase was washed with saturated saline and dried over magnesium sulfate. The solid content was separated by filtration, and then the solution was concentrated under reduced pressure. The obtained solid content was purified by silica gel column chromatography (mobile phase: hexane/ethyl acetate), thereby obtaining 5.0 g of the migration inhibitor b-10 (yield: 57%).

Synthesis Example 10: Synthesis of Migration Inhibitor b-11 (Compound 23-1)

According to the following scheme, a migration inhibitor b-11 was synthesized.

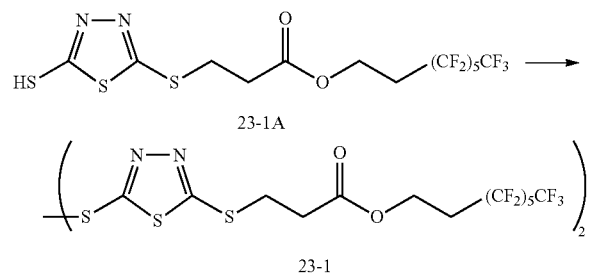

A compound 23-1A was synthesized by the same method as the method used for the compound 51-2. The compound 23-1A (3.0 g, 5.28 mmol) and ethyl acetate (20 ml) were put into a reaction container and thoroughly dissolved. Sodium iodide (79.1 mg, 0.528 mmol) and 30% hydrogen peroxide (22.11 mmol, 2.39 g) were added in this order to the resultant and stirred for 1 hour at room temperature. The educed crystals were washed with 100 ml of water, and 2.7 g of the obtained crude crystals were purified by silica gel column chromatography (mobile phase: hexane/ethyl acetate), thereby obtaining 2.4 g of the migration inhibitor b-11 (yield: 80%).

Synthesis Example 11: Synthesis of Migration Inhibitor b-12 (Compound X-6)

According to the following scheme, a compound M-2 was synthesized.

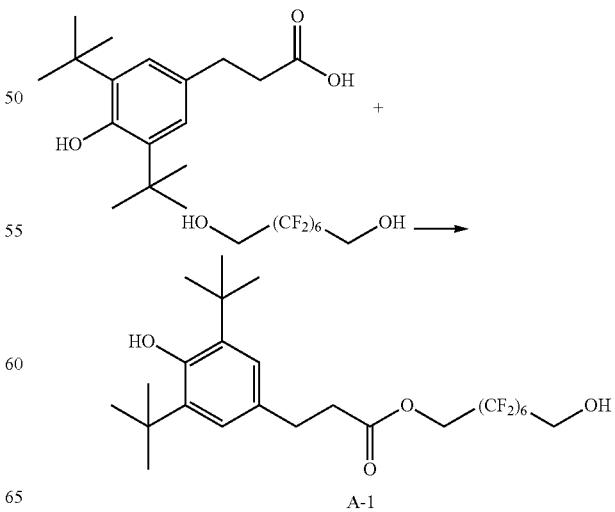

3-(3,5-di-tert-butyl-4-hydroxyphenyl)propionate (8.0 g, 28.8 mmol), dichloromethane (20 ml), 2,2,3,3,4,4,5,5,6,6,7,7-dodecafluoro-1,8-octanediol (20.8 g, 57.6 mmol), tetrahydrofuran (30 ml), 1-ethyl-3-(3-dimethylaminopropyl)carbodiimide hydrochloride (5.5 g, 28.8 mmol), and 4-dimethylaminopyridine (0.20 g, 1.44 mmol) were put in this order into a reaction container.

After the reaction solution was stirred for 3 hours at room temperature, 1 N hydrochloric acid (50 ml) was added to the reaction solution, and extraction was performed by using 100 ml of ethyl acetate. The organic phase was washed with saturated saline and dried over magnesium sulfate. The solid content was separated by filtration and then concentrated under reduced pressure. The obtained solid content was purified by silica gel column chromatography (mobile phase: hexane/ethyl acetate), thereby obtaining 10 g of the compound A-1.

room temperature and diluted with 4-methyl-2-pentanone (manufactured by Wako Pure Chemical Industries, Ltd.) (18.0 g). After reprecipitation was performed by using methanol, the precipitate was dried under reduced pressure, thereby obtaining 5 g of the migration inhibitor b-12 (Mw=41,000).

The molecular weight of the migration inhibitor b-12 means a weight average molecular weight which is measured by a gel permeation chromatography (GPC) method and expressed in terms of polystyrene. The weight average molecular weight was measured by the GPC method by dissolving the polymer in tetrahydrofuran and by using high-speed GPC apparatus (HLC-8220GPC) manufactured by TOSOH CORPORATION, TSKgel SuperHZ4000 (manufactured by TOSOH CORPORATION, 4.6 mm I. D.×15 cm) as a column, and tetrahydrofuran (THF) as an eluant.

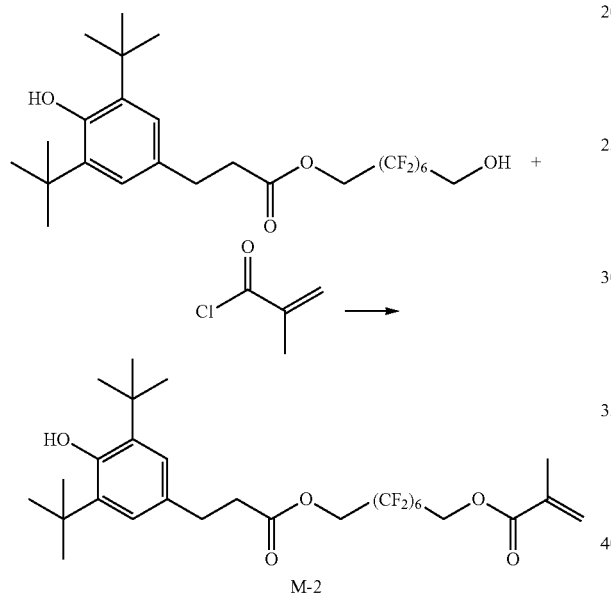

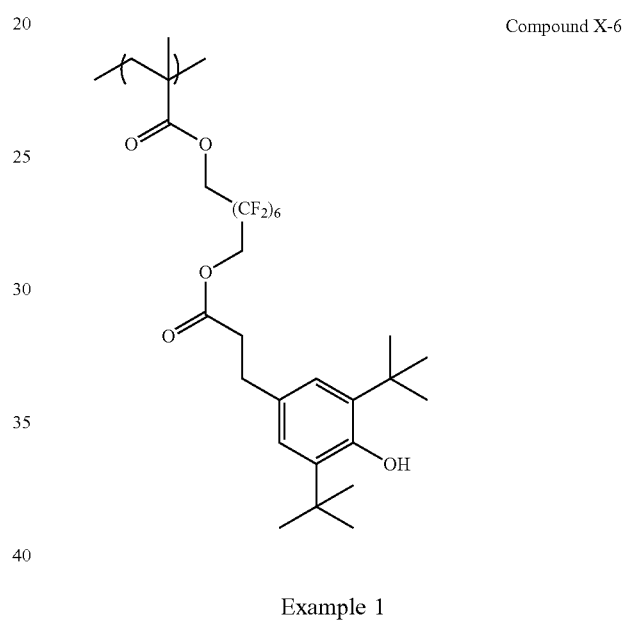

Compound X-6

Example 1

The compound A-1 (9.34 g, 15.0 mmol), tetrahydrofuran (100 ml), and triethylamine (1.52 g, 15.0 mmol) were put into a reaction container and cooled in an ice bath. Thereafter, methacrylic acid chloride (1.6 g, 15.0 mmol) was added dropwise to the reaction solution from a dropping funnel for 0.5 hours. Subsequently, the reaction solution was stirred for 3 hours at room temperature, 1 N hydrochloric acid (50 ml) was then added to the reaction solution, and extraction was performed by using 100 ml of ethyl acetate. The organic phase was washed with saturated saline and dried over magnesium sulfate. The solid content was separated by filtration and then concentrated under reduced pressure, and the obtained crude crystals were purified by silica gel column chromatography (mobile phase: hexane/ethyl acetate), thereby obtaining 8 g of M-2 (yield: 77%).

The compound M-2 (8 g) and 4-methyl-2-pentanone (manufactured by Wako Pure Chemical Industries, Ltd.) (16 g) were put into a 100 mL three-neck flask and heated to 80° C. in a nitrogen gas stream. To the resultant, a solution of azobisisobutyronitrile (manufactured by Wako Pure Chemical Industries, Ltd.) (49.3 mg) and 4-methyl-2-pentanone (manufactured by Wako Pure Chemical Industries, Ltd.) (2.0 g) was added, and the resultant was stirred for 16 hours. After the reaction ended, the reaction solution was cooled to (Preparation of Composition for Forming Gate Insulating Film)

By dissolving polyvinyl phenol/melamine (mass ratio=1/1) and the migration inhibitor b-1 in PGMEA (insulating material/migration inhibitor=100/20 (wt/wt), solution concentration (solid content concentration): 2% by mass), a composition for forming a gate insulating film was prepared. The obtained composition for forming a gate insulating film was named a composition 1.7

(Preparation of Organic Semiconductor Transistor)

Al to be a gate electrode was vapor-deposited (thickness: 50 nm) onto a glass substrate (Eagle XG: manufactured by Corning). Onto the Al, the composition 1 was applied by spin coating and baked for 60 minutes at 150° C., thereby forming a gate insulating film having a film thickness of 400 nm. Onto the gate insulating film, Au was vapor-deposited through a mask, thereby forming a source electrode and a drain electrode having a channel length of 20 μm and a channel width of 200 μm. Onto the source and drain electrodes, a composition for an organic semiconductor layer, which will be described later, was applied by spin coating at a rotation frequency of 2,000 rpm and baked for 15 minutes at 140° C., thereby forming an organic semiconductor layer having a thickness of 100 nm. Onto the organic semiconductor layer, Cytop CTL-107MK (manufactured by ASAHI GLASS CO., LTD.) (composition for forming a sealing layer) was applied by spin coating and baked for 10 minutes at 80° C., thereby forming a sealing layer (uppermost layer) having a thickness of 2 μm. In this way, an organic semiconductor transistor was obtained.

(Preparation of Composition for Organic Semiconductor Layer)

By dissolving TIPS pentacene (6,13-Bis(triisopropylsilylethynyl)pentacene, manufactured by Sigma-Aldrich Co, LLC.) in toluene (solution concentration: 2% by mass), a composition for an organic semiconductor layer was prepared.

(Measurement of Mobility)

Each of the electrodes of the prepared organic semiconductor transistor was connected to each of the terminals of a manual prober connected to 4155C manufactured by Agilent Technologies, thereby evaluating the field effect transistor (FET). Specifically, by measuring the drain current-gate voltage (Id-Vg) characteristics, a field effect mobility $\mu1$ ([cm$^2$/V·sec]) was calculated.

Thereafter, by using an organic thin film transistor prepared by using a composition not containing a migration inhibitor that was obtained by removing the migration inhibitor from the composition 1, the mobility was measured by the same method as described above, and a mobility $\mu2$ was calculated.

By using the obtained mobilities $\mu1$ and $\mu2$, a variation ($\mu1/\mu2$) was calculated and evaluated according to the following criteria. For practical use, an organic thin film transistor with a variation of equal to or greater than C is usable, and the variation is preferably equal to or greater than B.

$\mu1/\mu2 \geq 0.8$     [A]:

$0.8 > \mu1/\mu2 \geq 0.5$     [B]:

$0.5 > \mu1/\mu2 \geq 0.1$     [C]:

$0.1 > \mu1/\mu2$     [D]:

(Method for Evaluating Insulating Reliability)

The service life of the obtained organic semiconductor transistor was tested by using EHS-221MD (manufactured by Espec) under the following conditions, and the time taken for the value of resistance between source/drain electrodes to reach $1 \times 10^5 \Omega$ was measured. The measured time was named T1.

Temperature: 60° C.
Humidity: 60% RH
Pressure: 1.0 atm
Drain voltage: −40 V
Voltage between source/drain electrodes: 15 V According to the same procedure as used in Evaluation of mobility described above, an organic semiconductor transistor was prepared which used the composition for comparison not containing a migration inhibitor. For the obtained organic semiconductor transistor, the time taken for the value of resistance between source/drain electrodes to reach $1 \times 10^5 \Omega$ was measured according to the same procedure as used for measuring T1. The measured time was named T2.

From the calculated T1 and T2, T1/T2 was calculated and evaluated according to the following criteria. The results are shown in Table 1. From the viewpoint of insulation reliability, T1/T2 is preferably A, B, or C, more preferably A or B, and even more preferably A.

$T1/T2 \geq 5$     A:

$5 > T1/T2 \geq 2$     B:

$2 > T1/T2 > 1$     C:

$1 \geq T1/T2$     D:

Example 2

(Preparation of Composition for Forming Gate Insulating Film)

By dissolving Cytop CTL-809M (manufactured by ASAHI GLASS CO., LTD.) and the migration inhibitor b-1 in Cytop CT-SOLV180/1,1,1,3,3,3-hexafluoro-2-propanol (manufactured by Tokyo Chemical Industry Co., Ltd.) (9/1) (w/w) (insulating material/migration inhibitor=100/10 (w/w), solution concentration: 5% by mass), a composition for forming a gate insulating film was prepared. The obtained composition for forming a gate insulating film was named a composition 2.

(Preparation of Organic Semiconductor Transistor)

Al to be a gate electrode was vapor-deposited (thickness: 50 nm) onto a glass substrate (Eagle XG: manufactured by Corning). Onto the Al, the composition 2 was applied by spin coating and baked for 60 minutes at 150° C., thereby forming a gate insulating film having a film thickness of 400 nm.

Onto the gate insulating film, Au was vapor-deposited through a mask, thereby forming a source electrode and a drain electrode having a channel length of 20 μm and a channel width of 200 μm. Onto the source and drain electrodes, the composition for an organic semiconductor layer described above was applied by spin coating at a rotation frequency of 2,000 rpm and baked for 15 minutes at 140° C., thereby forming an organic semiconductor layer having a thickness of 100 nm. Onto the organic semiconductor layer, Cytop CTL-107MK (manufactured by ASAHI GLASS CO., LTD.) (composition for forming a sealing layer) was applied by spin coating and baked for 10 minutes at 80° C., thereby forming a sealing layer (uppermost layer) having a thickness of 2 μm. In this way, an organic semiconductor transistor was obtained.

The organic semiconductor transistor was evaluated as described in (Measurement of mobility) and (Method for evaluating insulation reliability).

Examples 3 to 13 and Comparative Examples 1 and 2

Compositions for forming a gate insulating film were prepared according to the same procedure as in Example 1, except that migration inhibitors b-2 to b-12 were used instead of the migration inhibitor b-1.

Furthermore, organic semiconductor transistors were prepared and evaluated in various ways according to the same procedure as in Example 1, except that the compositions for forming a gate insulating film shown in the following Table 1 were used instead of the composition 1. In Comparative examples 1 and 2, organic semiconductor transistors were prepared and evaluated according to the same procedure as in Examples 1 to 13, except that the compositions for forming a gate insulating film did not contain a migration inhibitor.

In Table 1, "PVP" means polyvinyl phenol.

TABLE 1

| | Example | | | | | | | |
|---|---|---|---|---|---|---|---|---|
| | 1 | 2 | 3 | 4 | 5 | 6 | 7 | 8 |
| Material of gate insulating film | PVP/melamine | Cytop | PVP/melamine | PVP/melamine | PVP/melamine | PVP/melamine | PVP/melamine | PVP/melamine |
| Migration inhibitor | b-1 | b-1 | b-2 | b-3 | b-4 | b-5 | b-6 | b-7 |
| Evaluation Mobility | A | A | A | A | A | A | A | A |
| Insulation reliability | A | A | A | B | A | B | B | B |

| | Example | | | | | Comparative example | |
|---|---|---|---|---|---|---|---|
| | 9 | 10 | 11 | 12 | 13 | 1 | 2 |
| Material of gate insulating film | PVP/melamine | PVP/melamine | PVP/melamine | PVP/melamine | PVP/melamine | PVP/melamine | Cytop |
| Migration inhibitor | b-8 | b-9 | b-10 | b-11 | b-12 | — | — |
| Evaluation Mobility | A | A | A | A | A | A | A |
| Insulation reliability | A | A | A | A | A | D | C |

As shown in Table 1, when the composition for forming a gate insulating film of the present invention was used, both the mobility and the insulation reliability of the organic thin film transistor could be satisfied.

In contrast, in comparative examples not containing a predetermined migration inhibitor, the mobility and the insulation reliability were poorer than those of examples.

EXPLANATION OF REFERENCES

10: substrate
20: gate electrode
30: gate insulating film
40: source electrode
42: drain electrode
50: organic semiconductor layer
60: sealing layer

What is claimed is:

1. A composition for forming a gate insulating film, comprising:
an insulating material; and
a migration inhibitor represented by a polymer compound (Y) containing a repeating unit represented by Formula (B) and a repeating unit represented by Formula (C),

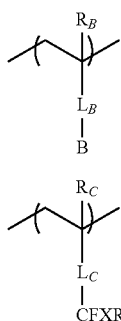

Formula (B)

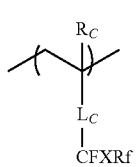

Formula (C)

in Formula (B), $R_B$ represents a hydrogen atom or an alkyl group having 1 to 4 carbon atoms that may have a substituent; $L_B$ represents a single bond or a divalent organic group; and B represents a monovalent group, which is formed as a result of removing one hydrogen atom (here, a hydrogen atom of a hydroxyl group is excluded) from compounds represented by the following Formulae (Y-1), in Formula (C), $R_C$ represents a hydrogen atom or an alkyl group having 1 to 4 carbon atoms that may have a substituent; $L_C$ represents a single bond or a divalent organic group; X represents a hydrogen atom, a fluorine atom, or a trifluoromethyl group; $R_f$ represents a fluoroalkyl group having 20 or less carbon atoms that may have an ethereal oxygen atom, in which at least one hydrogen atom is substituted with a fluorine atom, or a fluorine atom, $$P-(CR_1=Y)_n-Q \qquad \text{Formula (Y-1)}$$

in Formula (Y-1), each of P and Q independently represents OH, $NR_2R_3$, or $CHR_4R_5$; each of $R_2$ and $R_3$ independently represents a hydrogen atom or a group which can be substituted with a nitrogen atom; each of $R_4$ and $R_5$ independently represents a hydrogen atom or a substituent; Y represents $CR_6$ or a nitrogen atom; each of $R_1$ and $R_6$ independently represents a hydrogen atom or a substituent; at least two out of the groups represented by $R_1$, $R_2$, $R_3$, $R_4$, $R_5$, and $R_6$ may form a ring by being bonded to each other; n represents an integer of 1 to 5; when n represents a number of equal to or greater than 2, a plurality of atomic groups represented by $(CR_1=Y)$ may be the same as or different from each other.

2. An organic thin film transistor prepared by using the composition for forming a gate insulating film according to claim 1.

3. Electronic paper using the organic thin film transistor according to claim 2.

4. A display device using the organic thin film transistor according to claim 2.

* * * * *